US009464061B2

(12) United States Patent
Toscano et al.

(10) Patent No.: US 9,464,061 B2
(45) Date of Patent: Oct. 11, 2016

(54) N-HYDROXYLAMINO-BARBITURIC ACID DERIVATIVES

(71) Applicant: The Johns Hopkins University, Baltimore, MD (US)

(72) Inventors: John P. Toscano, Glen Arm, MD (US); Daryl A. Guthrie, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/926,607

(22) Filed: Oct. 29, 2015

(65) Prior Publication Data

US 2016/0060229 A1   Mar. 3, 2016

Related U.S. Application Data

(63) Continuation of application No. PCT/US2015/032493, filed on May 26, 2015.

(60) Provisional application No. 62/003,353, filed on May 27, 2014.

(51) Int. Cl.
*A61K 31/515* (2006.01)
*C07D 239/62* (2006.01)
*C07D 409/06* (2006.01)
*C07D 239/66* (2006.01)

(52) U.S. Cl.
CPC ........... *C07D 239/62* (2013.01); *C07D 409/06* (2013.01); *A61K 31/515* (2013.01); *C07D 239/66* (2013.01)

(58) Field of Classification Search
CPC . C07D 239/62; C07D 239/66; A61K 31/515
See application file for complete search history.

(56) References Cited

U.S. PATENT DOCUMENTS

| | | | |
|---|---|---|---|
| 3,751,255 A | 8/1973 | Wilson et al. | |
| 4,369,174 A | 1/1983 | Nagai et al. | |
| 4,539,321 A | 9/1985 | Campbell | |
| 4,663,351 A | 5/1987 | Diamond | |
| 4,798,824 A | 1/1989 | Belzer et al. | |
| 4,842,866 A | 6/1989 | Horder et al. | |
| 5,217,720 A | 6/1993 | Sekigawa et al. | |
| 6,525,081 B1 | 2/2003 | Matsumoto et al. | |
| 6,569,457 B2 | 5/2003 | Ullah et al. | |
| 6,638,534 B1 | 10/2003 | Ishibashi et al. | |
| 6,936,639 B2 | 8/2005 | Wink et al. | |
| 7,696,373 B2 | 4/2010 | King | |
| 7,863,262 B2 | 1/2011 | Wink et al. | |
| 7,989,652 B2 | 8/2011 | King | |
| 8,030,356 B2 | 10/2011 | Toscano et al. | |
| 8,227,639 B2 | 7/2012 | Toscano et al. | |
| 8,268,890 B2 | 9/2012 | Wink et al. | |
| 8,269,034 B2 | 9/2012 | King | |
| 8,318,705 B2 | 11/2012 | Frost et al. | |
| 8,569,536 B2 | 10/2013 | King | |
| 8,637,529 B2 * | 1/2014 | Woller ................ | C07D 487/04 514/262.1 |
| 8,674,132 B2 | 3/2014 | Toscano et al. | |
| 8,791,134 B2 | 7/2014 | Frost et al. | |
| RE45,314 E | 12/2014 | Toscano et al. | |
| 8,987,326 B2 | 3/2015 | Kalish et al. | |
| 9,018,411 B2 | 4/2015 | Toscano et al. | |
| 9,115,064 B2 | 8/2015 | Toscano et al. | |
| 9,156,804 B2 | 10/2015 | Kalish et al. | |
| 9,181,213 B2 * | 11/2015 | Toscano ............... | C07D 319/06 |
| 9,221,780 B2 | 12/2015 | Toscano et al. | |
| 2004/0038947 A1 | 2/2004 | Wink et al. | |
| 2005/0153966 A1 | 7/2005 | Gangloff et al. | |
| 2005/0192254 A1 | 9/2005 | Toscano et al. | |
| 2009/0186045 A1 | 7/2009 | Ray et al. | |
| 2009/0281067 A1 | 11/2009 | Toscano et al. | |
| 2009/0298795 A1 | 12/2009 | Paolocci et al. | |
| 2011/0081427 A1 | 4/2011 | Wink et al. | |
| 2011/0136827 A1 | 6/2011 | Toscano et al. | |
| 2011/0144067 A1 | 6/2011 | Toscano et al. | |
| 2011/0160200 A1 | 6/2011 | Mazhari et al. | |
| 2011/0306614 A1 | 12/2011 | Toscano et al. | |
| 2012/0201907 A1 | 8/2012 | Wink et al. | |
| 2014/0194416 A1 | 7/2014 | Toscano et al. | |
| 2014/0235636 A1 | 8/2014 | Toscano et al. | |
| 2014/0275134 A1 * | 9/2014 | Toscano ............... | C07D 319/06 514/270 |
| 2014/0336137 A1 | 11/2014 | Frost et al. | |
| 2014/0336396 A1 | 11/2014 | Toscano et al. | |
| 2015/0004259 A1 | 1/2015 | Wink et al. | |
| 2015/0141378 A1 | 5/2015 | Toscano et al. | |
| 2015/0197502 A1 | 7/2015 | Toscano et al. | |
| 2015/0291519 A1 | 10/2015 | Toscano et al. | |
| 2015/0336880 A1 | 11/2015 | Toscano et al. | |
| 2015/0344437 A1 | 12/2015 | Kalish et al. | |
| 2015/0366977 A1 | 12/2015 | Kalish et al. | |
| 2016/0002156 A1 | 1/2016 | Toscano et al. | |
| 2016/0031807 A1 | 2/2016 | Kalish et al. | |
| 2016/0046569 A1 | 2/2016 | Kalish et al. | |
| 2016/0046570 A1 | 2/2016 | Toscano et al. | |
| 2016/0052862 A1 | 2/2016 | Frost et al. | |
| 2016/0060229 A1 | 3/2016 | Toscano et al. | |
| 2016/0115148 A1 * | 4/2016 | Toscano ............... | C07D 239/62 514/270 |

FOREIGN PATENT DOCUMENTS

| | | |
|---|---|---|
| CN | 101472576 | 7/2009 |
| CN | 102076342 | 5/2011 |

(Continued)

OTHER PUBLICATIONS

D.A. Guthrie et al., 134 Journal of the American Chemical Society, 1962-1965 (2012).*

(Continued)

*Primary Examiner* — Alexander R Pagano

(74) *Attorney, Agent, or Firm* — Byrne Poh LLP; Nina R. Horan

(57) ABSTRACT

The present disclosure provides N-hydroxylamino-barbituric acid compounds of formulae (1)-(4), pharmaceutical compositions and kits comprising them, and methods of using such compounds or pharmaceutical compositions. The present disclosure provides methods of using such compounds or pharmaceutical compositions for treating heart failure.

124 Claims, 2 Drawing Sheets

(56) References Cited

FOREIGN PATENT DOCUMENTS

Figure 1A:
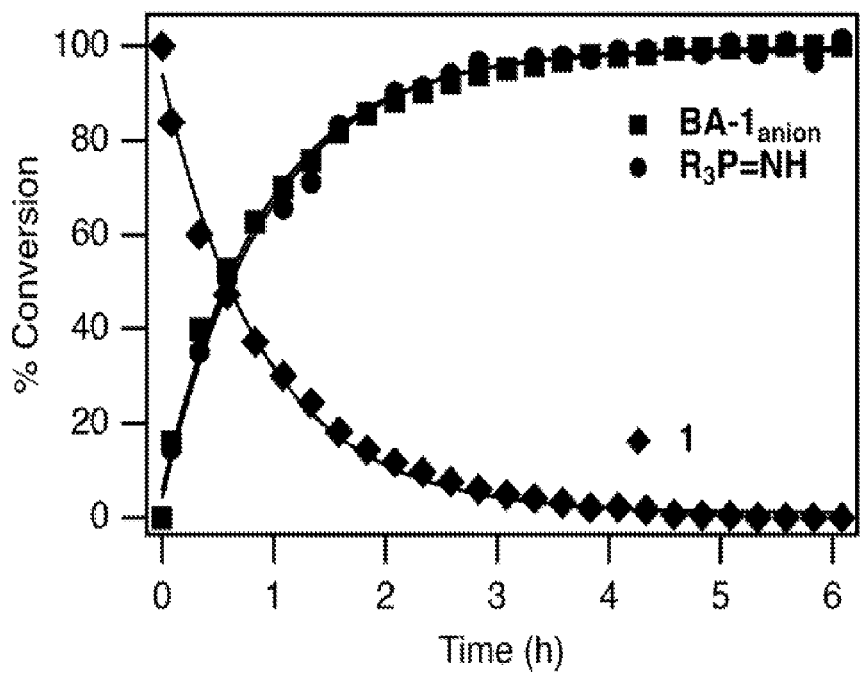

| WO | WO/01/10827 | 2/2001 |
|---|---|---|
| WO | WO/02/100810 | 12/2002 |
| WO | WO/2005/074598 | 8/2005 |
| WO | WO/2006/086188 | 8/2006 |
| WO | WO/2007/002444 | 1/2007 |
| WO | WO/2007/109175 | 9/2007 |
| WO | WO/2009/042970 | 4/2009 |
| WO | WO/2009/137717 | 11/2009 |
| WO | WO/2011/063339 | 5/2011 |
| WO | WO/2013/059194 | 4/2013 |
| WO | WO/2014/113700 | 7/2014 |

OTHER PUBLICATIONS

Andrei, D. et al., "Dual Mechanisms of HNO Generation by a Nitroxyl Prodrug of the Diazeniumdiolate (NONOate) Class", In the Journal of the American Chemical Society, vol. 132, No. 46, Nov. 24, 2010, pp. 16526-16532.

Armstrong, A. et al., "Oxaziridine-Mediated Amination of Primary Amines: Scope and Application to a One-Pot Pyrazole Synthesis", In Organic Letters, vol. 7, No. 4, Feb. 2005, pp. 713-716.

Badesch, D.B. et al., "Diagnosis and Assessment of Pulmonary Arterial Hypertension", In Journal of the American College of Cardiology, vol. 54, No. 1s1, Jun. 2009, pp. S55-S66.

Bazylinski, D.A. and Hollocher, T.C., "Metmyoglobin and Methemoglobin as Efficient Traps for Nitrosyl Hydride (Nitroxyl) in Neutral Aqueous Solution", In the Journal of the American Chemical Society, vol. 107, No. 26, Dec. 1985, pp. 7982-7986.

Bodor, N. and Buchwald, P., "Soft Drugs", In Retrometabolic Drug Design and Targeting, John Wiley & Sons, Oct. 2012, pp. 1-21.

Bonner, F.T. and Ko, Y., "Kinetic, Isotopic, and Nitrogen-15 NMR Study of N-Hydroxybenzenesulfonamide Decomposition: an Nitrosyl Hydride (HNO) Source Reaction", In Inorganic Chemistry, vol. 31, No. 12, Jun. 1, 1992, pp. 2514-2519.

Choe, C.U. et al., "Nitroxyl in the Central Nervous System", In Antioxidants & Redox Signaling, vol. 14, No. 9, May 1, 2011, pp. 1699-1711.

Cline, M.R. and Toscano, J.P., "Detection of Nitroxyl (HNO) by a Prefluorescent Probe", In the Journal of Physical Organic Chemistry, vol. 24, No. 10, Oct. 2011, pp. 993-998.

Cline, M.R. et al., "Oxidation of N-Hydroxy-l-Arginine by Hypochlorous Acid to Form Nitroxyl (HNO)", In the Journal of Inorganic Biochemistry, vol. 118, Jan. 2013, pp. 148-154.

Cline, M.R., "Detection of Nitroxyl (HNO) by Membrane Inlet Mass Spectrometry", In Free Radical Biology & Medicine, vol. 50, No. 10, May 2011, pp. 1274-1279.

Cohen, A.D. et al., "Direct Observation of an Acyl Nitroso Species in Solution by Time-Resolved IR Spectrocopy", In the Journal of the American Chemical Society, vol. 125, No. 6, Jan. 16, 2003, pp. 1444-1445.

Corrie, J.E.T. et al., "Reactions of Transient C-Nitrosocarbonyl Compounds with Dienes, Mono-Olefins, and Nucleophiles", In the Journal of the Chemical Society, Perkin Transactions 1, Jan. 1985, pp. 883-886.

Crawford, J.H. et al., "Hypoxia, Red Blood Cells, and Nitrite Regulate NO-Dependent Hypoxic Vasodilation", In Blood, vol. 107, No. 2, Jan. 2006, pp. 566-574.

Evans, A.S. and Toscano, J.P., "The Chemistry of NO- and HNO-Producing Diazeniumdiolates", in PATAI's Chemistry of Functional Groups, John Wiley & Sons, Ltd., Nov. 2010, pp. 1-16.

Evans, A.S. et al., "Photogeneration and Reactivity of Acyl Nitroso Compounds", In Canadian Journal of Chemistry, vol. 89, No. 2, Feb. 2011, pp. 130-138.

Flores-Santana, W. et al., "The Specificity of Nitroxyl Chemistry Is Unique Among Nitrogen Oxides in Biological Systems", In Antioxidants & Redox Signaling, vol. 14, No. 9, May 1, 2011, pp. 1659-1674.

Freelisch, M., "Nitroxyl gets to the Heart of the Matter", In Proceedings of the National Academy of Sciences, vol. 100, No. 9, Apr. 2003, pp. 4978-4980.

Froehlich, J.P. et al., "Phospholamban Thiols Play a Central Role in Activation of the Cardiac Muscle Sarcoplasmic Reticulum Calcium Pump by Nitroxyl", In Biochemistry, vol. 47, No. 50, Dec. 16, 2008, pp. 13150-13152.

Fukuto, J.M. et al., "The Physiological Chemistry and Biological Activity of Nitroxyl (HNO): The Neglected, Misunderstood, and Enigmatic Nitrogen Oxide", In Chemical Research in Toxicology, vol. 18, No. 5, May 2005, pp. 790-801.

Gao, W.D. et al., "Myofilament Ca2+ Sensitivity in Intact Versus Skinned Rat Ventricular Muscle", In Circulation Research, vol. 74, No. 3, Mar. 1994, pp. 408-415.

Gao, W.D. et al., "Relationship Between Intracellular Calcium and Contractile Force in Stunned Mocardium: Direct Evidence for Decreased Myofilament CA2+ Responsiveness and Altered Diastolic Function in Intact Ventricular Muscle", In Circulation Research, vol. 76, No. 6, Jun. 1995, pp. 1036-1048.

Gladwin, M.T. et al., "Nitrite as a Vascular Endocrine Nitric Oxide Reservoir that Contributes to Hypoxic Signaling, Cytoprotection, and Vasodilation", In the American Journal of Physiology Heart and Circulatory Physiology, vol. 291, No. 5, Nov. 2006, pp. H2026-H2035.

Gladwin, M.T. et al., "The Emerging Biology of the Nitrite Anion", In Nature Chemical Biology, vol. 1, No. 6, Nov. 2005, pp. 308-314.

Guthrie, D.A. et al., "'Catch-and-Release' of HNO with Pyrazolones", In the Journal of Organic Chemistry, vol. 80, No. 3, Jan. 16, 2015, pp. 1338-1348.

Guthrie, D.A. et al., "Curtailing the Hydroxylaminobarbituric Acid-Hydantoin Rearrangement to Favor HNO Generation", In the Journal of Organic Chemistry, vol. 80, No. 3, Jan. 13, 2015, pp. 1349-1356.

Guthrie, D.A. et al., "Development of N-Substituted Hydroxylamines as Efficient Nitroxyl (HNO) Donors", In the Journal of the American Chemical Society, vol. 134, No. 4, Feb. 1, 2012, pp. 1962-1965.

Hare, J.M. et al., "Pertussis Toxin-Sensitive G Proteins Influence Nitric Oxide Synthase III Activity and Protein Levels in Rat Heart", In the Journal of Clinical Investigations, vol. 101, No. 6, Mar. 1998, pp. 1424-1431.

Higashi, Y. et al., "Edaravone (3-methyl-1-phenyl-2-pyrazolin-5-one), a Novel Free Radical Scavenger, for Treatment of Cardiovascular Diseases", In Recent Patents on Cardiovascular Drug Discovery, vol. 1, No. 1, Jan. 2006, pp. 85-93.

Hughes, M.N. and Cammack, R., "Synthesis, Chemistry, and Applications of Nitroxyl Ion Releasers Sodium Trioxodinitrate or Angeli's Salt and Piloty's Acid", In Methods in Enzymology, vol. 301, Feb. 1999, pp. 279-287.

Ingall, T.J., "Preventing Ischemic Stroke", In Postgraduate Medicine, vol. 107, No. 6, May 2000, pp. 34-50.

International Patent Application No. PCT/US2012/060425, filed Oct. 16, 2012.

International Patent Application No. PCT/US2015/032493, filed May 26, 2015.

International Preliminary Report on Patentability dated May 1, 2014 in International Patent Application No. PCT/US2012/060425.

International Search Report and Written Opinion dated May 1, 2014 in International Patent Application No. PCT/US20125/060425.

International Search Report and Written Opinion dated Sep. 30, 2015 in International Patent Application No. PCT/US2015/032493.

Jursic, B.S. and Stevens, E.D., "Mono C-Alkylation and Mono C-Benzylation of Barbituric Acids through Zinc/Acid Reduction of Acyl, Benzylidene, and Alkylidene Barbiturate Intermediates", In Tetrahedron Letters, vol. 44, No. 10, Mar. 2003, pp. 2203-2210.

Katori, T. et al., "Calcitonin Gene-Related Peptide in Vivo Positive Inotropy is Attributable to Regional Sympatho-Stimulation and is Blunted in Congestive Heart Failure", In Circulation Research, vol. 96, No. 2, Feb. 2005, pp. 234-243.

Keceli, G. and Toscano, J.P., "Reactivity of Nitroxyl-Derived Sulfinamides", In Biochemistry, vol. 51, No. 20, May 2012, pp. 4206-4216.

(56) References Cited

OTHER PUBLICATIONS

Keceli, G. et al., "NMR Detection and Study of Hydrolysis of HNO-Derived Sulfinamides", In Biochemistry, vol. 52, No. 42, Oct. 2013, pp. 7387-7396.

Kemp-Harper, B.K., "Nitroxyl (HNO): A Novel Redox Signaling Molecule", In Andioxidants & Redox Signaling, vol. 14, No. 9, May 1, 2011, pp. 1609-1613.

Lofberg, C. et al., "Sequential One-Pot Bimetallic Ir(III)/Pd(0) Catalysed Mono-/Bis-Alkylation and Spirocyclisation Processes of 1,3-Dimethylbarbituric Acid and Allenes", In Chemical Communications, vol. 48, Nov. 2006, pp. 5000-5002.

Ma, X.L. et al., "Opposite Effects of Nitric Oxide and Nitroxyl on Postischemic Myocardial Injury", In Proceedings of the National Academy of Sciences of the United States of America, vol. 96, No. 25, Dec. 1999, pp. 14617-14622.

Meusel, M. et al., "The Aminobarbituric Acid-Hydantoin Rearrangement", In the Journal of Organic Chemistry, vol. 68, No. 12, May 2003, pp. 4684-4692.

Minicone, F. et al., "Carbonic Anhydrase Inhibitors: Inhibition of Isozymes I, II and IV with N-Hydroxysulfonamides-a Novel Class of Intraocular Pressure Lowering Agents", In the Journal of Enzyme Inhibition and Medicinal Chemistry, vol. 13, No. 4, Jul. 1998, pp. 267-284.

Miranda, K.M. et al., "Comparison of the NO and HNO Donating Properties of Diazeniumdiolates: Primary Amine Adducts Release HNO in Vivo", In the Journal of Medicinal Chemistry, vol. 48, No. 26, Dec. 29, 2005, pp. 8220-8228.

Miranda, K.M. et al., "Donors of HNO", In Current Topics in Medicinal Chemistry, vol. 5, No. 7, Jan. 2005, pp. 649-664.

Norris, A.J. et al., "Nitroxyl Inhibits Breast Tumor Growth and Angiogenesis", In the International Journal of Cancer, vol. 122, No. 8, Apr. 2008, pp. 1905-1910.

Notice of Allowance dated Jul. 6, 2015 in U.S. Appl. No. 14/352,399.

Nutaitis, C.F. et al., "Reduction of Isopropylidene Acylmalonates, 5-Acylbarbituric Acids, and 3-Acyl-4-Hydroxycoumarins to the Corresponding Alkyl Derivatives by Sodium Cyanoborohydride-Acetic Acid", In the Journal of Organic Chemistry, vol. 45, No. 23, Nov. 1980, pp. 4606-4608.

Office Action dated Jan. 23, 2015 in Chinese Patent Application No. 201280051009.4.

Office Action dated Nov. 17, 2015 in Israel Patent Application No. 232101.

Office Action dated Nov. 27, 2015 in Chinese Patent Application No. 201280051009.4.

Office Action dated Mar. 12, 2014 in Australian Patent Application No. 2013201929.

Office Action dated Jun. 17, 2015 in European Patent Application No. 12781538.9.

Paolocci, N. et al., "cGMP-Independent Inotropic Effects of Nitric Oxide and Peroxynitrite Donors: Potential Role for Nitrosylation", In the American Journal of Physiology, Heart and Circulatory Physiology, vol. 279, No. 4, Oct. 2000, pp. H1982-H1988.

Paolocci, N. et al., "Nitroxyl Anion Exerts Redox-Sensitive Positive Cardiac Inotropy in Vivo by Calcitonin Gene-Related Peptide Signaling", In Proceedings of the National Academy of Sciences, vol. 98, No. 18, Aug. 28, 2001, pp. 10463-10468.

Paolocci, N. et al., "Positive Inotropic and Lusitropic Effects of HNO/NO- in Failing Hearts: Independence from β-Adrenergic Signaling", In Proceedings of the National Academy Sciences, vol. 100, No. 9, Apr. 29, 2003, pp. 5537-5542.

Paolocci, N. et al., "The Pharmacology of Nitroxyl (HNO) and its Therapeutic Potential: Not just the Janus Face of NO", In Pharmacology and Therapeutics, vol. 113, No. 2, Feb. 2007, pp. 442-458.

Porcheddu, A. et al., "A Straightforward Route to Piloty's Acid Derivatives: A Class of Potential Nitroxyl-Generating Prodrugs", In Synlett, vol. 2009, No. 13, Aug. 2009, pp. 2149-2153.

Raillar, S.P. et al., "Preparation and Improved Stability of N-Boc-a-Amino-5-Acyl Meldrum's Acids, a Versatile Class of Building Blocks for Combinatorial Chemistry", In the Journal of Combinatorial Chemistry, vol. 4, No. 5, Sep. 2002, pp. 470-474.

Rastaldo, R. et al., "Cytochrome P-450 Metabolite of Arachidonic Acid Mediates Bradykinin-Induced Negative Inotropic Effect", In the American Journal of Physiology Heart and Circulatory Physiology, vol. 280, No. 6, Jun. 2001, pp. H2823-H2832.

Rehse, K. and Hahrouri, T., "New NO Donors with Antithrombotic and Vasodilating Activities, part 25. Hydroxylamine Derivatives", In Archiv der Pharmazie, vol. 331, No. 11, Nov. 1998, pp. 365-367.

Reisz, J.A. et al., "Rapid and Selective Nitroxyl (HNO) Trapping by Phosphines: Kinetics and New Aqueous Ligations for HNO Detection and Quantitation", In the Jouranl of the American Chemical Society, vol. 133, No. 30, Jun. 2011, pp. 11675-11685.

Reisz, J.A. et al., "Reductive Phosphine-Mediated Ligation of Nitroxyl (HNO)", In Organic Letters, vol. 11, No. 13, Jun. 2009, pp. 2719-2721.

Sabbah, H.N. et al., "Nitroxyl (HNO) a Novel Approach for the Acute Treatment of Heart Failure", In Circulation: Heart Failure, vol. 6, No. 6, Nov. 2013, pp. 1250-1258.

Salmon, D.J. et al., "HNO and NO Release from a Primary Amine-Based Diazeniumdiolate as a Function of pH", In Inorganic Chemistry, vol. 50. No. 8, Apr. 18, 2011, pp. 3262-3270.

Scozzafava, A. et al., "Carbonic Anhydrase & Matrix Metalloproteinase Inhibitors:Sulfonylated Amino Acid Hydroxamates w/ MMP Inhibitory Properties Act as Efficient Inhibitors of CA Isozymes I, II & IV, & N-Hydroxysulfonamides Inhibit Both Zinc Enzymes", In J. Med. Chem.,vol. 43, No. 20, Oct. 2000, pp. 3677-3687.

Sha, X. et al., "Hydrolysis of Acyloxy Nitroso Compounds Yields Nitroxyl (HNO)", In the Journal of the American Chemical Society, vol. 128, No. 30, Jul. 2006, pp. 9687-9692.

Shoman, M.E. et al., "Acyloxy Nitroso Compounds as Nitroxyl (HNO) Donors: Kinetics, Reactions with Thiols, and Vasodilation Properties", In the Journal of Medicinal Chemistry, vol. 54, No. 4, Feb. 24, 2011, pp. 1059-1070.

Simonneau, G. et al., "Updated Clinical Classification of Pulmonary Hypertension", In the Journal of the American College of Cardiology, vol. 54, No. 1s1, Jun. 2009, pp. S43-S54.

Slotwiner-Nie, P.K. and Brandt, L.J., "Infectious Diarrhea in the Elderly", In Gastroenterology Clinics, vol. 30, No. 3, Sep. 2001, pp. 625-635.

Stoyanovsky, D.A. et al., "Effects of pH on the Cytotoxicity of Sodium Trioxodinitrate (Angeli's Salt)", In the Journal of Medicinal Chemistry, vol. 47, No. 1, Dec. 2003, pp. 210-217.

Sutton, A.D. et al., "Optimization of HNO Production from N,O-Bis-Acylated Hydroxylamine Derivatives", In Organic Letters, vol. 14, No. 2, Jan. 20, 2012, pp. 472-475.

Tate, J.V. et al., "Preparation of 5-Substituted Benzylbarburituric Acids and Investigation of the Effect of the Benzyl and Substituted Benzyl Groups on the Acidity of Barbituric Acid", In the Journal of Heterocyclic Chemistry, vol. 23, No. 1, Jan./Feb. 1986, pp. 9-11.

Thevis, M. et al., "High Speed Determination of Beta-Receptor Blocking Agents in Human Urine by Liquied Chromatography/ Tandem Mass Spectrometry", In Biomedical Chromatography, vol. 15, No. 6, Oct. 2001, pp. 393-402.

Timoshinina, L.G. and Vvedenskii, V.M., "Reaction of Dialuric Acid with Hydrazine Derivatives", In Chemistry of Heterocyclic Compounds, vol. 9, No. 2, Feb. 1973, pp. 247-249.

Tocchetti, C.G. et al., "Nitroxyl Improves Cellular Heart Function by Directly Enhancing Cardiac Sarcoplasmic Reticulum Ca2+ Cycling", In Circulation Research, vol. 100, No. 1, Jan. 5, 2007, pp. 96-104.

Tocchetti, C.G. et al., "Playing with Cardiac "Redox Switches": The "HNO Way" to Modulate Cardiac Function", In Antioxidants & Redox Signaling, vol. 14, No. 9, May 1, 2011, pp. 1687-1698.

Watanabe, K. et al. "Structure—Activity Relationship of 3-Methyl-1-Phenyl-2-Pyrazolin-5-One (Edaravone)", In Redox Report, vol. 8, No. 3, Jun. 1, 2003, pp. 151-155.

(56) References Cited

OTHER PUBLICATIONS

Watanabe, T. et al., "The Novel Antioxidant Edaravone: From Bench to Bedside", In Cardiovascular Therapeutics, vol. 26, No. 2, Jun. 2008, pp. 101-114.

Xu, Y. et al., "Production of Nitroxyl (HNO) at Biologically Relevant Temperatures from the Retro-Diels-Alder Reaction of N-Hydroxyurea-Derived Acyl Nitroso-9,10-Dimethylanthracene Cycloadducts", In Tetrahedron Letters, vol. 41, No. 22, Jun. 8, 2000, pp. 4265-4269.

Yranzo, G.I. et al., "Flash Vacuum Pyrolysis of 2-Alkoxyiminated Alkyl α-Pyrone and 1,3-Diazine Derivatives", In Journal of Analytical and Applied Pyrolysis, vol. 46, No. 2, Aug. 1998, pp. 101-112.

Zamora, R. et al., "Oxidative Release of Nitric Oxide Accounts for Guanylyl Cyclase Stimulating, Vasodilator and Anti-Platelet Activity of Piloty's Acid: a Comparison with Angeli's Salt", In Biochemistry Journal, vol. 312, No. 2, Dec. 1995, pp. 333-339.

* cited by examiner

N-HYDROXYLAMINO-BARBITURIC ACID DERIVATIVES

CROSS-REFERENCE TO RELATED APPLICATIONS

This application is a continuation of International Patent Application No. PCT/US2015/032493 filed May 26, 2015, which claims the benefit of U.S. provisional Patent Application No. 62/003,353, filed May 27, 2014, each of which is hereby incorporated by reference in its entirety.

BACKGROUND

Nitroxyl (HNO) has been shown to have positive cardiovascular effects in in vitro and in vivo models of failing hearts. However, at physiological pH, HNO dimerizes to hyponitrous acid, which subsequently dehydrates to nitrous oxide. Because of this metastability, HNO for therapeutic use is generated in situ from donor compounds. A variety of compounds capable of donating nitroxyl have been described and proposed for use in treating disorders known or suspected to be responsive to nitroxyl. See, e.g., U.S. Pat. Nos. 6,936,639; 7,696,373; 8,030,356; 8,268,890; 8,227,639; and 8,318,705; U.S. pre-grant publication nos. 2009/0281067; 2009/0298795; 2011/0136827; and 2011/0144067; International PCT Publication No. WO 2013/059194 and Paolocci et al., "The pharmacology of nitroxyl (HNO) and its therapeutic potential: Not just the janus face of NO," *Pharmacol. Ther.* 113 (2007) 442-458. Although all of these compounds are disclosed to be capable of donating nitroxyl, they differ in various physicochemical properties, and there remains a need to identify nitroxyl donors that have physicochemical properties best suited for treating specific clinical conditions via specific routes of administration.

International PCT Publication No. WO 2013/059194 describes N-hydroxylamino-barbituric acid (HABA) type compounds that are capable of donating nitroxyl. One such compound, 5-(N-hydroxylamine)-5-ethyl-N,N-dimethylbarbituric acid (5-ethyl HABA), however, was reported to produce less than the desired amount of HNO. Further studies showed that this compound undergoes a competitive intramolecular rearrangement mechanism rather than the desired HNO producing mechanism. It was found that, by exchanging the 5-ethyl group with an O-methyloxime group, the non-HNO producing mechanism was avoided. Scheme 1 shows the major reaction pathways for the 5-ethyl HABA compound (intramolecular rearrangement pathway) and for the corresponding 5-O-methyloxime HABA compound (desired HNO producing pathway).

Scheme 1.

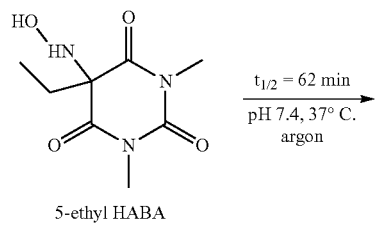

5-ethyl HABA

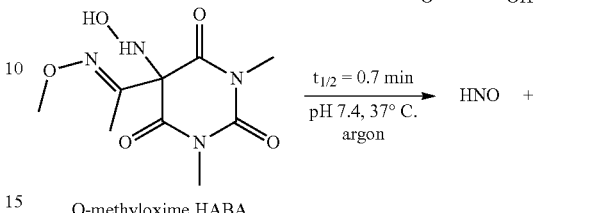

O-methyloxime HABA

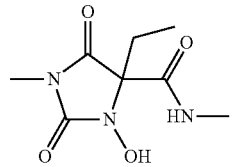

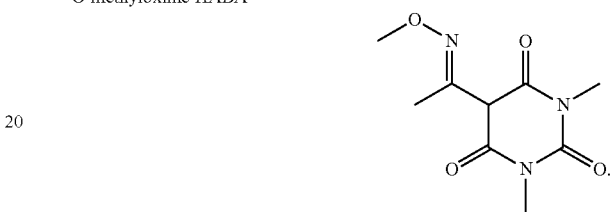

Accordingly, there is a need to provide new HABA type nitroxyl donating compounds that have a suitable toxicological profile and that undergo the desired HNO producing pathway under physiologically relevant conditions. Development of such compounds requires an understanding of the pharmacokinetic profile associated with nitroxyl donation and the factors influencing the toxicological profile and HNO production. Failure to understand these factors has hampered the development of nitroxyl donors for clinical use.

Citation of any reference in Section 1 of this application is not to be construed as an admission that such reference is prior art to the present application.

2. SUMMARY OF THE DISCLOSURE

The present disclosure relates to nitroxyl donating compounds (referred to herein as nitroxyl donors), pharmaceutical compositions comprising such compounds, kits, and methods of using such compounds or pharmaceutical compositions for treating conditions responsive to nitroxyl therapy. The compounds of the present disclosure produce, or are believed to produce, HNO under physiologically relevant conditions. In addition, the compounds of the disclosure have, or are believed to have, suitable toxicological profiles.

In a first embodiment, the present disclosure provides HABA type nitroxyl donating compounds that have half-lives of greater than about 10 minutes when measured under the conditions specified in Example 17 or Example 18. In particular embodiments, the HABA type nitroxyl donating compounds of the present disclosure have half-lives from about 10 minutes to about 4000 minutes when measured under the conditions specified in Example 17. In specific embodiments, the HABA type nitroxyl donating compounds of the present disclosure have half-lives from about 15 minutes to about 3900 minutes when measured under the conditions specified in Example 17. In particular embodiments, the HABA type nitroxyl donating compounds of the present disclosure have half-lives from about 10 minutes to about 200 minutes when measured under the conditions specified in Example 18. In specific embodiments, the HABA type nitroxyl donating compounds of the present disclosure have half-lives from about 12 minutes to about 190 minutes when measured under the conditions specified in Example 18.

In a second embodiment, the present disclosure provides HABA type nitroxyl donating compounds that produce a percent yield of HNO greater than about 50% when measured under the conditions specified in Example 17. In particular embodiments, the HABA type nitroxyl donating compounds of the present disclosure produce a percent yield of HNO from about 75% to about 100% when measured under the conditions specified in Example 17. In specific embodiments, the HABA type nitroxyl donating compounds of the present disclosure produce a percent yield of HNO from about 85% to about 100% when measured under the conditions specified in Example 17.

In a third embodiment, the present disclosure provides HABA type nitroxyl donating compounds that have a half-life of greater than about 10 minutes when measured under the conditions described in Example 17 or Example 18 and that produce a percent yield of HNO greater than about 50% when measured under the conditions described in Example 17.

In a fourth embodiment, the present disclosure provides HABA type nitroxyl donating compounds that have a half-life from about 10 minutes to about 4000 minutes when measured under the conditions described in Example 17 and that produce a percent yield of HNO from about 75% to about 100% when measured under the conditions described in Example 17.

In a fifth embodiment, the present disclosure provides HABA type nitroxyl donating compounds that have a half-life from about 10 minutes to about 200 minutes when measured under the conditions described in Example 18 and that produce a percent yield of HNO from about 75% to about 100% when measured under the conditions described in Example 17.

In a sixth embodiment, the present disclosure provides HABA type nitroxyl donating compounds that have a half-life from about 15 minutes to about 3900 minutes when measured under the conditions described in Example 17 and that produce a percent yield of HNO from about 85% to about 100% when measured under the conditions described in Example 17.

In a seventh embodiment, the present disclosure provides HABA type nitroxyl donating compounds that have a half-life from about 12 minutes to about 190 minutes when measured under the conditions described in Example 18 and that produce a percent yield of HNO from about 85% to about 100% when measured under the conditions described in Example 17.

Provided that, in each of the seven preceding embodiments, the HABA type nitroxyl donating compound is not 5-(N-hydroxylamino)-5-ethyl-N,N-dimethylbarbituric acid or 5-(N-hydroxylamino)-5-(acetyl-O-methyloxime)-N,N-dimethylbarbituric acid.

In a particular embodiment, the present disclosure provides a nitroxyl donating compound of the formula (1):

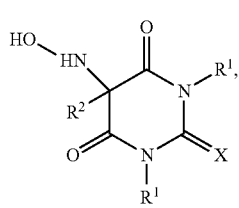

(1)

or a pharmaceutically acceptable salt thereof, wherein:
each $R^1$ is independently H or $(C_1)$alkyl;
$R^2$ is $(C_1-C_6)$alkyl substituted with a substituent selected from the group consisting of $(C_6-C_{14})$aryl, $(C_3-C_6)$cycloalkyl, $(C_5-C_7)$heterocycloalkyl, (5- or 6-membered)heteroaryl and (9- or 10-membered)heteroaryl, wherein said aryl, cycloalkyl, heterocycloalkyl and heteroaryl are unsubstituted or substituted with 1, 2, 3, 4 or 5 substituents selected from $R^4$ and said alkyl is unsubstituted or substituted with 1, 2 or 3 substituents selected from $R^6$;
X is O, $NR^7$ or S;
each $R^4$ is independently selected from the group consisting of halo, —OH, —NH$_2$, —C≡N, —NO$_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl;
each $R^6$ is independently selected from the group consisting of halo and $(C_1-C_6)$alkyl; and
$R^7$ is H or $(C_1-C_6)$alkyl.

In another particular embodiment, the present disclosure provides a nitroxyl donating compound of the formula (2):

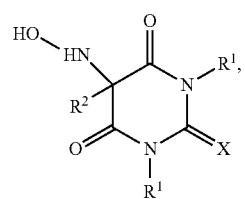

(2)

or a pharmaceutically acceptable salt thereof, wherein:
each $R^1$ is independently H or $(C_1)$alkyl;
$R^2$ is selected from the group consisting of a branched $(C_3-C_6)$alkyl, a branched $(C_3-C_6)$alkenyl, and a branched $(C_3-C_6)$alkoxy, wherein said alkyl, alkenyl, and alkoxy are unsubstituted or substituted with 1, 2 or 3 substituents selected from $R^4$;
X is O, $NR^7$ or S;
each $R^4$ is independently selected from the group consisting of halo, —OH, —NH$_2$, —C≡N, —NO$_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl; and
$R^7$ is H or $(C_1-C_6)$alkyl.

In another particular embodiment, the present disclosure provides a nitroxyl donating compound of the formula (3):

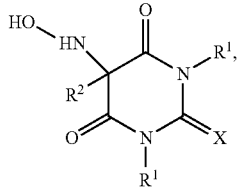

(3)

or a pharmaceutically acceptable salt thereof, wherein:
each $R^1$ is H;
$R^2$ is selected from the group consisting of $(C_1-C_6)$alkyl, $(C_2-C_6)$alkenyl, $(C_2-C_6)$alkynyl and $(C_1-C_6)$alkoxy, wherein said alkyl, alkenyl, alkynyl and alkoxy are unsubstituted or substituted with 1, 2 or 3 substituents selected from $R^4$;
X is O, $NR^7$ or S;
each $R^4$ is independently selected from the group consisting of halo, —OH, —$CH_2OH$, —$NH_2$, —C≡N, —$NO_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)$NH_2$, —C(O)OH, —NH—C(O)—$NH_2$, —NH—C(NH)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl; and
$R^7$ is H or $(C_1-C_6)$alkyl.

In another particular embodiment, the present disclosure provides a nitroxyl donating compound of the formula (4):

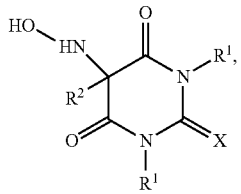

(4)

or a pharmaceutically acceptable salt thereof, wherein:
each $R^1$ is independently H or $(C_1)$alkyl;
$R^2$ is $(C_6-C_{10})$aryl, $(C_3-C_6)$cycloalkyl, $(C_5-C_7)$heterocycloalkyl and (5- or 6-membered)heteroaryl, wherein said aryl, cycloalkyl, heterocycloalkyl and heteroaryl are unsubstituted or substituted with 1, 2, 3, 4 or 5 substituents selected from $R^4$;
X is O, $NR^7$ or S;
each $R^4$ is independently selected from the group consisting of halo, —OH, —$NH_2$, —C≡N, —$NO_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl; and
$R^7$ is H or $(C_1-C_6)$alkyl.

In another particular embodiment, the present disclosure provides a nitroxyl donating compound of the formula (5):

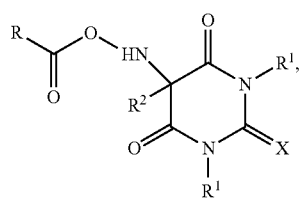

(5)

or a pharmaceutically acceptable salt thereof, wherein:
$R^1$, $R^2$ and X together are as defined herein for each of compounds of formulae (1), (1a), (1a-1), (1a-2), (1b), (1c), (1d), (2), (3), (3a), (3a-1), (3b), (3c), (3d), (4), (4a), (4b), (4c) and (4d); and
R is hydrogen, —$(C_1-C_6)$alkyl, —$(C_2-C_4)$alkenyl, phenyl, benzyl, cyclopentyl, cyclohexyl, —$(C_5-C_7)$heterocycloalkyl, benzyloxy, —O—$(C_1-C_6)$alkyl, —$NH_2$, —NH—$(C_1-C_4)$alkyl, or —N$((C_1-C_4)$alkyl$)_2$, wherein said —$(C_1-C_6)$alkyl, —$(C_2-C_4)$alkenyl, phenyl, benzyl, cyclopentyl, cyclohexyl, —$(C_5-C_7)$heterocycloalkyl, benzyloxy, —O—$(C_1-C_6)$alkyl, —NH—$(C_1-C_4)$alkyl, or —N$((C_1-C_4)$alkyl$)_2$ can be unsubstituted or substituted with 1, 2 or 3 substituents selected from halo, —$(C_1-C_6)$alkyl, —$(C_2-C_4)$alkenyl, —$(C_2-C_3)$alkynyl, -(5- or 6-membered)heteroaryl, —O—$(C_1-C_6)$alkyl, —S—$(C_1-C_6)$alkyl, —C(halo)$_3$, —CH(halo)$_2$, —$CH_2$(halo), —CN, —$NO_2$, —$NH_2$, —NH—$(C_1-C_4)$alkyl, —N(—$(C_1-C_4)$alkyl)$_2$, —C(O)$(C_1-C_4)$alkyl, —C(O)O$(C_1-C_4)$alkyl, —OC(O)$(C_1-C_4)$alkyl, —OC(O)$NH_2$, —S(O)$(C_1-C_4)$alkyl, or —S(O)$_2(C_1-C_4)$alkyl.

Compounds of the disclosure are or are believed to be nitroxyl donors under physiologically relevant conditions. For example, compounds (1)-(4), (11), (12), and (18) undergo the desired HNO producing pathway, quantitatively producing HNO in phosphate buffered saline, pH of 7.4, each measured in Example 17.

In addition, the compounds of the disclosure have or are believed to have desirable toxicological profiles. It has been discovered that the desirable toxicological profile of the present compounds stem in part from their half-lives, and the discovery of an optimal range of half-lives for nitroxyl donors. For example, compounds (1)-(4), (11), (12) and (18) have half-lives from approximately 15 minutes to approximately 3900 minutes, each measured under the conditions of Example 17, and compounds (1)-(10), (14), (16) and (17) have half-lives from approximately 14 minutes to approximately 189 minutes, each measured under the conditions of Example 18.

Compounds and/or compositions of the disclosure can be used to treat a variety of conditions that are responsive to nitroxyl therapy. For instance, the compounds and/or compositions of the disclosure can be used to treat or prevent the occurrence of cardiovascular diseases, alcoholism, vascular dysfunction and cancer. In certain embodiments, a nitroxyl donating composition of the disclosure can be used to treat cardiovascular disease, ischemia/reperfusion injury, pulmonary hypertension or another condition responsive to nitroxyl therapy. In particular embodiments, a nitroxyl donating composition of the disclosure can be used to treat heart failure. In a particular embodiment, a compound and/or composition of the disclosure can be used to treat decompensated heart failure (e.g., acute decompensated heart failure). In certain embodiments, the compounds and/or compositions of the disclosure can be used to treat systolic heart failure. In particular embodiments, the compounds and/or compositions of the disclosure can be used to treat diastolic heart failure.

3. BRIEF DESCRIPTION OF FIGURES

Figure 1B:
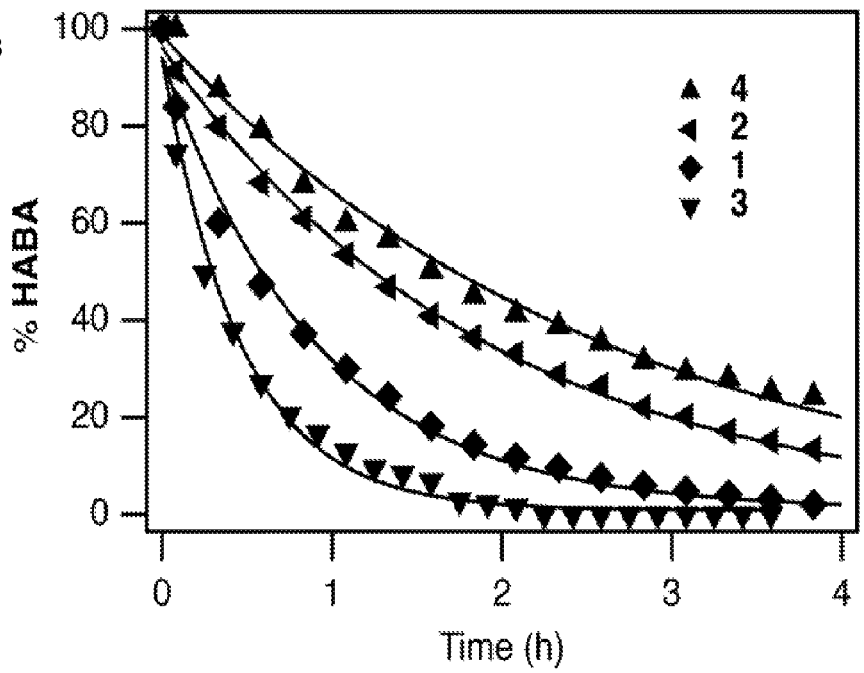

FIG. 1A and FIG. 1B show nitroxyl production as determined via $^1$H NMR protocol using added TXPTS. FIG. 1A shows the time course disappearance of a compound of the disclosure (compound (1)) and appearance of its corresponding barbituric acid (compound BA-1 anion) and TXPTS aza-ylide. The solid curves are calculated best fits to a single exponential function of the integrated $^1$H NMR data (k=3.1× $10^{-4}$ s$^{-1}$ for each fit) (see Example 17). FIG. 1B shows the disappearance of four compounds of the disclosure (compound (1), compound (2), compound (3), and compound (4)) under conditions outlined in Table 2.

Figure 2A:
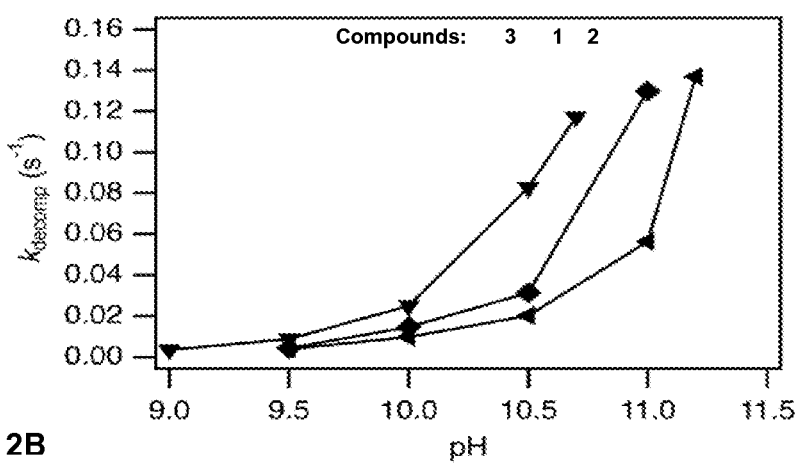
Figure 2B:
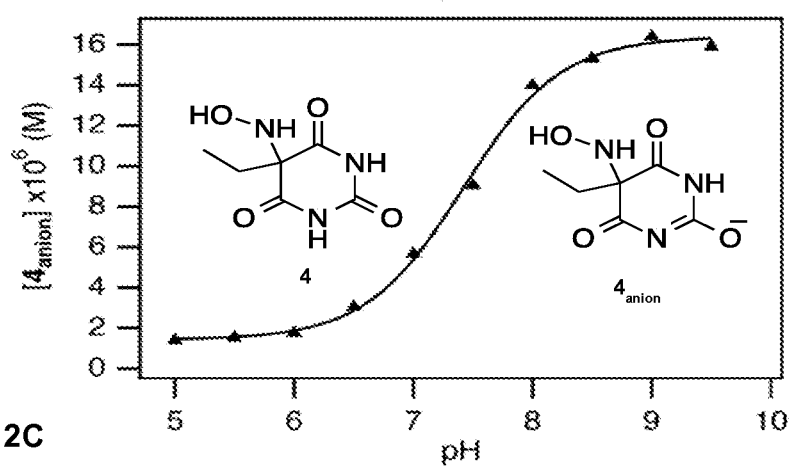
Figure 2C:
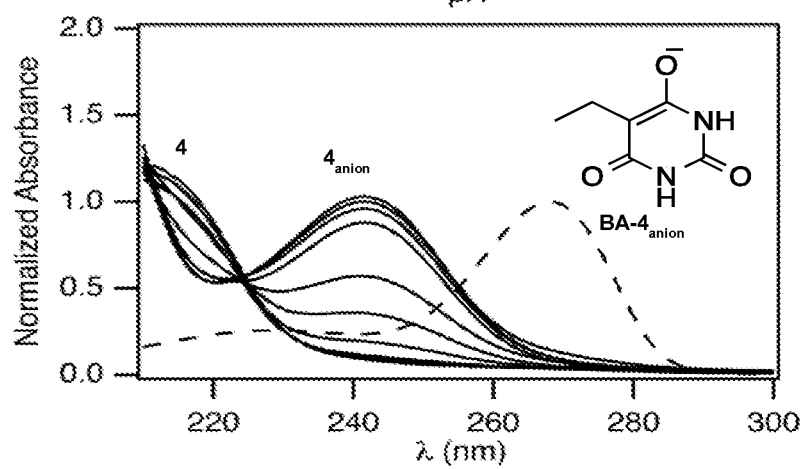

FIG. 2A shows a plot of UV-vis determined decomposition rates as a function of pH at 25° C. for three compounds of the disclosure (compound (1), compound (2), and compound (3)). FIG. 2B shows a plot of the concentration of compound (4) anion (λmax=242 nm) as a function of pH. FIG. 2C shows the initial UV-vis spectra of compound (4) from pH 5.0 to 9.5 compared with the expected byproduct of HNO release, compound (BA-4), at pH 9.5.

4. DETAILED DESCRIPTION

The invention includes the following:

(1.) An N-hydroxylaminobarbituric acid type compound, wherein said compound has a half-life of greater than about 10 minutes when measured under the conditions described in Example 17 or Example 18, provided that said compound is not 5-(N-hydroxylamino)-5-ethyl-N,N-dimethylbarbituric acid or 5-(N-hydroxylamino)-5-(acetyl-O-methyloxime)-N,N-dimethylbarbituric acid.

(2.) The N-hydroxylaminobarbituric acid type compound of the above (1.), wherein said compound has a half-life from about 10 minutes to about 200 minutes when measured under the conditions described in Example 18.

(3.) The N-hydroxylaminobarbituric acid type compound of the above (1.), wherein said compound has a half-life from about 12 minutes to about 190 minutes when measured under the conditions described in Example 18.

(4.) The N-hydroxylaminobarbituric acid type compound of the above (1.), wherein said compound has a half-life from about 10 minutes to about 4000 minutes when measured under the conditions described in Example 17.

(5.) The N-hydroxylaminobarbituric acid type compound of the above (1.), wherein said compound has a half-life from about 15 minutes to about 3900 minutes when measured under the conditions described in Example 17.

(6.) An N-hydroxylaminobarbituric acid type compound, wherein said compound produces a percent yield of HNO greater than about 50% when measured under the conditions described in Example 17, provided that said compound is not 5-(N-hydroxylamino)-5-ethyl-N,N-dimethylbarbituric acid or 5-(N-hydroxylamino)-5-(acetyl-O-methyloxime)-N,N-dimethylbarbituric acid.

(7.) The N-hydroxylaminobarbituric acid type compound of the above (6.), wherein said compound produces a percent yield of HNO from about 75% to about 100% when measured under the conditions described in Example 17.

(8.) The N-hydroxylaminobarbituric acid type compound of the above (6.), wherein said compound produces a percent yield of HNO from about 85% to about 100% when measured under the conditions described in Example 17.

(9.) An N-hydroxylaminobarbituric acid type compound, wherein said compound has a half-life of greater than about 10 minutes when measured under the conditions described in Example 17 or Example 18 and said compound produces a percent yield of HNO greater than about 50% when measured under the conditions described in Example 17, provided that said compound is not 5-(N-hydroxylamino)-5-ethyl-N,N-dimethylbarbituric acid or 5-(N-hydroxylamino)-5-(acetyl-O-methyloxime)-N,N-dimethylbarbituric acid.

(10.) The N-hydroxylaminobarbituric acid type compound of the above (9.), wherein said compound has a half-life from about 10 minutes to about 200 minutes when measured under the conditions described in Example 18 and said compound produces a percent yield of HNO from about 75% to about 100% when measured under the conditions described in Example 17.

(11.) The N-hydroxylaminobarbituric acid type compound of the above (9.), wherein said compound has a half-life from about 12 minutes to about 190 minutes when measured under the conditions described in Example 18 and wherein said compound produces a percent yield of HNO from about 85% to about 100% when measured under the conditions described in Example 17.

(12.) The N-hydroxylaminobarbituric acid type compound of the above (9.), wherein said compound has a half-life from about 10 minutes to about 4000 minutes when measured under the conditions described in Example 17 and said compound produces a percent yield of HNO from about 75% to about 100% when measured under the conditions described in Example 17.

(13.) The N-hydroxylaminobarbituric acid type compound of the above (9.), wherein said compound has a half-life from about 15 minutes to about 3900 minutes when measured under the conditions described in Example 17 and wherein said compound produces a percent yield of HNO from about 85% to about 100% when measured under the conditions described in Example 17.

(14.) A compound of formula (1):

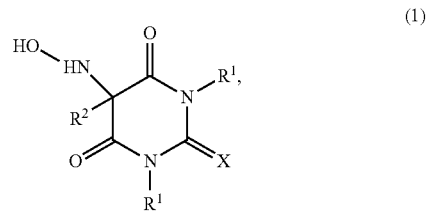

or a pharmaceutically acceptable salt thereof, wherein:
each $R^1$ is independently H or $(C_1)$alkyl;
$R^2$ is $(C_1-C_6)$alkyl substituted with a substituent selected from the group consisting of $(C_6-C_{14})$aryl, $(C_3-C_6)$cycloalkyl, $(C_5-C_7)$heterocycloalkyl, (5- or 6-membered)heteroaryl and (9- or 10-membered)heteroaryl, wherein said aryl, cycloalkyl, heterocycloalkyl and heteroaryl are unsubstituted or substituted with 1, 2, 3, 4 or 5 substituents selected from $R^4$ and said alkyl is unsubstituted or substituted with 1, 2 or 3 substituents selected from $R^6$;

X is O, $NR^7$ or S;

each $R^4$ is independently selected from the group consisting of halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl;

each $R^6$ is independently selected from the group consisting of halo and ($C_1$-$C_6$)alkyl; and $R^7$ is H or ($C_1$-$C_6$)alkyl.

(15.) The compound of the above (14.), wherein X is O or S;

(16.) The compound of the above (14.) or (15.), wherein at least one of $R^1$ is H.

(17.) The compound of the above (14.) or (15.), wherein at least one of $R^1$ is ($C_1$)alkyl.

(18.) The compound of any one of the above (14.)-(17.), wherein each $R^1$ is ($C_1$)alkyl.

(19.) The compound of any one of the above (14.) or (16.)-(18.), wherein X is O.

(20.) The compound of any one of the above (14.) or (16.)-(18.), wherein X is S.

(21.) The compound of any one of the above (14.) or (16.)-(18.), wherein X is NH.

(22.) The compound of any one of the above (14.)-(21.), wherein said compound has formula (1a):

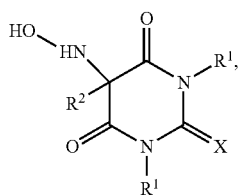

(1a)

or a pharmaceutically acceptable salt thereof, wherein:

$R^2$ is ($C_1$-$C_6$)alkyl substituted with ($C_6$-$C_{14}$)aryl, wherein said aryl is unsubstituted or substituted with 1, 2, 3, 4 or 5 substituents selected from $R^4$ and said alkyl is unsubstituted or substituted with 1, 2 or 3 substituents selected from $R^6$.

(23.) The compound of the above (22.), wherein $R^2$ is ($C_1$)alkyl substituted with ($C_6$-$C_{14}$)aryl, wherein said aryl is unsubstituted or substituted with 1, 2, 3, 4 or 5 substituents selected from $R^4$.

(24.) The compound of the above (22.) or (23.), wherein said aryl is phenyl.

(25.) The compound of any one of the above (22.)-(24.), wherein $R^4$ is ($C_1$-$C_6$)alkyl, —OH, ($C_1$-$C_3$)alkoxy, —S(O)O($C_1$-$C_6$)alkyl or halo.

(26.) The compound of the above (14.) or (15.), wherein said compound has formula (1a-1):

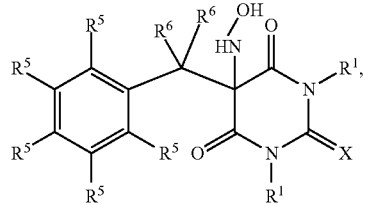

(1a-1)

or a pharmaceutically acceptable salt thereof, wherein:

each $R^1$ is ($C_1$)alkyl;

each $R^5$ is independently selected from the group consisting of H, halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl; and each $R^6$ is independently selected from the group consisting of H, halo and ($C_1$-$C_6$)alkyl.

(27.) The compound of the above (26.), wherein one or more of $R^5$ is selected from the group consisting of H, —OH, ($C_1$-$C_3$)alkoxy, S(O)O($C_1$-$C_6$)alkyl and halo.

(28.) The compound of the above (26.) or (27.), wherein one or more of $R^5$ is methoxy.

(29.) The compound of the above (26.) or (27.), wherein one or more of $R^5$ is Cl.

(30.) The compound of any one of the above (26.)-(29.), wherein at least one of $R^6$ is H.

(31.) The compound of any one of the above (26.)-(29.), wherein at least one of $R^6$ is halo.

(32.) The compound of any one of the above (26.)-(29.), wherein at least one of $R^6$ is methyl.

(33.) The compound of any one of the above (26.)-(32.), wherein X is O.

(34.) The compound of any one of the above (26.)-(32.), wherein X is S.

(35.) The compound of any one of the above (26.)-(32.), wherein X is NH.

(36.) The compound of the above (14.) or (15.), wherein said compound has formula (1a-2):

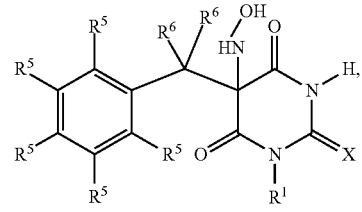

(1a-2)

or a pharmaceutically acceptable salt thereof, wherein:
R¹ is (C₁)alkyl;
each R⁵ is independently selected from the group consisting of H, halo, —OH, —NH₂, —C≡N, —NO₂, —SH, =O, =S, =N—(C₁-C₄)alkyl, (C₁-C₆)alkyl, (C₂-C₆)alkenyl, (C₂-C₆)alkynyl, (C₁-C₆)alkoxy, (C₂-C₆)alkenyloxy, (C₂-C₆)alkynyloxy, (C₆-C₁₄)aryl, (C₃-C₆)cycloalkyl, (5- or 6-membered)heteroaryl, (C₅-C₇)heterocycloalkyl, —C(O)H, —C(O)NH₂, —C(O)OH, —NH—C(O)—NH₂, —NH—C(S)—NH₂, —SC≡N, —SO₂NH₂, —COR', —C(O)OR', C(O)NHR', —C(O)NR'R", —NHR', —NR'R", —SR', —S(O)R', —S(O)OR', and —OR', wherein R' and R" are independently selected from (C₁-C₆)alkyl, (C₂-C₆)alkenyl, (C₂-C₆)alkynyl, (C₆-C₁₄)aryl, (C₃-C₆)cycloalkyl, (5- or 6-membered)heteroaryl and (C₅-C₇)heterocycloalkyl; and
each R⁶ is independently selected from the group consisting of H, halo and (C₁-C₆)alkyl.

(37.) The compound of the above (36.), wherein one or more of R⁵ is selected from the group consisting of H, —OH, (C₁-C₃)alkoxy, S(O)O(C₁-C₆)alkyl and halo.

(38.) The compound of the above (36.) or (37.), wherein one or more of R⁵ is methoxy.

(39.) The compound of the above (36.) or (37.), wherein one or more of R⁵ is Cl.

(40.) The compound of any one of the above (36.)-(39.), wherein at least one of R⁶ is H.

(41.) The compound of any one of the above (36.)-(39.), wherein at least one of R⁶ is halo.

(42.) The compound of any one of the above (36.)-(39.), wherein at least one of R⁶ is methyl.

(43.) The compound of any one of the above (36.)-(42.), wherein X is O.

(44.) The compound of any one of the above (36.)-(42.), wherein X is S.

(45.) The compound of any one of the above (36.)-(42.), wherein X is NH.

(46.) The compound of any one of the above (14.)-(21.), wherein said compound has formula (1b):

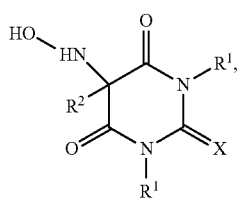

(1b)

or a pharmaceutically acceptable salt thereof, wherein:
each R¹ is independently H or (C₁)alkyl;
R² is (C₁-C₆)alkyl substituted with (C₃-C₆)cycloalkyl, wherein said heterocycloalkyl is unsubstituted or substituted with 1, 2 or 3 substituents selected from R⁴ and said alkyl is unsubstituted or substituted with 1, 2 or 3 substituents selected from R⁶;
each R⁴ is independently selected from the group consisting of halo, —OH, —NH₂, —C≡N, —NO₂, —SH, =O, =S, =N—(C₁-C₄)alkyl, (C₁-C₆)alkyl, (C₂-C₆)alkenyl, (C₂-C₆)alkynyl, (C₁-C₆)alkoxy, (C₂-C₆)alkenyloxy, (C₂-C₆)alkynyloxy, (C₆-C₁₄)aryl, (C₃-C₆)cycloalkyl, (5- or 6-membered)heteroaryl, (C₅-C₇)heterocycloalkyl, —C(O)H, —C(O)NH₂, —C(O)OH, —NH—C(O)—NH₂, —NH—C(S)—NH₂, —SC≡N, —SO₂NH₂, —COR', —C(O)OR', C(O)NHR', —C(O)NR'R", —NHR', —NR'R", —SR', —S(O)R', —S(O)OR', and —OR', wherein R' and R" are independently selected from (C₁-C₆)alkyl, (C₂-C₆)alkenyl, (C₂-C₆)alkynyl, (C₆-C₁₄)aryl, (C₃-C₆)cycloalkyl, (5- or 6-membered)heteroaryl and (C₅-C₇)heterocycloalkyl; and
each R⁶ is independently selected from the group consisting of halo and (C₁-C₆)alkyl.

(47.) The compound of the above (46.), wherein R² is (C₁)alkyl substituted with (C₃-C₆)cycloalkyl.

(48.) The compound of the above (46.) or (47.), wherein said (C₃-C₆)cycloalkyl is cyclohexyl.

(49.) The compound of any one of the above (14.)-(21.), wherein said compound has formula (1c):

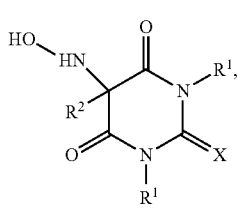

(1c)

or a pharmaceutically acceptable salt thereof, wherein:
R² is (C₁-C₆)alkyl substituted with (C₅-C₇)heterocycloalkyl, wherein said heterocycloalkyl is unsubstituted or substituted with 1, 2, 3, 4 or 5 substituents selected from R⁴ and said alkyl is unsubstituted or substituted with 1, 2 or 3 substituents selected from R⁶;
each R⁴ is independently selected from the group consisting of halo, —OH, —NH₂, —C≡N, —NO₂, —SH, =O, =S, =N—(C₁-C₄)alkyl, (C₁-C₆)alkyl, (C₂-C₆)alkenyl, (C₂-C₆)alkynyl, (C₁-C₆)alkoxy, (C₂-C₆)alkenyloxy, (C₂-C₆)alkynyloxy, (C₆-C₁₄)aryl, (C₃-C₆)cycloalkyl, (5- or 6-membered)heteroaryl, (C₅-C₇)heterocycloalkyl, —C(O)H, —C(O)NH₂, —C(O)OH, —NH—C(O)—NH₂, —NH—C(S)—NH₂, —SC≡N, —SO₂NH₂, —COR', —C(O)OR', C(O)NHR', —C(O)NR'R", —NHR', —NR'R", —SR', —S(O)R', —S(O)OR', and —OR', wherein R' and R" are independently selected from (C₁-C₆)alkyl, (C₂-C₆)alkenyl, (C₂-C₆)alkynyl, (C₆-C₁₄)aryl, (C₃-C₆)cycloalkyl, (5- or 6-membered)heteroaryl and (C₅-C₇)heterocycloalkyl; and
each R⁶ is independently selected from the group consisting of halo and (C₁-C₆)alkyl.

(50.) The compound of the above (49.), wherein R² is (C₁)alkyl substituted with (C₅-C₇)heterocycloalkyl.

(51.) The compound of any one of the above (14.)-(21.), wherein said compound has formula (1d):

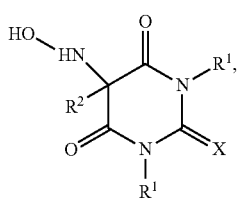

(1d)

or a pharmaceutically acceptable salt thereof, wherein:
R² is (C₁-C₆)alkyl substituted with (5- or 6-membered)heteroaryl or (9- or 10-membered)heteroaryl, wherein said heteroaryl is unsubstituted or substituted with 1, 2, 3, 4 or 5 substituents selected from $R^4$ and said alkyl is unsubstituted or substituted with 1, 2 or 3 substituents selected from $R^6$;

each $R^4$ is independently selected from the group consisting of halo, —OH, —NH$_2$, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_5$-C$_7$)heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_5$-C$_7$)heterocycloalkyl; and each $R^6$ is independently selected from the group consisting of halo and (C$_1$-C$_6$)alkyl.

(52.) The compound of the above (51.), wherein $R^2$ is (C$_1$)alkyl substituted with (5- or 6-membered)heteroaryl or (9- or 10-membered)heteroaryl.

(53.) The compound of the above (51.) or (52.), wherein said heteroaryl is selected from the group consisting of furyl, thienyl, pyridyl, pyridazinyl, pyrimidyl, pyrazinyl, 1,3,5-triazinyl, thiophenyl, and benzo[d][1,3]dioxolyl.

(54.) The compound of the above (14.) having the formula:

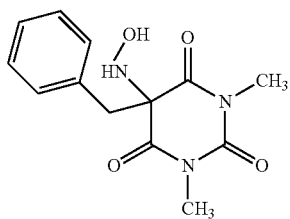

or a pharmaceutically acceptable salt thereof.

(55.) The compound of the above (14.) having the formula:

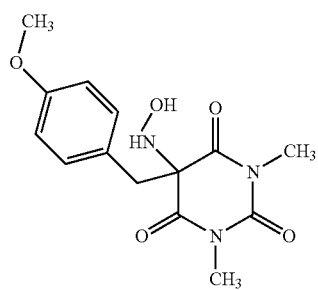

or a pharmaceutically acceptable salt thereof.

(56.) The compound of the above (14.) having the formula:

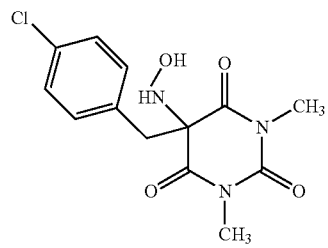

or a pharmaceutically acceptable salt thereof.

(57.) A compound of formula (2):

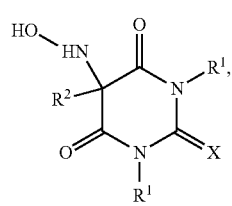

or a pharmaceutically acceptable salt thereof, wherein:

each $R^1$ is independently H or (C$_1$)alkyl;

$R^2$ is selected from the group consisting of a branched C$_3$-C$_6$ alkyl, a branched C$_3$-C$_6$ alkenyl, and a branched C$_3$-C$_6$ alkoxy, wherein said alkyl, alkenyl, and alkoxy are unsubstituted or substituted with 1, 2 or 3 substituents selected from $R^4$;

X is O, NR$^7$ or S;

each $R^4$ is independently selected from the group consisting of halo, —OH, —NH$_2$, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_5$-C$_7$)heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_5$-C$_7$)heterocycloalkyl; and $R^7$ is H or (C$_1$-C$_6$)alkyl.

(58.) The compound of the above (57.), wherein X is O or S.

(59.) The compound of the above (57.) or (58.), wherein at least one of $R^1$ is H.

(60.) The compound of the above (57.) or (58.), wherein at least one of $R^1$ is (C$_1$)alkyl.

(61.) The compound of any one of the above (57.)-(60.), wherein each $R^1$ is methyl.

(62.) The compound of any one of the above (57.)-(61.), wherein $R^2$ is selected from the group consisting of iso-propyl, methylpropyl, sec-butyl, iso-butyl, tert-butyl, methylbutyl, iso-pentyl, methylpentyl, ethylbutyl, dimethylbutyl, and iso-propylpropyl.

(63.) The compound of any one of the above (57.) or (59.)-(62.), wherein X is O.

(64.) The compound of any one of the above (57.) or (59.)-(62.), wherein X is S.

(65.) The compound of any one of the above (57.) or (59.)-(62.), wherein X is NH.

(66.) A compound of formula (3):

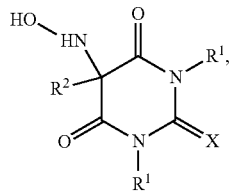

(3)

or a pharmaceutically acceptable salt thereof, wherein:

each $R^1$ is H;

$R^2$ is selected from the group consisting of $(C_1-C_6)$alkyl, $(C_2-C_6)$alkenyl, $(C_2-C_6)$alkynyl and $(C_1-C_6)$alkoxy, wherein said alkyl, alkenyl, alkynyl and alkoxy are unsubstituted or substituted with 1, 2 or 3 substituents selected from $R^4$;

X is O, $NR^7$ or S;

each $R^4$ is independently selected from the group consisting of halo, —OH, —CH$_2$OH, —NH$_2$, —C≡N, —NO$_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(NH)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl; and $R^7$ is H or $(C_1-C_6)$alkyl.

(67.) The compound of the above (66.), wherein X is O or S.

(68.) The compound of the above (66.) or (67.), wherein $R^2$ is $(C_1-C_6)$alkyl, wherein said alkyl is unsubstituted or substituted with 1, 2 or 3 substituents selected from $R^4$.

(69.) The compound of the above (66.)-(68.), wherein $R^2$ is methyl, ethyl, propylene, iso-propyl, methylbutyl, methylpropyl, iso-pentyl or trifluoroethyl.

(70.) The compound of the above (66.) or (67.), wherein $R^2$ is selected from the group consisting of a branched $(C_3-C_6)$alkyl, branched $(C_3-C_6)$alkenyl, and branched $(C_3-C_6)$alkoxy, wherein said alkyl, alkenyl, and alkoxy are unsubstituted or substituted with 1, 2 or 3 substituents selected from $R^4$.

(71.) The compound of any one of the above (66.) or (68.)-(70.), wherein X is O.

(72.) The compound of any one of the above (66.) or (68.)-(70.), wherein X is S.

(73.) The compound of any one of the above (66.) or (68.)-(70.), wherein X is NH.

(74.) The compound of the above (66.) or (67.), wherein said compound has formula (3a):

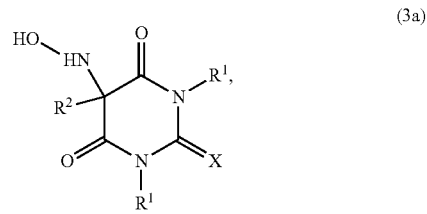

(3a)

or a pharmaceutically acceptable salt thereof, wherein:

$R^2$ is $(C_1-C_4)$alkyl substituted with phenyl, wherein said phenyl is unsubstituted or substituted with 1, 2, 3, 4 or 5 substituents selected from $R^4$ and said alkyl is unsubstituted or substituted with 1, 2 or 3 substituents selected from $R^6$;

each $R^4$ is independently selected from the group consisting of halo, —OH, —NH$_2$, —C≡N, —NO$_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl; and each $R^6$ is independently selected from the group consisting of halo, —S(O)O$(C_1-C_6)$alkyl and $(C_1-C_6)$alkyl.

(75.) The compound of the above (74.), wherein $R^2$ is $(C_1)$alkyl substituted with phenyl.

(76.) The compound of the above (74.) or (75.), wherein $R^4$ is $(C_1-C_3)$alkoxy or halo.

(77.) The compound of any one of the above (74.)-(76.), wherein X is O.

(78.) The compound of any one of the above (74.)-(76.), wherein X is S.

(79.) The compound of any one of the above (74.)-(76.), wherein X is NH.

(80.) The compound of the above (66.) or (67.), wherein said compound has formula (3a-1):

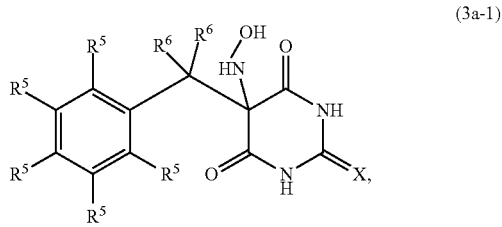

(3a-1)

or a pharmaceutically acceptable salt thereof, wherein:

each $R^5$ is selected from the group consisting of H, halo, —OH, —NH$_2$, —C≡N, —NO$_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl; and each $R^6$ is independently selected from the group consisting of H, halo and $(C_1-C_6)$alkyl.

(81.) The compound of the above (80), wherein one or more of $R^5$ is selected from the group consisting of H, —OH, $(C_1-C_3)$alkoxy, —S(O)O($C_1-C_6$)alkyl and halo.

(82.) The compound of the above (80.) or (81.), wherein one or more of $R^5$ is methoxy.

(83.) The compound of the above (80.) or (81.), wherein one or more of $R^5$ is Cl.

(84.) The compound of any one of the above (80.)-(83.), wherein at least one of $R^6$ is H.

(85.) The compound of any one of the above (80.)-(83.), wherein at least one of $R^6$ is halo.

(86.) The compound of any one of the above (80.)-(83.), wherein at least one of $R^6$ is methyl.

(87.) The compound of any one of the above (80.)-(86.), wherein X is O.

(88.) The compound of any one of the above (80.)-(86.), wherein X is S.

(89.) The compound of any one of the above (80.)-(86.), wherein X is NH.

(90.) The compound of the above (66.) or (67.), wherein said compound has formula (3b):

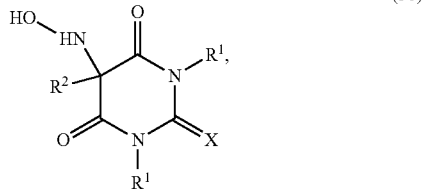

(3b)

or a pharmaceutically acceptable salt thereof, wherein:
$R^2$ is $(C_1-C_4)$alkyl substituted with $(C_3-C_6)$cycloalkyl, wherein said cycloalkyl is unsubstituted or substituted with 1, 2 or 3 substituents selected from $R^4$ and said alkyl is unsubstituted or substituted with 1, 2 or 3 substituents selected from $R^6$;

each $R^4$ is independently selected from the group consisting of halo, —OH, —NH$_2$, —C≡N, —NO$_2$, —SH, =O, =S, =N—($C_1-C_4$)alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl; and each $R^6$ is independently selected from the group consisting of halo and $(C_1-C_6)$alkyl.

(91.) The compound of the above (90.), wherein $R^2$ is $(C_1)$alkyl substituted with $(C_3-C_6)$cycloalkyl.

(92.) The compound of the above (90.) or (91.), wherein said $(C_3-C_6)$cycloalkyl is cyclohexyl.

(93.) The compound of any one of the above (90.)-(92.), wherein X is O.

(94.) The compound of any one of the above (90.)-(92.), wherein X is S.

(95.) The compound of any one of the above (90.)-(92.), wherein X is NH.

(96.) The compound of the above (66.) or (67.), wherein said compound has formula (3c):

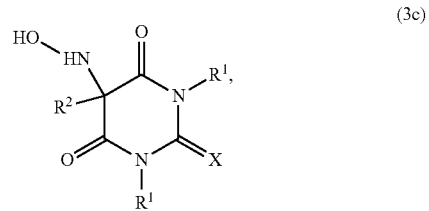

(3c)

or a pharmaceutically acceptable salt thereof, wherein:
$R^2$ is $(C_1-C_4)$alkyl substituted with $(C_5-C_7)$heterocycloalkyl, wherein said heterocycloalkyl is unsubstituted or substituted with 1, 2, 3, 4 or 5 substituents selected from $R^4$ and said alkyl is unsubstituted or substituted with 1, 2 or 3 substituents selected from $R^6$;

each $R^4$ is independently selected from the group consisting of halo, —OH, —NH$_2$, —C≡N, —NO$_2$, —SH, =O, =S, =N—($C_1-C_4$)alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl; and each $R^6$ is independently selected from the group consisting of halo and $(C_1-C_6)$alkyl.

(97.) The compound of the above (96.), wherein $R^2$ is $(C_1)$alkyl substituted with $(C_5-C_7)$heterocycloalkyl.

(98.) The compound of the above (96.) or (97.), wherein said heterocycloalkyl is a $(C_6)$heterocycloalkyl selected from the group consisting of piperidinyl, piperazinyl, tetrahydro-oxazinyl, tetrahydropyran, dioxane, morpholine and thiomorpholine.

(99.) The compound of any one of the above (96.)-(98.), wherein X is O.

(100.) The compound of any one of the above (96.)-(98.), wherein X is S.

(101.) The compound of any one of the above (96.)-(98.), wherein X is NH.

(102.) The compound of the above (66.) or (67.), wherein said compound has formula (3d):

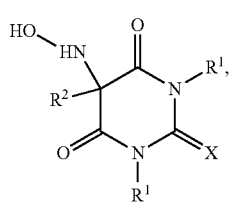

(3d)

or a pharmaceutically acceptable salt thereof, wherein:
R² is (C₁-C₄)alkyl substituted with (5- or 6-membered)heteroaryl or (9- or 10-membered)heteroaryl, wherein said heteroaryl is unsubstituted or substituted with 1, 2, 3, 4 or 5 substituents selected from R⁴ and said alkyl is unsubstituted or substituted with 1, 2 or 3 substituents selected from R⁶;
each R⁴ is independently selected from the group consisting of halo, —OH, —CH₂OH, —NH₂, —C≡N, —NO₂, —SH, =O, =S, =N—(C₁-C₄)alkyl, (C₁-C₆)alkyl, (C₂-C₆)alkenyl, (C₂-C₆)alkynyl, (C₁-C₆)alkoxy, (C₂-C₆)alkenyloxy, (C₂-C₆)alkynyloxy, (C₆-C₁₄)aryl, (C₃-C₆)cycloalkyl, (5- or 6-membered)heteroaryl, (C₅-C₇)heterocycloalkyl, —C(O)H, —C(O)NH₂, —C(O)OH, —NH—C(O)—NH₂, —NH—C(S)—NH₂, —SC≡N, —SO₂NH₂, —COR', —C(O)OR', C(O)NHR', —C(O)NR'R", —NHR', —NR'R", —SR', —S(O)R', —S(O)OR', and —OR', wherein R' and R" are independently selected from (C₁-C₆)alkyl, (C₂-C₆)alkenyl, (C₂-C₆)alkynyl, (C₆-C₁₄)aryl, (C₃-C₆)cycloalkyl, (5- or 6-membered)heteroaryl and (C₅-C₇)heterocycloalkyl; and
each R⁶ is independently selected from the group consisting of halo and (C₁-C₆)alkyl.

(103.) The compound of the above (102.), wherein R² is (C₁)alkyl substituted with (5- or 6-membered)heteroaryl or (9- or 10-membered)heteroaryl.

(104.) The compound of the above (102.) or (103.), wherein said heteroaryl is selected from the group consisting of furyl, thienyl, imidazolyl, pyridyl, pyridazinyl, pyrimidyl, pyrazinyl, 1,3,5-triazinyl, thiophenyl, 1H-indolyl, 3H-indolyl and benzo[d][1,3]dioxolyl.

(105.) The compound of any one of the above (102.)-(104.), wherein X is O.

(106.) The compound of any one of the above (102.)-(104.), wherein X is S.

(107.) The compound of any one of the above (102.)-(104.), wherein X is NH.

(108.) The compound of the above (66.) having the formula:

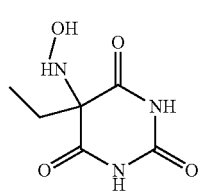

4 or a pharmaceutically acceptable salt thereof.

(109.) The compound of the above (66.) having the formula:

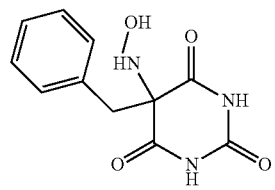

5 or a pharmaceutically acceptable salt thereof.

(110.) The compound of the above (66.) having the formula:

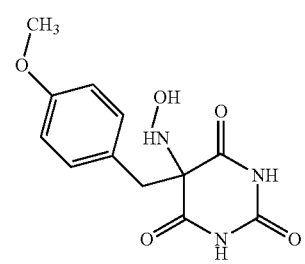

6 or a pharmaceutically acceptable salt thereof.

(111.) The compound of the above (66.) having the formula:

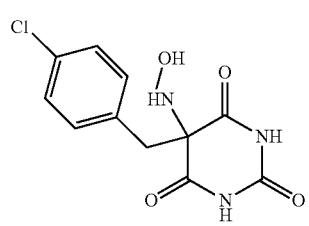

7 or a pharmaceutically acceptable salt thereof.

(112.) A compound of formula (4):

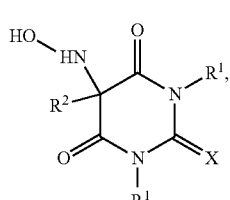

(4)

or a pharmaceutically acceptable salt thereof, wherein:
each R¹ is independently H or (C₁)alkyl;
R² is (C₆-C₁₀)aryl, (C₃-C₆)cycloalkyl, (C₅-C₇)heterocycloalkyl and (5- or 6-membered)heteroaryl, wherein said aryl, cycloalkyl, heterocycloalkyl and heteroaryl are unsubstituted or substituted with 1, 2, 3, 4 or 5 substituents selected from R⁴;
X is O, NR⁷ or S;
each R⁴ is independently selected from the group consisting of halo, —OH, —NH₂, —C≡N, —NO₂, —SH, =O, =S, =N—(C₁-C₄)alkyl, (C₁-C₆)alkyl, (C₂-C₆)

alkenyl, $(C_2\text{-}C_6)$alkynyl, $(C_1\text{-}C_6)$alkoxy, $(C_2\text{-}C_6)$alkenyloxy, $(C_2\text{-}C_6)$alkynyloxy, $(C_6\text{-}C_{14})$aryl, $(C_3\text{-}C_6)$cycloalkyl, (5- or 6-membered)heteroaryl, $(C_5\text{-}C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1\text{-}C_6)$alkyl, $(C_2\text{-}C_6)$alkenyl, $(C_2\text{-}C_6)$alkynyl, $(C_6\text{-}C_{14})$aryl, $(C_3\text{-}C_6)$cycloalkyl, (5- or 6-membered)heteroaryl and $(C_5\text{-}C_7)$heterocycloalkyl; and R$^7$ is H or $(C_1\text{-}C_6)$alkyl.

(113.) The compound of the above (112.), wherein at least one of R$^1$ is H.

(114.) The compound of the above (112.), wherein at least one of R$^1$ is $(C_1)$alkyl.

(115.) The compound of the above (112.), wherein each R$^1$ is $(C_1)$alkyl.

(116.) The compound of any one of the above (112.)-(115.), wherein X is O.

(117.) The compound of any one of the above (112.)-(115.), wherein X is S.

(118.) The compound of any one of the above (112.)-(115.), wherein X is NH.

(119.) The compound of any one of the above (112.)-(118.), wherein said compound has formula (4a):

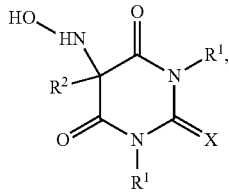

(4a)

or a pharmaceutically acceptable salt thereof, wherein:
R$^2$ is $(C_6\text{-}C_{10})$aryl, wherein said aryl is unsubstituted or substituted with 1, 2, 3, 4 or 5 substituents selected from R$^4$.

(120). The compound of the above (119.), wherein:
R$^2$ is phenyl unsubstituted or substituted with 1, 2, 3, 4 or 5 substituents selected from R$^4$.

(121.) The compound of the above (120.), wherein:
R$^2$ is unsubstituted phenyl.

(122.) The compound of any one of the above (112.)-(118.), wherein said compound has formula (4b):

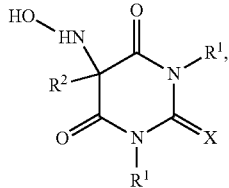

(4b)

or a pharmaceutically acceptable salt thereof, wherein:
R$^2$ is $(C_3\text{-}C_6)$cycloalkyl, wherein said cycloalkyl is unsubstituted or substituted with 1, 2, 3, 4 or 5 substituents selected from R$^4$.

(123.) The compound of the above (122.), wherein R$^2$ is cyclohexyl.

(124.) The compound of any one of the above (112.)-(118.), wherein said compound has formula (4c):

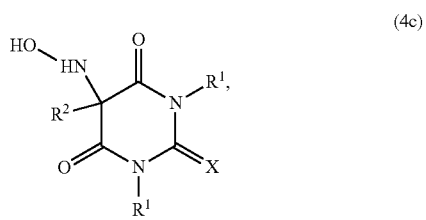

(4c)

or a pharmaceutically acceptable salt thereof, wherein:
R$^2$ is $(C_5\text{-}C_7)$heterocycloalkyl, wherein said heterocycloalkyl is unsubstituted or substituted with 1, 2, 3, 4 or 5 substituents selected from R$^4$.

(125.) The compound of the above (124.), wherein R$^2$ is $(C_6)$heterocycloalkyl.

(126.) The compound of any one of the above (112.)-(118.), wherein said compound has formula (4d):

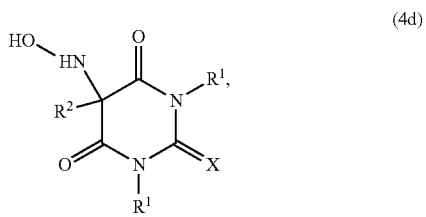

(4d)

or a pharmaceutically acceptable salt thereof, wherein:
R$^2$ is (5- or 6-membered)heteroaryl, wherein said heteroaryl is unsubstituted or substituted with 1, 2, 3, 4 or 5 substituents selected from R$^4$.

(127.) A compound of formula (5):

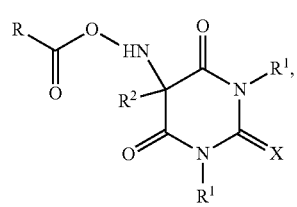

(5)

or a pharmaceutically acceptable salt thereof, wherein:
R$^1$, R$^2$ and X are as defined in the above (10.)-(122.); and
R is hydrogen, —$(C_1\text{-}C_6)$alkyl, —$(C_2\text{-}C_4)$alkenyl, phenyl, benzyl, cyclopentyl, cyclohexyl, —$(C_5\text{-}C_7)$heterocycloalkyl, benzyloxy, —O—$(C_1\text{-}C_6)$alkyl, —NH$_2$, —NH—$(C_1\text{-}C_4)$alkyl, or —N($(C_1\text{-}C_4)$alkyl)$_2$, wherein said —$(C_1\text{-}C_6)$alkyl, —$(C_2\text{-}C_4)$alkenyl, phenyl, benzyl, cyclopentyl, cyclohexyl, —$(C_5\text{-}C_7)$heterocycloalkyl, benzyloxy, —O—$(C_1\text{-}C_6)$alkyl, —NH—$(C_1\text{-}C_4)$alkyl, or —N($(C_1\text{-}C_4)$alkyl)$_2$ can be unsubstituted or substituted with 1, 2 or 3 substituents selected from halo, —$(C_1\text{-}C_6)$alkyl, —$(C_2\text{-}C_4)$alkenyl, —$(C_2\text{-}C_3)$alkynyl, -(5- or 6-membered)heteroaryl, —O—$(C_1\text{-}C_6)$alkyl, —S—$(C_1\text{-}C_6)$alkyl, —C(halo)$_3$, —CH(halo)$_2$, —CH$_2$(halo), —CN, —NO$_2$, —NH$_2$, —NH—$(C_1\text{-}C_4)$alkyl, —N(—$(C_1\text{-}C_4)$alkyl)$_2$, —C(O)$(C_1\text{-}C_4)$alkyl, —C(O)O $(C_1\text{-}C_4)$alkyl, —OC(O)$(C_1\text{-}C_4)$alkyl, —OC(O)NH$_2$, —S(O)$(C_1\text{-}C_4)$alkyl, or —S(O)$_2$$(C_1\text{-}C_4)$alkyl.

(128.) A compound selected from:
5-(N-hydroxylamino)-5-benzyl-N,N-dimethylbarbituric acid;
5-(N-hydroxylamino)-5-(4-methoxybenzyl)-N,N-dimethylbarbituric acid;
5-(N-hydroxylamino)-5-(4-chlorobenzyl)-N,N-dimethylbarbituric acid;
5-(N-hydroxylamino)-5-ethyl-barbituric acid;
5-(N-hydroxylamino)-5-benzyl-barbituric acid;
5-(N-hydroxylamino)-5-(4-methoxybenzyl)-barbituric acid;
5-(N-hydroxylamino)-5-(4-chlorobenzyl)-barbituric acid;
5-(N-hydroxylamino)-5-phenyl-barbituric acid;
5-(N-hydroxylamino)-5-(2-propen-1-yl)-barbituric acid;
5-(N-hydroxylamino)-5-(2-methylpropyl)-barbituric acid;
5-(N-hydroxylamino)-5-(1-methylethyl)-barbituric acid;
5-(N-hydroxylamino)-5-(1-methylbutyl)-barbituric acid;
5-(N-hydroxylamino)-5-phenyl-thiobarbituric acid;
5-(N-hydroxylamino)-5-(2-chlorobenzyl)-barbituric acid;
5-(N-hydroxylamino)-5-(2-furylmethyl)-barbituric acid;
5-(N-hydroxylamino)-5-(2-thienylmethyl)-barbituric acid;
5-(N-hydroxylamino)-5-methyl-barbituric acid;
5-(N-hydroxylamino)-5-(1-methylpropyl)-barbituric acid;
5-(hydroxylamino)-5-(3-methylbutyl) barbituric acid;
5-(hydroxyamino)-2-imino-5-phenyldihydropyrimidine-4,6(1H,5H)-dione;
5-(hydroxylamino)-5-(2,2,2-trifluoroethyl) barbituric acid;
5-(hydroxylamino)-5-(4-(methylsulfonyl)benzyl)barbituric acid
5-(hydroxylamino)-5-(benzo[d][1,3]dioxol-5-ylmethyl)barbituric acid;
5-(hydroxylamino)-5-(pyridin-4-ylmethyl)barbituric acid;
5-(hydroxylamino)-5-(3-ethyl-5-hydroxy-6-methylpyridin-4-ylmethyl)barbituric acid;
5-(hydroxylamino)-5-(3-hydroxy-5-(hydroxylmethyl)-2-methylpyridin-4-ylmethyl)barbituric acid;
5-(hydroxylamino)5-(2-(methylthio)ethyl)barbituric acid;
5-(hydroxyamino)-5-(4-hydroxybenzyl)barbituric acid;
5-((1H-indol-2-yl)methyl)-5-(hydroxyamino)barbituric acid;
2-(5-(hydroxyamino)-2,4,6-trioxohexahydropyrimidin-5-yl) acetic acid;
3-(5-(hydroxyamino)-2,4,6-trioxohexahydropyrimidin-5-yl) propanoic acid
2-(5-(hydroxyamino)-2,4,6-trioxohexahydropyrimidin-5-yl) acetamide;
3-(5-(hydroxyamino)-2,4,6-trioxohexahydropyrimidin-5-yl) propanamide;
5-((1H-imidazol-5-yl)methyl)-5-(hydroxyamino)barbituric acid;
5-(4-aminobutyl)-5-(hydroxyamino)barbituric acid;
1-(3-(5-(hydroxyamino)-2,4,6-trioxohexahydropyrimidin-5-yl)propyl)guanidine;
5-(hydroxylamino)5-(2-(methylthio)ethyl)barbituric acid;
5-(hydroxyamino)-5-(4-hydroxybenzyl)barbituric acid;
5-((1H-indol-2-yl)methyl)-5-(hydroxyamino)barbituric acid;
2-(5-(hydroxyamino)-2,4,6-trioxohexahydropyrimidin-5-yl) acetic acid;
3-(5-(hydroxyamino)-2,4,6-trioxohexahydropyrimidin-5-yl) propanoic acid
2-(5-(hydroxyamino)-2,4,6-trioxohexahydropyrimidin-5-yl) acetamide;
3-(5-(hydroxyamino)-2,4,6-trioxohexahydropyrimidin-5-yl) propanamide;
5-((1H-imidazol-5-yl)methyl)-5-(hydroxyamino)barbituric acid;
5-(4-aminobutyl)-5-(hydroxyamino)barbituric acid; and
1-(3-(5-(hydroxyamino)-2,4,6-trioxohexahydropyrimidin-5-yl)propyl)guanidine.

(129.) A pharmaceutical composition comprising the compound of any one of the above (1.)-(128.) and at least one pharmaceutically acceptable excipient.

(130.) The pharmaceutical composition of the above (129.), wherein said pharmaceutical composition is suitable for intravenous administration.

(131.) A method of treating a cardiovascular disease, comprising administering an effective amount of the compound of any one of the above (1.)-(128.) or the pharmaceutical composition of the above (129.) or (130.) to a patient in need thereof.

(132.) The method of the above (131.), wherein said cardiovascular disease is heart failure.

(133.) The method of the above (131.), wherein said cardiovascular disease is acute decompensated heart failure.

(134.) The method of any one of the above (131.)-(133.), wherein said compound is administered intravenously.

(135.) Use of a pharmaceutical composition of the above (129.) or (130.) for the manufacture of a medicament useful for treating a cardiovascular disease.

(136.) Use of a pharmaceutical composition of the above (129.) or (130.) for the manufacture of a medicament useful for treating heart failure.

(137.) Use of a pharmaceutical composition of the above (129.) or (130.) for the manufacture of a medicament useful for treating acute decompensated heart failure.

(138.) The pharmaceutical composition of the above (129.) or (130.) for use in the treatment of heart failure.

(139.) The pharmaceutical composition of the above (129.) or (130.) for use in the treatment of acute decompensated heart failure.

4.1 Definitions

In order that the present disclosure may be more readily understood, certain terms are first defined. Additional terms are defined throughout the detailed description.

A "pharmaceutically acceptable salt" refers to a salt of any therapeutic agent disclosed herein, which salt can include any of a variety of organic and inorganic counter ions known in the art and which salt is pharmaceutically acceptable. When the therapeutic agent contains an acidic functionality, various exemplary embodiments of counter ions are sodium, potassium, calcium, magnesium, ammonium, tetraalkylammonium, and the like. When the therapeutic agent contains a basic functionality, a pharmaceutically acceptable salt can include as a counter ion, by way of example, an organic or inorganic acid, such as hydrochloride, hydrobromide, tartrate, mesylate, acetate, maleate, oxalate, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt can be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower-alkyl amines), such as mono-, bis-, or tris-(2-hydroxyethyl)amine, 2-hydroxy-tert-butylamine, or tris-(hydroxymethyl)methylamine, N,N-di-lower-alkyl-N-(hydroxy-lower-alkyl)-amines, such as N,N-dimethyl-N-(2-hydroxyethyl) amine, or tri-(2-hydroxyethyl)amine; N-methyl-D-glucamine; and amino acids such as arginine, lysine, and the like. A salt can also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Gennaro, Ed., *Remington: The Science and Practice of Pharmacy*, 20$^{th}$ Ed. (Lippincott Williams & Wilkins, Baltimore, Md., 2000) and *Handbook of Pharmaceutical Excipients*, American Pharmaceutical Association, Washington, D.C., (e.g., 1$^{st}$, 2$^{nd}$ and 3$^{rd}$ Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Unit dosage form" refers to a physically discrete unit suitable as a unitary dosage for a human or an animal Each unit dosage form can contain a predetermined amount of a therapeutic agent calculated to produce a desired effect.

Unless clearly indicated otherwise, a "patient" refers to an animal, such as a mammal, including but not limited to, a human. Hence, the methods disclosed herein can be useful in human therapy and veterinary applications. In particular embodiments, the patient is a mammal. In certain embodiments, the patient is a human.

"Effective amount" refers to such amount of a therapeutic agent or a pharmaceutically acceptable salt thereof, which in combination with its parameters of efficacy and potential for toxicity, as well as based on the knowledge of the practicing specialist, should be effective in a given therapeutic form. As is understood in the art, an effective amount can be administered in one or more doses.

"Treatment", "treating" and the like is an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prevent", "preventing" and the like refers to reducing the probability of developing a condition in a patient who does not have, but is at risk of developing a condition. A patient "at risk" may or may not have a detectable condition, and may or may not have displayed a detectable condition prior to the treatment methods disclosed herein. "At risk" denotes that a patient has one or more so-called risk factors, which are measurable parameters that correlate with development of a condition and are known in the art. A patient having one or more of these risk factors has a higher probability of developing the condition than a patient without such risk factor(s).

"Positive inotrope" refers to an agent that causes an increase in myocardial contractile function. Exemplary positive inotropes are a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also intended. For example, U.S. Pat. No. 4,663,351 discloses a dobutamine prodrug that can be administered orally.

A condition that is "responsive to nitroxyl therapy" includes any condition in which administration of a compound that donates an effective amount of nitroxyl under physiological conditions treats and/or prevents the condition, as those terms are defined herein. A condition whose symptoms are suppressed or diminished upon administration of nitroxyl donor is a condition responsive to nitroxyl therapy.

"Pulmonary hypertension" or "PH" refers to a condition in which the pulmonary arterial pressure is elevated. The current hemodynamic definition of PH is a mean pulmonary arterial pressure (MPAP) at rest of greater than or equal to 25 mmHg Badesch et al., *J. Amer. Coll. Cardiol.* 54(Suppl.): S55-S66 (2009).

"($C_1$-$C_6$)alkyl" refers to saturated linear and branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl.

Examples of $(C_1-C_6)$alkyl groups include methyl, ethyl, n-propyl, iso-propyl, n-butyl, tert-butyl, n-hexyl, and the like.

"$(C_2-C_6)$alkyl" refers to saturated linear and branched hydrocarbon structures having 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_2-C_6)$alkyl groups include ethyl, n-propyl, iso-propyl, n-butyl, tert-butyl, n-hexyl, and the like.

"$(C_1-C_4)$alkyl" refers to saturated linear and branched hydrocarbon structures having 1, 2, 3, or 4 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_4)$alkyl groups include methyl, ethyl, n-propyl, iso-propyl, n-butyl, tert-butyl, and the like.

"$(C_1-C_2)$alkyl" refers to saturated linear and branched hydrocarbon structures having 1 or 2 carbon atoms. Examples of $(C_1-C_2)$alkyl groups include methyl and ethyl.

"$(C_3-C_6)$alkyl" refers to saturated linear and branched hydrocarbon structures having 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_3-C_5)$alkyl groups include n-propyl, iso-propyl, n-butyl, tert-butyl, n-pentyl, n-hexyl and the like.

"Branched $(C_3-C_6)$alkyl" refers to saturated branched hydrocarbon structures having 3, 4, 5, or 6 carbon atoms. Examples of branched $(C_3-C_6)$alkyl groups include iso-propyl, tert-butyl, 2,3-dimethylbutyl, 2-methylpentyl, 3-methylpentyl, and the like.

"$(C_2-C_6)$alkenyl" refers to a straight-chain or branched unsaturated hydrocarbon radical having 2, 3, 4, 5 or 6 carbon atoms and a double bond in any position, e.g., ethenyl, 1-propenyl, 2-propenyl (allyl), 1-butenyl, 2-butenyl, 3-butenyl, 1-methylethenyl, 1-methyl-1-propenyl, 2-methyl-2-propenyl, 2-methyl-1-propenyl, 1-methyl-2-propenyl, 1-hexenyl, 2-hexenyl, 3-hexenyl, 2-methyl-2-pentenyl, 4-methyl-2-pentenyl, 4-methyl-1-pentenyl, 3-methyl-1-pentenyl, and the like.

"$(C_2-C_4)$alkenyl" refers to a straight-chain or branched unsaturated hydrocarbon radical having 2, 3, or 4 carbon atoms and a double bond in any position, e.g., ethenyl, 1-propenyl, 2-propenyl (allyl), 1-butenyl, 2-butenyl, 3-butenyl, 1-methylethenyl, 1-methyl-1-propenyl, 2-methyl-2-propenyl, 2-methyl-1-propenyl, 1-methyl-2-propenyl, and the like.

"Branched $(C_3-C_6)$alkenyl" refers to a branched unsaturated hydrocarbon radical having 3, 4, 5 or 6 carbon atoms and a double bond in any position, e.g., 1-methylethenyl, 1-methyl-1-propenyl, 2-methyl-2-propenyl, 2-methyl-1-propenyl, 1-methyl-2-propenyl, and the like.

"$(C_2-C_6)$alkynyl" refers to a straight chain or branched hydrocarbon having 2, 3, 4, 5 or 6 carbon atoms and including at least one carbon-carbon triple bond. Examples of $(C_2-C_6)$alkynyls include ethynyl, propynyl, 1-butyryl, 2-butyryl, 1-pentynyl, 2-pentynyl, 1-hexynyl, 2-hexynyl, 3-hexynyl, 4-methyl-2-pentynyl and the like.

"$(C_2-C_3)$alkynyl" refers to a straight chain hydrocarbon having 2 or 3 carbon atoms and including at least one carbon-carbon triple bond. Examples of $(C_2-C_3)$alkynyls include ethynyl and propynyl.

"$(C_3-C_6)$cycloalkyl" refers to a saturated cyclic hydrocarbon containing 3, 4, 5 or 6 ring carbon atoms. Examples of $(C_3-C_6)$cycloalkyl groups include cyclopropyl, cyclobutyl, cyclopentyl, cyclohexyl, and the like.

"$(C_1-C_6)$alkoxy" refers to —O—$(C_1-C_6)$alkyl. Examples of $(C_1-C_6)$alkoxy groups include methoxy, ethoxy, propoxy, n-propoxy, iso-propoxy, butoxy, n-butoxy, sec-butoxy, tert-butoxy, pentoxy, hexyloxy, and the like.

"$(C_1-C_3)$alkoxy" refers to —O—$(C_1-C_3)$alkyl. Examples of $(C_1-C_6)$alkoxy groups include methoxy, ethoxy, propoxy, n-propoxy and iso-propoxy.

"Branched $(C_3-C_6)$alkoxy" refers to —O—$(C_3-C_6)$alkyl, wherein said $(C_3-C_6)$alkyl is branched. Examples of branched $(C_3-C_6)$alkoxy groups include iso-propoxy, sec-butoxy, tert-butoxy, 2-methyl-2-butoxy and the like.

"$(C_2-C_6)$alkenyloxy" refers to —O—$(C_2-C_6)$alkenyl. Examples of $(C_2-C_6)$alkenyloxy include ethenyloxy, propenyloxy, 1-propenyloxy, 2-propenyloxy, iso-propenyloxy, butenyloxy, 1-butenyloxy, 2-butenyloxy, 3-butenyloxy, iso-butenyloxy, sec-butenyloxy, tert-butenyloxy, pentenyloxy, 1-pentenyloxy, 2-pentenyloxy, 3-pentenyloxy, 4-pentenyloxy, iso-pentenyloxy, sec-pentenyloxy, tert-pentenyloxy, hexenyloxy, 1-hexenyloxy, 2-hexenyloxy, 3-hexenyloxy, 4-hexenyloxy, 5-hexenyloxy, iso-hexenyloxy, sec-hexenyloxy, tert-hexenyloxy and the like.

"$(C_2-C_6)$alkynyloxy" refers to —O—$(C_2-C_6)$alkynyl. Examples of $(C_2-C_6)$alkynyloxy include ethynyloxy, propynyloxy, 1-propynyloxy, 2-propynyloxy, butynyloxy, 1-butynyloxy, 2-butynyloxy, 3-butynyloxy, pentynyloxy, 1-pentynyloxy, 2-pentynyloxy, 3-pentynyloxy, 4-pentynyloxy, hexynyloxy, 1-hexynyloxy, 2-hexynyloxy, 3-hexynyloxy, 4-hexynyloxy, 5-hexynyloxy, and the like.

"$(C_5-C_7)$heterocycloalkyl" refers to a 5-, 6-, or 7-membered, saturated or partially unsaturated, mono- or bicyclic-heterocycle containing 1, 2, 3, or 4 ring heteroatoms each independently selected from nitrogen, oxygen, and sulfur, wherein said nitrogen and sulfur heteroatoms may optionally be oxidized and the nitrogen heteroatom may optionally be quaternized. A heterocycloalkyl group can be attached to the parent structure through a carbon or a heteroatom. Examples of $(C_5-C_7)$heterocycloalkyl groups include pyrrolidinyl, piperidinyl, piperazinyl, tetrahydro-oxazinyl, tetrahydrofuran, thiolane, dithiolane, pyrroline, pyrrolidine, pyrazoline, pyrazolidine, imidazoline, imidazolidine, tetrahydrofuranone, γ-butyrolactone, 2H-pyran, 4H-pyran, dioxolane, tetrahydropyran, dioxane, dihydrothiophene, piperazine, morpholine, thiomorpholine, oxazine, tetrahydro-oxazinyl, and the like.

$(C_6)$heterocycloalkyl" refers to a 6-membered, saturated or partially unsaturated, bridged, mono- or bicyclic-heterocycle containing 1, 2, 3, or 4 ring heteroatoms each independently selected from nitrogen, oxygen, and sulfur, wherein said nitrogen and sulfur heteroatoms may optionally be oxidized and the nitrogen heteroatom may optionally be quaternized. A heterocycloalkyl group can be attached to the parent structure through a carbon or heteroatom. Examples of $(C_6)$heterocycloalkyl groups include piperidinyl, piperazinyl, tetrahydro-oxazinyl, tetrahydropyran, dioxane, morpholine, thiomorpholine, and the like.

"$(C_6-C_{14})$aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of $(C_6-C_{14})$aryl groups include without limitation phenyl, naphthyl, indanyl, indenyl, tetralinyl, anthryl and phenanthryl. In some embodiments, the aryl is $C_6$ aryl. In some embodiments, the aryl is a bicyclic $C_9$-$C_{10}$ aryl. In some embodiments, the aryl is a tricyclic $C_{13}$-$C_{14}$ aryl. In some embodiments, the aryl is phenyl. In some embodiments, the aryl is naphthyl.

"($C_6$-$C_{10}$)aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of ($C_6$-$C_{10}$)aryl groups include without limitation phenyl, naphthyl, indanyl, indenyl and tetralinyl. In some embodiments, the aryl is $C_6$ aryl.

"($C_{10}$-$C_{14}$)aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of ($C_{10}$-$C_{14}$)aryl groups include without limitation naphthyl, tetralinyl, anthryl and phenanthryl.

"(9- or 10-membered)heteroaryl" refers to a bicyclic ring of 9 or 10 members in which at least one of rings in the bicyclic ring is aromatic and the bicyclic ring comprises at least one ring heteroatom, e.g., 1, 2, 3, or 4 ring heteroatoms, each independently selected from nitrogen, oxygen, and sulfur. A (9- or 10-membered)heteroaryl group can be attached to the parent structure through a carbon or heteroatom. Examples of (9- or 10-membered)heteroaryl include without limitation 1H-indazolyl, benzo[b]furyl, benzofuryl, benzo[1,3]dioxole, indolyl, isoindolyl, indolinyl, 1H-indolyl, 3H-indolyl, benzo[b]thiophenyl, benzthiazolyl, dihydroindole, indazolyl, benzimidazolyl, benzthiazolyl, quinolinyl, isoquinolinyl, cinnolyl, quinazolyl, quinoxalyl, 4H-quinolinyl, benzo-1,2,5-thiadiazolyl, purinyl, and pteridyl.

"(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. A (5- or 6-membered)heteroaryl group can be attached to the parent structure through a carbon or heteroatom. Examples of (5- or 6-membered)heteroaryls include pyridyl, pyrrolyl, pyrazolyl, furyl, imidazolyl, oxazolyl, thiazolyl, isoxazolyl, 1,2,3-oxadiazolyl, 1,3,4-oxadiazolyl, 1,2,5-oxadiazolyl, 1,2,3-triazolyl, tetrazolyl, pyrazolyl, isothiazolyl, pyridazinyl, pyrimidyl, pyrazyl, pyrazinyl, 1,2,3-thiadiazolyl, 1,3,4-thiadiazolyl, 1,2,5-thiadiazolyl, 1,3,5-triazinyl, and thiophenyl.

"(5-membered)heteroaryl" refers to a monocyclic aromatic heterocycle ring of 5 members, i.e., a monocyclic aromatic ring comprising at least one ring heteroatom, e.g., 1, 2, 3, or 4 ring heteroatoms, each independently selected from nitrogen, oxygen, and sulfur. A (5-membered)heteroaryl group can be attached to the parent structure through a carbon or heteroatom. Examples of (5-membered)heteroaryls include pyrrolyl, pyrazolyl, furyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, 1,2,3-thiadiazolyl, 1,3,4-thiadiazolyl and 1,2,5-thiadiazolyl.

"(6-membered)heteroaryl" refers to a monocyclic aromatic heterocycle ring of 6 members, i.e., a monocyclic aromatic ring comprising at least one ring heteroatom, e.g., 1, 2, 3, or 4 ring heteroatoms, each independently selected from nitrogen, oxygen, and sulfur. A (6-membered)heteroaryl group can be attached to the parent structure through a carbon or heteroatom. Examples of (6-membered)heteroaryls include pyridyl, pyridazinyl, pyrimidyl, pyrazinyl, 1,3,5-triazinyl, and thiophenyl.

"Halo" or "halogen" refers to fluoro (—F), chloro (—Cl), bromo (—Br) and iodo (—I).

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

4.2 N-Hydroxylamino-Barbituric Acid Type Nitroxyl Donors

It has been discovered the N-hydroxylamino-barbituric acid type compounds of the disclosure produce nitroxyl under physiologically relevant conditions and do not undergo intramolecular rearrangements. Without being bound by theory, the experiments reported herein suggest that, by tempering the electrophilicity of the $R^2$ group and/or the nucleophilicity of the hydroxylamine nitrogen, the non-HNO producing rearrangement becomes kinetically unfavorable, thereby allowing HNO production under physiologically relevant conditions.

In a particular embodiment, a nitroxyl donating compound of the disclosure is a compound of the formula (1):

(1)

[Structure: barbituric acid derivative with HO-HN and $R^2$ on one carbon, $R^1$ on nitrogens, and X substituent]

or a pharmaceutically acceptable salt thereof, wherein:

each $R^1$ is independently H or ($C_1$)alkyl;

$R^2$ is ($C_1$-$C_6$)alkyl substituted with a substituent selected from the group consisting of ($C_6$-$C_{14}$)aryl, ($C_3$-$C_6$) cycloalkyl, ($C_5$-$C_7$)heterocycloalkyl, (5- or 6-membered)heteroaryl and (9- or 10-membered)heteroaryl, wherein said aryl, cycloalkyl, heterocycloalkyl and heteroaryl are unsubstituted or substituted with 1, 2, 3, 4 or 5 substituents selected from $R^4$ and said alkyl is unsubstituted or substituted with 1, 2 or 3 substituents selected from $R^6$;

X is O, $NR^7$ or S;

each $R^4$ is independently selected from the group consisting of halo, —OH, —$NH_2$, —C≡N, —$NO_2$, —SH, =O, =S, =N—($C_1$-$C_4$)alkyl, ($C_1$-$C_6$)alkyl, ($C_2$-$C_6$) alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$) heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O) NR'R", —NHR', —NR'R", —SR', —S(O)R', —S(O)

OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl;

each $R^6$ is independently selected from the group consisting of halo and $(C_1-C_6)$alkyl; and $R^7$ is H or $(C_1-C_6)$alkyl.

In one embodiment, at least one of $R^1$ is H. In another, each $R^1$ is H.

In another embodiment, at least one of $R^1$ is $(C_1)$alkyl. In another embodiment, each $R^1$ is $(C_1)$alkyl.

In some aspects of this embodiment, X is S. In other aspects, X is O. In other aspects, X is NH. In other aspects, X is $N(C_1-C_6)$alkyl. In other aspects, X is $NCH_3$.

In one embodiment, at least one $R^1$ is H and X is S. In another embodiment, at least one $R^1$ is H and X is O. In another embodiment, at least one $R^1$ is H and X is NH. In another embodiment, at least one $R^1$ is H and X is $N(C_1-C_6)$alkyl. In another embodiment, at least one $R^1$ is H and X is $NCH_3$.

In another embodiment, each $R^1$ is H and X is S. In another embodiment, each $R^1$ is H and X is O. In another embodiment, each $R^1$ is H and X is NH. In another embodiment, each $R^1$ is H and X is $N(C_1-C_6)$alkyl. In another embodiment, each $R^1$ is H and X is $NCH_3$.

In one embodiment, at least one of $R^1$ is $(C_1)$alkyl and X is S. In another embodiment, at least one of $R^1$ is $(C_1)$alkyl and X is O. In another embodiment, at least one of $R^1$ is $(C_1)$alkyl and X is NH. In another embodiment, at least one $R^1$ is H and X is $N(C_1-C_6)$alkyl. In another embodiment, at least one $R^1$ is H and X is $NCH_3$.

In another embodiment, each $R^1$ is $(C_1)$alkyl and X is S. In another embodiment, each $R^1$ is $(C_1)$alkyl and X is O. In another embodiment, each $R^1$ is $(C_1)$alkyl and X is NH. In another embodiment, each $R^1$ is $(C_1)$alkyl and X is $N(C_1-C_6)$alkyl. In another embodiment, each $R^1$ is H and X is $NCH_3$.

In another embodiment, a nitroxyl donating compound of the disclosure is a compound of the formula (1a):

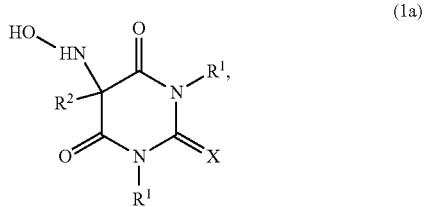

(1a)

or a pharmaceutically acceptable salt thereof, wherein:
each $R^1$ is independently H or $(C_1)$alkyl;
$R^2$ is $(C_1-C_6)$alkyl substituted with $(C_6-C_{14})$aryl, wherein said aryl is unsubstituted or substituted with 1, 2, 3, 4 or 5 substituents selected from $R^4$ and said alkyl is unsubstituted or substituted with 1, 2 or 3 substituents selected from $R^6$;
X is O, $NR^7$ or S;
each $R^4$ is independently selected from the group consisting of halo, —OH, —$NH_2$, —C≡N, —$NO_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl;

each $R^6$ is independently selected from the group consisting of halo and $(C_1-C_6)$alkyl; and $R^7$ is H or $(C_1-C_6)$alkyl.

In some aspects of this embodiment, at least one of $R^1$ is H. In some aspects, each $R^1$ is H.

In other aspects of this embodiment, at least one of $R^1$ is $(C_1)$alkyl. In some aspects, each $R^1$ is $(C_1)$alkyl.

In one embodiment, $R^2$ is $(C_1-C_4)$alkyl substituted with $(C_6-C_{14})$aryl. In another embodiment, $R^2$ is $(C_1-C_2)$alkyl substituted with $(C_6-C_{14})$aryl. In another embodiment, $R^2$ is $(C_1)$alkyl substituted with $(C_6-C_{14})$aryl. In each embodiment of this paragraph, the aryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the aryl is $C_6-C_{10}$ aryl. In various embodiments of each of the embodiments in this paragraph, the aryl is $C_{10}-C_{14}$ aryl. In various embodiments of each of the embodiments in this paragraph, the aryl is selected from the group consisting of phenyl, indanyl, indenyl, tetralinyl and naphthyl. In various embodiments of each of the embodiments in this paragraph, the aryl is phenyl.

In embodiments in which the aryl is substituted, each $R^4$ is independently selected from the group consisting of halo, —OH, —$NH_2$, —C≡N, —$NO_2$, —SH, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', —C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl.

In some embodiments, each $R^4$ is independently selected from the group consisting of —OH, —$NH_2$, —SH, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —NHR', —NR'R", —SR', —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl.

In another embodiment, each $R^4$ is independently selected from the group consisting of —OH, —$NH_2$, —SH, $(C_1-C_6)$alkyl, $(C_2-C_6)$alkenyl, $(C_2-C_6)$alkynyl, $(C_1-C_6)$alkoxy, $(C_2-C_6)$alkenyloxy and $(C_2-C_6)$alkynyloxy. In some embodiments, each $R^4$ is independently selected from the group consisting of —OH, —$NH_2$, —SH, $(C_1-C_6)$alkoxy, $(C_2-C_6)$alkenyloxy and $(C_2-C_6)$alkynyloxy. In other embodiments, each $R^4$ is independently selected from the group consisting of $(C_1-C_6)$alkoxy, $(C_2-C_6)$alkenyloxy and $(C_2-C_6)$alkynyloxy. In yet other embodiments, $R^4$ is $(C_1-C_6)$alkoxy. In some embodiments, $R^4$ is $(C_1-C_3)$alkoxy. In other embodiments, $R^4$ is methoxy. In some embodiments, $R^4$ is —OH.

In some embodiments, each $R^4$ is independently selected from the group consisting of halo, —C≡N, —$NO_2$, —C(O)

H, —C(O)NH$_2$, —C(O)OH, —NH—C(O)—NH$_2$, —NH—C(S)—NH$_2$, —SC≡N, —SO$_2$NH$_2$, —COR', —C(O)OR', —C(O)NHR', —C(O)NR'R", —S(O)R' and —S(O)OR', wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl, and (C$_5$-C$_7$)heterocycloalkyl.

In another embodiment, each R$^4$ is independently selected from the group consisting of halo, —C≡N, —NO$_2$, —C(O)NH$_2$, —C(O)OH, —COR', —C(O)OR', —C(O)NHR', —C(O)NR'R", —S(O)R' and —S(O)OR', wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_5$-C$_7$)heterocycloalkyl. In some embodiments, R$^4$ is halo. In some embodiments, R$^4$ is Cl. In some embodiments R$^4$ is S(O)O(C$_1$-C$_6$)alkyl. In some embodiments, R$^4$ is S(O)O(C$_1$)alkyl.

In embodiments in which said (C$_1$-C$_6$)alkyl is substituted with R$^6$, R$^6$ is halo or (C$_1$-C$_6$)alkyl. In some embodiments, R$^6$ is halo or (C$_1$-C$_4$)alkyl. In other embodiments, R$^6$ is halo or (C$_1$-C$_2$)alkyl. In other embodiments, R$^6$ is fluoro. In other embodiments, R$^6$ is methyl.

In some aspects of this embodiment, X is S. In other aspects, X is O. In other aspects, X is NH. In other aspects, X is N(C$_1$-C$_6$)alkyl. In other aspects, X is NCH$_3$.

In one embodiment, at least one R$^1$ is H and X is S. In another embodiment, at least one R$^1$ is H and X is O. In another embodiment, at least one R$^1$ is H and X is NH. In another embodiment, at least one R$^1$ is H and X is N(C$_1$-C$_6$)alkyl. In another embodiment, at least one R$^1$ is H and X is NCH$_3$.

In another embodiment, each R$^1$ is H and X is S. In another embodiment, each R$^1$ is H and X is O. In another embodiment, each R$^1$ is H and X is NH. In another embodiment, each R$^1$ is H and X is N(C$_1$-C$_6$)alkyl. In another embodiment, each R$^1$ is H and X is NCH$_3$.

In one embodiment, at least one of R$^1$ is (C$_1$)alkyl and X is S. In another embodiment, at least one of R$^1$ is (C$_1$)alkyl and X is O. In another embodiment, at least one of R$^1$ is (C$_1$)alkyl and X is NH. In another embodiment, at least one R$^1$ is H and X is N(C$_1$-C$_6$)alkyl. In another embodiment, at least one R$^1$ is H and X is NCH$_3$.

In another embodiment, each R$^1$ is (C$_1$)alkyl and X is S. In another embodiment, each R$^1$ is (C$_1$)alkyl and X is O. In another embodiment, each R$^1$ is (C$_1$)alkyl and X is NH. In another embodiment, each R$^1$ is H and X is N(C$_1$-C$_6$)alkyl. In another embodiment, each R$^1$ is H and X is NCH$_3$.

In one embodiment, at least one R$^1$ is H and R$^2$ is (C$_1$-C$_4$)alkyl substituted with (C$_6$-C$_{14}$)aryl. In another embodiment, at least one R$^1$ is H and R$^2$ is (C$_1$-C$_2$)alkyl substituted with (C$_6$-C$_{14}$)aryl. In another embodiment, at least one R$^1$ is H and R$^2$ is (C$_1$)alkyl substituted with (C$_6$-C$_{14}$)aryl. In each embodiment of this paragraph, the aryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the aryl is phenyl.

In one embodiment, each R$^1$ is H and R$^2$ is (C$_1$-C$_4$)alkyl substituted with (C$_6$-C$_{14}$)aryl. In another embodiment, each R$^1$ is H and R$^2$ is (C$_1$-C$_2$)alkyl substituted with (C$_6$-C$_{14}$)aryl. In another embodiment, each R$^1$ is H and R$^2$ is (C$_1$)alkyl substituted with (C$_6$-C$_{14}$)aryl. In each embodiment of this paragraph, the aryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the aryl is phenyl.

In one embodiment, at least one of R$^1$ is (C$_1$)alkyl and R$^2$ is (C$_1$-C$_4$)alkyl substituted with (C$_6$-C$_{14}$)aryl. In another embodiment, at least one of R$^1$ is (C$_1$)alkyl and R$^2$ is (C$_1$-C$_2$)alkyl substituted with (C$_6$-C$_{14}$)aryl. In another embodiment, at least one of R$^1$ is (C$_1$)alkyl and R$^2$ is (C$_1$)alkyl substituted with (C$_6$-C$_{14}$)aryl. In each embodiment of this paragraph, the aryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the aryl is phenyl.

In one embodiment, each R$^1$ is (C$_1$)alkyl and R$^2$ is (C$_1$-C$_4$)alkyl substituted with (C$_6$-C$_{14}$)aryl. In another embodiment, each R$^1$ is (C$_1$)alkyl and R$^2$ is (C$_1$-C$_2$)alkyl substituted with (C$_6$-C$_{14}$)aryl. In another embodiment, each R$^1$ is (C$_1$)alkyl and R$^2$ is (C$_1$)alkyl substituted with (C$_6$-C$_{14}$)aryl. In each embodiment of this paragraph, the aryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the aryl is phenyl.

In another embodiment, a nitroxyl donating compound of the disclosure is a compound of the formula (1a-1):

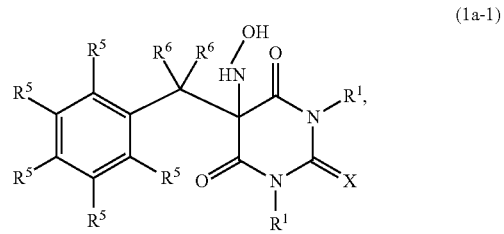

(1a-1)

or a pharmaceutically acceptable salt thereof, wherein:
each R$^1$ is (C$_1$)alkyl;
each R$^5$ is selected from the group consisting of H, halo, —OH, —NH$_2$, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_5$-C$_7$)heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_5$-C$_7$)heterocycloalkyl;
X is O, NR$^7$ or S;
each R$^6$ is independently selected from the group consisting of H, halo and (C$_1$-C$_6$)alkyl; and
R$^7$ is H or (C$_1$-C$_6$)alkyl.

In some embodiments, one or more of R$^5$ is selected from the group consisting of H, —OH, (C$_1$-C$_6$)alkoxy, —S(O)O(C$_1$-C$_6$)alkyl and halo. In some aspects, one or more of R$^5$ is selected from the group consisting of —OH, ($C_1$-$C_6$) alkoxy, $R^4$ is —S(O)O($C_1$-$C_6$)alkyl and halo. In some aspects, one or more of $R^5$ is methoxy. In other aspects, one or more of $R^5$ is Cl. In other aspects, one or more of $R^5$ is $R^4$ is —S(O)O($C_1$-$C_6$)alkyl. In other aspects, one or more of $R^5$ is —OH.

In one embodiment, one $R^5$ is methoxy and the other $R^5$ are H. In another embodiment, one $R^5$ is Cl and the other $R^5$ are H. In another embodiment, one $R^5$ is —S(O)O($C_1$-$C_6$)alkyl and the other $R^5$ are H. In another embodiment, one $R^5$ is —OH and the other $R^5$ are H.

In some embodiments, at least one of $R^6$ is H, halo or ($C_1$-$C_4$)alkyl. In some embodiments, at least one of $R^6$ is H, halo or ($C_1$-$C_2$)alkyl. In other embodiments, at least one of $R^6$ is fluoro. In other embodiments, at least one of $R^6$ is methyl. In other embodiments, at least one of $R^6$ is H.

In some aspects of this embodiment, X is S. In other aspects, X is O. In other aspects, X is NH. In other aspects, X is N($C_1$-$C_6$)alkyl. In other aspects, X is $NCH_3$.

In one embodiment, X is S and one $R^5$ is methoxy and the other $R^5$ are H. In another embodiment, X is O and one $R^5$ is methoxy and the other $R^5$ are H. In another embodiment, X is NH and one $R^5$ is methoxy and the other $R^5$ are H. In another embodiment, X is $NCH_3$ and one $R^5$ is methoxy and the other $R^5$ are H.

In one embodiment, X is S and one $R^5$ is Cl and the other $R^5$ are H. In another embodiment, X is O and one $R^5$ is Cl and the other $R^5$ are H. In another embodiment, X is NH and one $R^5$ is Cl and the other $R^5$ are H. In another embodiment, X is $NCH_3$ and one $R^5$ is Cl and the other $R^5$ are H.

In one embodiment, X is S and one $R^5$ is —S(O)O($C_1$-$C_6$)alkyl and the other $R^5$ are H. In another embodiment, X is O and one $R^5$ is —S(O)O($C_1$-$C_6$)alkyl and the other $R^5$ are H. In another embodiment, X is NH and one $R^5$ is —S(O)O($C_1$-$C_6$)alkyl and the other $R^5$ are H. In another embodiment, X is $NCH_3$ and one $R^5$ is —S(O)O($C_1$-$C_6$)alkyl and the other $R^5$ are H.

In another embodiment, a nitroxyl donating compound of the disclosure is a compound of the formula (1a-2):

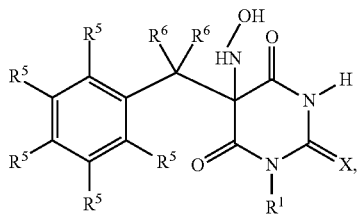

(1a-2)

or a pharmaceutically acceptable salt thereof, wherein:
$R^1$ is ($C_1$)alkyl;
each $R^5$ is selected from the group consisting of H, halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl;

X is O, $NR^7$ or S;
each $R^6$ is independently selected from the group consisting of H, halo and ($C_1$-$C_6$)alkyl; and
$R^7$ is H or ($C_1$-$C_6$)alkyl.

In some embodiments, one or more of $R^5$ is selected from the group consisting of H, —OH, ($C_1$-$C_6$)alkoxy, —S(O)O ($C_1$-$C_6$)alkyl and halo. In some aspects, one or more of $R^5$ is selected from the group consisting of —OH, ($C_1$-$C_6$) alkoxy, —S(O)O($C_1$-$C_6$)alkyl and halo. In some aspects, one or more of $R^5$ is methoxy. In other aspects, one or more of $R^5$ is Cl. In other aspects, one or more of $R^5$ is —S(O) O($C_1$-$C_6$)alkyl. In other aspects, one or more of $R^5$ is —OH.

In one embodiment, one $R^5$ is methoxy and the other $R^5$ are H. In another embodiment, one $R^5$ is Cl and the other $R^5$ are H. In another embodiment, one $R^5$ is —S(O)O($C_1$-$C_6$)alkyl and the other $R^5$ are H. In another embodiment, one $R^5$ is —OH and the other $R^5$ are H.

In some embodiments, at least one of $R^6$ is H, halo or ($C_1$-$C_4$)alkyl. In some embodiments, at least one of $R^6$ is H, halo or ($C_1$-$C_2$)alkyl. In other embodiments, at least one of $R^6$ is fluoro. In other embodiments, at least one of $R^6$ is methyl. In other embodiments, at least one of $R^6$ is H.

In some aspects of this embodiment, X is S. In other aspects, X is O. In other aspects, X is NH. In other aspects, X is N($C_1$-$C_6$)alkyl. In other aspects, X is $NCH_3$.

In one embodiment, X is S and one $R^5$ is methoxy and the other $R^5$ are H. In another embodiment, X is O and one $R^5$ is methoxy and the other $R^5$ are H. In another embodiment, X is NH and one $R^5$ is methoxy and the other $R^5$ are H. In another embodiment, X is $NCH_3$ and one $R^5$ is methoxy and the other $R^5$ are H.

In one embodiment, X is S and one $R^5$ is Cl and the other $R^5$ are H. In another embodiment, X is O and one $R^5$ is Cl and the other $R^5$ are H. In another embodiment, X is NH and one $R^5$ is Cl and the other $R^5$ are H. In another embodiment, X is $NCH_3$ and one $R^5$ is Cl and the other $R^5$ are H.

In one embodiment, X is S and one $R^5$ is —S(O)O($C_1$-$C_6$)alkyl and the other $R^5$ are H. In another embodiment, X is O and one $R^5$ is —S(O)O($C_1$-$C_6$)alkyl and the other $R^5$ are H. In another embodiment, X is NH and one $R^5$ is —S(O) O($C_1$-$C_6$)alkyl and the other $R^5$ are H. In another embodiment, X is $NCH_3$ and one $R^5$ is —S(O)O($C_1$-$C_6$)alkyl and the other $R^5$ are H.

In one embodiment, X is S and one $R^5$ is —OH and the other $R^5$ are H. In another embodiment, X is O and one $R^5$ is —OH and the other $R^5$ are H. In another embodiment, X is NH and one $R^5$ is —OH and the other $R^5$ are H. In another embodiment, X is $NCH_3$ and one $R^5$ is —OH and the other $R^5$ are H.

In another embodiment, a nitroxyl donating compound of the disclosure is a compound of the formula (1b):

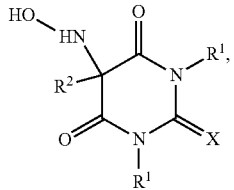

(1b)

or a pharmaceutically acceptable salt thereof, wherein:
each $R^1$ is independently H or ($C_1$)alkyl;
$R^2$ is ($C_1$-$C_6$)alkyl substituted with ($C_3$-$C_6$)cycloalkyl, wherein said cycloalkyl is unsubstituted or substituted with 1, 2 or 3 substituents selected from $R^4$ and said alkyl is unsubstituted or substituted with 1, 2 or 3 substituents selected from $R^6$;

X is O, $NR^7$ or S;

each $R^4$ is independently selected from the group consisting of halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl;

each $R^6$ is independently selected from halo the group consisting of and ($C_1$-$C_6$)alkyl; and $R^7$ is H or ($C_1$-$C_6$)alkyl.

In some aspects of this embodiment, at least one of $R^1$ is H. In some aspects, each $R^1$ is H.

In other aspects of this embodiment, at least one of $R^1$ is ($C_1$)alkyl. In some aspects, each $R^1$ is ($C_1$)alkyl.

In one embodiment, $R^2$ is ($C_1$-$C_4$)alkyl substituted with ($C_3$-$C_6$)cycloalkyl. In another embodiment, $R^2$ is ($C_1$-$C_2$)alkyl substituted with ($C_3$-$C_6$)cycloalkyl. In another embodiment, $R^2$ is ($C_1$)alkyl substituted with ($C_3$-$C_6$)cycloalkyl. In each embodiment of this paragraph, the cycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the ($C_3$-$C_6$)cycloalkyl is selected from the group consisting of cyclopropyl, cyclobutyl, cyclopentyl and cyclohexyl. In various embodiments of each of the embodiments in this paragraph, the ($C_3$-$C_6$)cycloalkyl is cyclohexyl.

In embodiments in which said ($C_1$-$C_6$)alkyl is substituted with $R^6$, $R^6$ is halo or ($C_1$-$C_6$)alkyl. In some embodiments, $R^6$ is halo or ($C_1$-$C_4$)alkyl. In other embodiments, $R^6$ is halo or ($C_1$-$C_2$)alkyl. In other embodiments, $R^6$ is fluoro. In other embodiments, $R^6$ is methyl.

In some aspects of this embodiment, X is S. In other aspects, X is O. In other aspects, X is NH. In other aspects, X is N($C_1$-$C_6$)alkyl. In other aspects, X is $NCH_3$.

In one embodiment, at least one $R^1$ is H and X is S. In another embodiment, at least one $R^1$ is H and X is O. In another embodiment, at least one $R^1$ is H and X is NH. In another embodiment, at least one $R^1$ is H and X is N($C_1$-$C_6$)alkyl. In another embodiment, at least one $R^1$ is H and X is $NCH_3$.

In another embodiment, each $R^1$ is H and X is S. In another embodiment, each $R^1$ is H and X is O. In another embodiment, each $R^1$ is H and X is NH. In another embodiment, each $R^1$ is H and X is N($C_1$-$C_6$)alkyl. In another embodiment, each $R^1$ is H and X is $NCH_3$.

In one embodiment, at least one of $R^1$ is ($C_1$)alkyl and X is S. In another embodiment, at least one of $R^1$ is ($C_1$)alkyl and X is O. In another embodiment, at least one of $R^1$ is ($C_1$)alkyl and X is NH. In another embodiment, at least one $R^1$ is H and X is N($C_1$-$C_6$)alkyl. In another embodiment, at least one $R^1$ is H and X is $NCH_3$.

In another embodiment, each $R^1$ is ($C_1$)alkyl and X is S. In another embodiment, each $R^1$ is ($C_1$)alkyl and X is O. In another embodiment, each $R^1$ is ($C_1$)alkyl and X is NH. In another embodiment, each $R^1$ is H and X is N($C_1$-$C_6$)alkyl. In another embodiment, each $R^1$ is H and X is $NCH_3$.

In one embodiment, at least one $R^1$ is H and $R^2$ is ($C_1$-$C_4$)alkyl substituted with ($C_3$-$C_6$)cycloalkyl. In another embodiment, at least one $R^1$ is H and $R^2$ is ($C_1$-$C_2$)alkyl substituted with ($C_3$-$C_6$)cycloalkyl. In another embodiment, at least one $R^1$ is H and $R^2$ is ($C_1$)alkyl substituted with ($C_3$-$C_6$)cycloalkyl. In each embodiment of this paragraph, the cycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the cycloalkyl is cyclohexyl.

In one embodiment, each $R^1$ is H and $R^2$ is ($C_1$-$C_4$)alkyl substituted with ($C_3$-$C_6$)cycloalkyl. In another embodiment, each $R^1$ is H and $R^2$ is ($C_1$-$C_2$)alkyl substituted with ($C_3$-$C_6$)cycloalkyl. In another embodiment, each $R^1$ is H and $R^2$ is ($C_1$)alkyl substituted with ($C_3$-$C_6$)cycloalkyl. In each embodiment of this paragraph, the cycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the cycloalkyl is cyclohexyl.

In one embodiment, at least one of $R^1$ is ($C_1$)alkyl and $R^2$ is ($C_1$-$C_4$)alkyl substituted with ($C_3$-$C_6$)cycloalkyl. In another embodiment, at least one of $R^1$ is ($C_1$)alkyl and $R^2$ is ($C_1$-$C_2$)alkyl substituted with ($C_3$-$C_6$)cycloalkyl. In another embodiment, at least one of $R^1$ is ($C_1$)alkyl and $R^2$ is ($C_1$)alkyl substituted with ($C_3$-$C_6$)cycloalkyl. In each embodiment of this paragraph, the cycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the cycloalkyl is cyclohexyl.

In one embodiment, each $R^1$ is ($C_1$)alkyl and $R^2$ is ($C_1$-$C_4$)alkyl substituted with ($C_3$-$C_6$)cycloalkyl. In another embodiment, each $R^1$ is ($C_1$)alkyl and $R^2$ is ($C_1$-$C_2$)alkyl substituted with ($C_3$-$C_6$)cycloalkyl. In another embodiment, each $R^1$ is ($C_1$)alkyl and $R^2$ is ($C_1$)alkyl substituted with ($C_3$-$C_6$)cycloalkyl. In each embodiment of this paragraph, the cycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the cycloalkyl is cyclohexyl.

In another embodiment, a nitroxyl donating compound of the disclosure is a compound of the formula (1c):

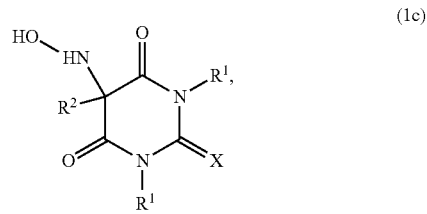

(1c)

or a pharmaceutically acceptable salt thereof, wherein:
each $R^1$ is independently H or ($C_1$)alkyl;
$R^2$ is ($C_1$-$C_6$)alkyl substituted with ($C_5$-$C_7$)heterocycloalkyl, wherein said heterocycloalkyl is unsubstituted or substituted with 1, 2, 3, 4 or 5 substituents selected from $R^4$ and said alkyl is unsubstituted or substituted with 1, 2 or 3 substituents selected from $R^6$;

X is O, $NR^7$ or S;

each $R^4$ is independently selected from the group consisting of halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl;

each $R^6$ is independently selected from the group consisting of halo and ($C_1$-$C_6$)alkyl; and $R^7$ is H or ($C_1$-$C_6$)alkyl.

In some aspects of this embodiment, at least one of $R^1$ is H. In some aspects, each $R^1$ is H.

In other aspects of this embodiment, at least one of $R^1$ is ($C_1$)alkyl. In some aspects, each $R^1$ is ($C_1$)alkyl.

In one embodiment, $R^2$ is ($C_1$-$C_4$)alkyl substituted with ($C_5$-$C_7$)heterocycloalkyl. In another embodiment, $R^2$ is ($C_1$-$C_2$)alkyl substituted with ($C_5$-$C_7$)heterocycloalkyl. In another embodiment, $R^2$ is ($C_1$)alkyl substituted with ($C_5$-$C_7$)heterocycloalkyl. In each embodiment of this paragraph, the heterocycloalkyl is unsubstituted in one embodiment, mono-substituted in another embodiment, di-substituted with two independently selected substituents in an additional embodiment, or tri-substituted with three independently selected substituents in a further embodiment.

In some aspects of this embodiment, the heterocycloalkyl is selected from the group consisting of pyrrolidinyl, piperidinyl, piperazinyl, tetrahydro-oxazinyl, tetrahydrofuran, thiolane, dithiolane, pyrroline, pyrrolidine, pyrazoline, pyrazolidine, imidazoline, imidazolidine, tetrahydrofuranone, γ-butyrolactone, 2H-pyran, 4H-pyran, dioxolane, tetrahydropyran, dioxane, dihydrothiophene, piperazine, morpholine, thiomorpholine, oxazine and tetrahydro-oxazinyl.

In some aspects of this embodiment, the heterocycloalkyl is a ($C_6$)heterocycloalkyl selected from the group consisting of piperidinyl, piperazinyl, tetrahydro-oxazinyl, tetrahydropyran, dioxane, morpholine and thiomorpholine.

In embodiments in which said ($C_1$-$C_6$)alkyl is substituted with $R^6$, $R^6$ is halo or ($C_1$-$C_6$)alkyl. In some embodiments, $R^6$ is halo or ($C_1$-$C_4$)alkyl. In other embodiments, $R^6$ is halo or ($C_1$-$C_2$)alkyl. In other embodiments, $R^6$ is fluoro. In other embodiments, $R^6$ is methyl.

In some aspects of this embodiment, X is S. In other aspects, X is O. In other aspects, X is NH. In other aspects, X is N($C_1$-$C_6$)alkyl. In other aspects, X is $NCH_3$.

In one embodiment, at least one $R^1$ is H and X is S. In another embodiment, at least one $R^1$ is H and X is O. In another embodiment, at least one $R^1$ is H and X is NH. In another embodiment, at least one $R^1$ is H and X is N($C_1$-$C_6$)alkyl. In another embodiment, at least one $R^1$ is H and X is $NCH_3$.

In another embodiment, each $R^1$ is H and X is S. In another embodiment, each $R^1$ is H and X is O. In another embodiment, each $R^1$ is H and X is NH. In another embodiment, each $R^1$ is H and X is N($C_1$-$C_6$)alkyl. In another embodiment, each $R^1$ is H and X is $NCH_3$.

In one embodiment, at least one of $R^1$ is ($C_1$)alkyl and X is S. In another embodiment, at least one of $R^1$ is ($C_1$)alkyl and X is O. In another embodiment, at least one of $R^1$ is ($C_1$)alkyl and X is NH. In another embodiment, at least one $R^1$ is H and X is N($C_1$-$C_6$)alkyl. In another embodiment, at least one $R^1$ is H and X is $NCH_3$.

In another embodiment, each $R^1$ is ($C_1$)alkyl and X is S. In another embodiment, each $R^1$ is ($C_1$)alkyl and X is O. In another embodiment, each $R^1$ is ($C_1$)alkyl and X is NH. In another embodiment, each $R^1$ is H and X is N($C_1$-$C_6$)alkyl. In another embodiment, each $R^1$ is H and X is $NCH_3$.

In one embodiment, at least one $R^1$ is H and $R^2$ is ($C_1$-$C_4$)alkyl substituted with ($C_5$-$C_7$)heterocycloalkyl. In another embodiment, at least one $R^1$ is H and $R^2$ is ($C_1$-$C_2$) alkyl substituted with ($C_5$-$C_7$)heterocycloalkyl. In another embodiment, at least one $R^1$ is H and $R^2$ is ($C_1$)alkyl substituted with ($C_5$-$C_7$)heterocycloalkyl. In each embodiment of this paragraph, the heterocycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heterocycloalkyl is ($C_5$)heterocycloalkyl. In various embodiments of each of the embodiments in this paragraph, the heterocycloalkyl is ($C_6$)heterocycloalkyl.

In one embodiment, each $R^1$ is H and $R^2$ is ($C_1$-$C_4$)alkyl substituted with ($C_5$-$C_7$)heterocycloalkyl. In another embodiment, each $R^1$ is H and $R^2$ is ($C_1$-$C_2$) alkyl substituted with ($C_5$-$C_7$)heterocycloalkyl. In another embodiment, each $R^1$ is H and $R^2$ is ($C_1$)alkyl substituted with ($C_5$-$C_7$)heterocycloalkyl. In each embodiment of this paragraph, the heterocycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heterocycloalkyl is ($C_5$)heterocycloalkyl. In various embodiments of each of the embodiments in this paragraph, the heterocycloalkyl is ($C_6$)heterocycloalkyl.

In one embodiment, at least one of $R^1$ is ($C_1$)alkyl and $R^2$ is ($C_1$-$C_4$)alkyl substituted with ($C_5$-$C_7$)heterocycloalkyl. In another embodiment, at least one of $R^1$ is ($C_1$)alkyl and $R^2$ is ($C_1$-$C_2$)alkyl substituted with ($C_5$-$C_7$)heterocycloalkyl. In another embodiment, at least one of $R^1$ is ($C_1$)alkyl and $R^2$ is ($C_1$)alkyl substituted with ($C_5$-$C_7$)heterocycloalkyl. In each embodiment of this paragraph, the heterocycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heterocycloalkyl is ($C_5$)heterocycloalkyl. In various embodiments of each of the embodiments in this paragraph, the heterocycloalkyl is ($C_6$)heterocycloalkyl.

In one embodiment, each $R^1$ is ($C_1$)alkyl and $R^2$ is ($C_1$-$C_4$)alkyl substituted with ($C_5$-$C_7$)heterocycloalkyl. In another embodiment, each $R^1$ is ($C_1$)alkyl and $R^2$ is ($C_1$-$C_2$) alkyl substituted with ($C_5$-$C_7$)heterocycloalkyl. In another embodiment, each $R^1$ is ($C_1$)alkyl and $R^2$ is ($C_1$)alkyl substituted with ($C_5$-$C_7$)heterocycloalkyl. In each embodiment of this paragraph, the heterocycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heterocycloalkyl is ($C_5$)heterocycloalkyl. In various embodiments of each of the embodiments in this paragraph, the heterocycloalkyl is (C_6)heterocycloalkyl.

In another embodiment, a nitroxyl donating compound of the disclosure is a compound of the formula (1d):

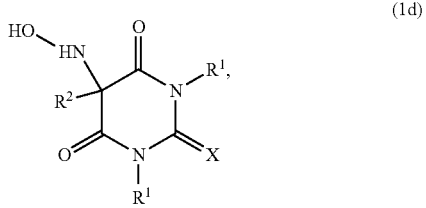

(1d)

or a pharmaceutically acceptable salt thereof, wherein:
each $R^1$ is independently H or $(C_1)$alkyl;
$R^2$ is $(C_1-C_6)$alkyl substituted with (5- or 6-membered) heteroaryl or (9- or 10-membered)heteroaryl, wherein said heteroaryl is unsubstituted or substituted with 1, 2, 3, 4 or 5 substituents selected from $R^4$ and said alkyl is unsubstituted or substituted with 1, 2 or 3 substituents selected from $R^6$;
X is O, $NR^7$ or S;
each $R^4$ is independently selected from the group consisting of halo, —OH, —NH_2, —C≡N, —NO_2, —SH, =O, =S, =N—(C_1-C_4)alkyl, (C_1-C_6)alkyl, (C_2-C_6) alkenyl, (C_2-C_6)alkynyl, (C_1-C_6)alkoxy, (C_2-C_6)alkenyloxy, (C_2-C_6)alkynyloxy, (C_6-C_14)aryl, (C_3-C_6)cycloalkyl, (5- or 6-membered)heteroaryl, (C_5-C_7) heterocycloalkyl, —C(O)H, —C(O)NH_2, —C(O)OH, —NH—C(O)—NH_2, —NH—C(S)—NH_2, —SC≡N, —SO_2NH_2, —COR', —C(O)OR', C(O)NHR', —C(O)NR'R", —NHR', —NR'R", —SR', —S(O)R', —S(O)OR', and —OR', wherein R' and R" are independently selected from (C_1-C_6)alkyl, (C_2-C_6)alkenyl, (C_2-C_6) alkynyl, (C_6-C_14)aryl, (C_3-C_6)cycloalkyl, (5- or 6-membered)heteroaryl and (C_5-C_7)heterocycloalkyl;
each $R^6$ is independently selected from the group consisting of halo and $(C_1-C_6)$alkyl; and
$R^7$ is H or $(C_1-C_6)$alkyl.

In some aspects of this embodiment, at least one of $R^1$ is H. In other aspects, each $R^1$ is H.

In other aspects of this embodiment, at least one of $R^1$ is $(C_1)$alkyl. In some aspects, each $R^1$ is $(C_1)$alkyl.

In one embodiment, $R^2$ is $(C_1-C_4)$alkyl substituted with (5- or 6-membered)heteroaryl or (9- or 10-membered)heteroaryl. In another embodiment, $R^2$ is $(C_1-C_2)$alkyl substituted with (5- or 6-membered)heteroaryl or (9- or 10-membered)heteroaryl. In another embodiment, $R^2$ is $(C_1)$alkyl substituted with (5- or 6-membered)heteroaryl or (9- or 10-membered)heteroaryl. In each embodiment of this paragraph, the heteroaryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heteroaryl is a (5-membered)heteroaryl in one embodiment, a (6-membered)heteroaryl in another embodiment, a (9-membered)heteroaryl in an additional embodiment, and a (10-membered)heteroaryl in a further embodiment.

In some aspects of this embodiment, the heteroaryl is selected from the group consisting of pyridyl, pyrrolyl, pyrazolyl, furyl, thienyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, thiophenyl, 1H-indolyl, 3H-indolyl and benzo[d][1,3]dioxol.

In some embodiments, the heteroaryl is selected from the group consisting of furyl, thienyl, imidazolyl, pyridyl, pyridazinyl, pyrimidyl, pyrazinyl, 1,3,5-triazinyl, thiophenyl, 1H-indolyl, 3H-indolyl and benzo[d][1,3]dioxol.

In embodiments in which said $(C_1-C_6)$alkyl is substituted with $R^6$, $R^6$ is halo or $(C_1-C_6)$alkyl. In some embodiments, $R^6$ is halo or $(C_1-C_4)$alkyl. In other embodiments, $R^6$ is halo or $(C_1-C_2)$alkyl. In other embodiments, $R^6$ is fluoro. In other embodiments, $R^6$ is methyl.

In some aspects of this embodiment, X is S. In other aspects, X is O. In other aspects, X is NH. In other aspects, X is $N(C_1-C_6)$alkyl. In other aspects, X is $NCH_3$.

In one embodiment, at least one $R^1$ is H and X is S. In another embodiment, at least one $R^1$ is H and X is O. In another embodiment, at least one $R^1$ is H and X is NH. In another embodiment, at least one $R^1$ is H and X is $N(C_1-C_6)$alkyl. In another embodiment, at least one $R^1$ is H and X is $NCH_3$.

In another embodiment, each $R^1$ is H and X is S. In another embodiment, each $R^1$ is H and X is O. In another embodiment, each $R^1$ is H and X is NH. In another embodiment, each $R^1$ is H and X is $N(C_1-C_6)$alkyl. In another embodiment, each $R^1$ is H and X is $NCH_3$.

In one embodiment, at least one of $R^1$ is $(C_1)$alkyl and X is S. In another embodiment, at least one of $R^1$ is $(C_1)$alkyl and X is O. In another embodiment, at least one of $R^1$ is $(C_1)$alkyl and X is NH. In another embodiment, at least one $R^1$ is H and X is $N(C_1-C_6)$alkyl. In another embodiment, at least one $R^1$ is H and X is $NCH_3$.

In another embodiment, each $R^1$ is $(C_1)$alkyl and X is S. In another embodiment, each $R^1$ is $(C_1)$alkyl and X is O. In another embodiment, each $R^1$ is $(C_1)$alkyl and X is NH. In another embodiment, each $R^1$ is H and X is $N(C_1-C_6)$alkyl. In another embodiment, each $R^1$ is H and X is $NCH_3$.

In one embodiment, at least one $R^1$ is H and $R^2$ is $(C_1-C_4)$alkyl substituted with (5- or 6-membered)heteroaryl or (9- or 10-membered)heteroaryl. In another embodiment, at least one $R^1$ is H and $R^2$ is $(C_1-C_2)$alkyl substituted with (5- or 6-membered)heteroaryl or (9- or 10-membered)heteroaryl. In another embodiment, at least one $R^1$ is H and $R^2$ is $(C_1)$alkyl substituted with (5- or 6-membered)heteroaryl or (9- or 10-membered)heteroaryl. In each embodiment of this paragraph, the heteroaryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heteroaryl is furyl. In various embodiments of each of the embodiments in this paragraph, the heteroaryl is thienyl. In various embodiments of each of the embodiments in this paragraph, the heteroaryl is imidazolyl. In various embodiments of each of the embodiments in this paragraph, the heteroaryl is pyridyl. In various embodiments of each of the embodiments in this paragraph, the heteroaryl is 1H-indolyl. In various embodiments of each of the embodiments in this paragraph, the heteroaryl is 3H-indolyl. In various embodiments of each of the embodiments in this paragraph, the heteroaryl is benzo[d][1,3]dioxolyl.

In one embodiment, each $R^1$ is H and $R^2$ is $(C_1-C_4)$alkyl substituted with (5- or 6-membered)heteroaryl or (9- or 10-membered)heteroaryl. In another embodiment, each $R^1$ is H and $R^2$ is $(C_1-C_2)$alkyl substituted with (5- or 6-membered)heteroaryl or (9- or 10-membered)heteroaryl. In another embodiment, each R¹ is H and R² is (C₁)alkyl substituted with (5- or 6-membered)heteroaryl or (9- or 10-membered)heteroaryl. In each embodiment of this paragraph, the heteroaryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heteroaryl is furyl. In various embodiments of each of the embodiments in this paragraph, the heteroaryl is thienyl. In various embodiments of each of the embodiments in this paragraph, the heteroaryl is imidazolyl. In various embodiments of each of the embodiments in this paragraph, the heteroaryl is pyridyl. In various embodiments of each of the embodiments in this paragraph, the heteroaryl is 1H-indolyl. In various embodiments of each of the embodiments in this paragraph, the heteroaryl is 3H-indolyl. In various embodiments of each of the embodiments in this paragraph, the heteroaryl is benzo[d][1,3]dioxolyl.

In one embodiment, at least one of R¹ is (C₁)alkyl and R² is (C₁-C₄)alkyl substituted with (5- or 6-membered)heteroaryl or (9- or 10-membered)heteroaryl. In another embodiment, at least one of R¹ is (C₁)alkyl and R² is (C₁-C₂)alkyl substituted with (5- or 6-membered)heteroaryl or (9- or 10-membered)heteroaryl. In another embodiment, at least one of R¹ is (C₁)alkyl and R² is (C₁)alkyl substituted with (5- or 6-membered)heteroaryl or (9- or 10-membered) heteroaryl. In each embodiment of this paragraph, the heteroaryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heteroaryl is furyl. In various embodiments of each of the embodiments in this paragraph, the heteroaryl is thienyl. In various embodiments of each of the embodiments in this paragraph, the heteroaryl is imidazolyl. In various embodiments of each of the embodiments in this paragraph, the heteroaryl is pyridyl. In various embodiments of each of the embodiments in this paragraph, the heteroaryl is 1H-indolyl. In various embodiments of each of the embodiments in this paragraph, the heteroaryl is 3H-indolyl. In various embodiments of each of the embodiments in this paragraph, the heteroaryl is benzo[d][1,3]dioxolyl.

In one embodiment, each R¹ is (C₁)alkyl and R² is (C₁-C₄)alkyl substituted with (5- or 6-membered)heteroaryl or (9- or 10-membered)heteroaryl. In another embodiment, each R¹ is (C₁)alkyl and R² is (C₁-C₂)alkyl substituted with (5- or 6-membered)heteroaryl or (9- or 10-membered)heteroaryl. In another embodiment, each R¹ is (C₁)alkyl and R² is (C₁)alkyl substituted with (5- or 6-membered)heteroaryl or (9- or 10-membered)heteroaryl. In each embodiment of this paragraph, the heteroaryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heteroaryl is furyl. In various embodiments of each of the embodiments in this paragraph, the heteroaryl is thienyl. In various embodiments of each of the embodiments in this paragraph, the heteroaryl is imidazolyl. In various embodiments of each of the embodiments in this paragraph, the heteroaryl is pyridyl. In various embodiments of each of the embodiments in this paragraph, the heteroaryl is 1H-indolyl. In various embodiments of each of the embodiments in this paragraph, the heteroaryl is 3H-indolyl. In various embodiments of each of the embodiments in this paragraph, the heteroaryl is benzo[d][1,3]dioxolyl.

According to one embodiment, the compound of formula (1) is:

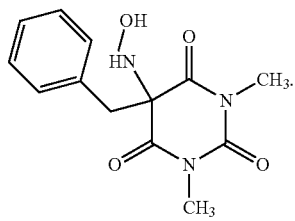

1

According to one embodiment, the compound of formula (1) is:

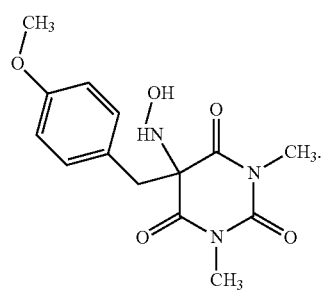

2

According to one embodiment, the compound of formula (1) is:

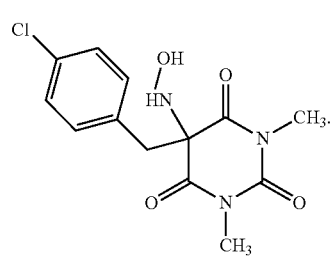

3

In particular embodiments, compounds 1, 2 or 3 are utilized as a pharmaceutically acceptable salt thereof.

In another embodiment, a nitroxyl donating compound of the disclosure is a compound of the formula (2):

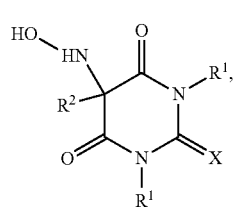

(2)

or a pharmaceutically acceptable salt thereof, wherein:
each R¹ is independently H or (C₁)alkyl;
R² is selected from the group consisting of a branched C₃-C₆ alkyl, a branched C₃-C₆ alkenyl, and a branched $C_3$-$C_6$ alkoxy, wherein said alkyl, alkenyl, and alkoxy are unsubstituted or substituted with 1, 2 or 3 substituents selected from $R^4$;

X is O, $NR^7$ or S;

each $R^4$ is independently selected from the group consisting of halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl; and $R^7$ is H or ($C_1$-$C_6$)alkyl.

In some aspects of this embodiment, at least one of $R^1$ is H. In some aspects, each $R^1$ is H.

In other aspects of this embodiment, at least one of $R^1$ is ($C_1$)alkyl. In some aspects, each $R^1$ is ($C_1$)alkyl.

According to a first embodiment, $R^2$ is a branched $C_3$-$C_6$ alkyl, wherein said alkyl is unsubstituted or substituted with 1, 2 or 3 substituents selected from $R^4$. In one embodiment, $R^2$ is a substituted, branched $C_3$-$C_6$ alkyl. In another embodiment, $R^2$ is an unsubstituted, branched $C_3$-$C_6$ alkyl. In one embodiment, $R^2$ is selected from the group consisting of iso-propyl, sec-butyl, iso-butyl, tert-butyl, methylbutyl, iso-pentyl, methylpentyl, ethylbutyl, dimethylbutyl, and iso-propylpropyl. In other embodiments, $R^2$ is selected from the group consisting of sec-butyl, iso-butyl, tert-butyl, methylbutyl, iso-pentyl, methylpentyl, ethylbutyl, dimethylbutyl, and iso-propylpropyl.

According to a second embodiment, $R^2$ is a branched $C_3$-$C_6$ alkenyl, wherein said alkenyl is unsubstituted or substituted with 1, 2 or 3 substituents selected from $R^4$. In one embodiment, $R^2$ is a substituted, branched $C_3$-$C_6$ alkenyl. In another embodiment, $R^2$ is an unsubstituted, branched $C_3$-$C_6$ alkenyl.

According to a third embodiment, $R^2$ is a branched $C_3$-$C_6$ alkoxy, wherein said alkoxy is unsubstituted or substituted with 1, 2 or 3 substituents selected from $R^4$. In one embodiment, $R^2$ is a substituted, branched $C_3$-$C_6$ alkoxy. In another embodiment, $R^2$ is an unsubstituted, branched $C_3$-$C_6$ alkoxy.

In some aspects of this embodiment, X is S. In other aspects, X is O. In other aspects, X is NH. In other aspects, X is N($C_1$-$C_6$)alkyl. In other aspects, X is $NCH_3$.

In one embodiment, at least one $R^1$ is H and X is S. In another embodiment, at least one $R^1$ is H and X is O. In another embodiment, at least one $R^1$ is H and X is NH. In another embodiment, at least one $R^1$ is H and X is N($C_1$-$C_6$)alkyl. In another embodiment, at least one $R^1$ is H and X is $NCH_3$.

In another embodiment, each $R^1$ is H and X is S. In another embodiment, each $R^1$ is H and X is O. In another embodiment, each $R^1$ is H and X is NH. In another embodiment, each $R^1$ is H and X is N($C_1$-$C_6$)alkyl. In another embodiment, each $R^1$ is H and X is $NCH_3$.

In one embodiment, at least one of $R^1$ is ($C_1$)alkyl and X is S. In another embodiment, at least one of $R^1$ is ($C_1$)alkyl and X is NH. In another embodiment, at least one $R^1$ is ($C_1$)alkyl and X is N($C_1$-$C_6$)alkyl. In another embodiment, at least one $R^1$ is H and X is $NCH_3$.

In another embodiment, each $R^1$ is ($C_1$)alkyl and X is S. In another embodiment, each $R^1$ is ($C_1$)alkyl and X is O. In another embodiment, each $R^1$ is ($C_1$)alkyl and X is NH. In another embodiment, each $R^1$ is H and X is N($C_1$-$C_6$)alkyl. In another embodiment, each $R^1$ is H and X is $NCH_3$.

In various embodiments of the first embodiment of the compound of formula (2), at least one $R^1$ is H in one embodiment, each $R^1$ is H in another embodiment, at least one of $R^1$ is ($C_1$)alkyl in an additional embodiment, and each $R^1$ is ($C_1$)alkyl in a further embodiment.

In various embodiments of the second embodiment of the compound of formula (2), at least one $R^1$ is H in one embodiment, each $R^1$ is H in another embodiment, at least one of $R^1$ is ($C_1$)alkyl in an additional embodiment, and each $R^1$ is ($C_1$)alkyl in a further embodiment.

In various embodiments of the third embodiment of the compound of formula (2), at least one $R^1$ is H in one embodiment, each $R^1$ is H in another embodiment, at least one of $R^1$ is ($C_1$)alkyl in an additional embodiment, and each $R^1$ is ($C_1$)alkyl in a further embodiment.

In another embodiment, a nitroxyl donating compound of the disclosure is a compound of the formula (3):

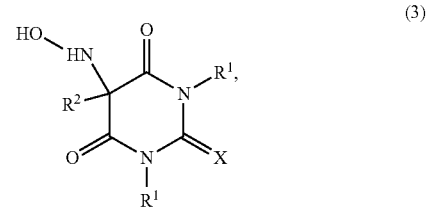

(3)

or a pharmaceutically acceptable salt thereof, wherein:

each $R^1$ is H;

$R^2$ is selected from the group consisting of ($C_1$-$C_6$)alkyl, ($C_2$-$C_6$)alkenyl, ($C_2$-$C_6$)alkynyl and ($C_1$-$C_6$)alkoxy, wherein said alkyl, alkenyl, alkynyl and alkoxy are unsubstituted or substituted with 1, 2 or 3 substituents selected from $R^4$;

X is O, $NR^7$ or S;

each $R^4$ is independently selected from the group consisting of halo, —OH, —$CH_2OH$, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(NH)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl; and $R^7$ is H or ($C_1$-$C_6$)alkyl.

According to one embodiment, $R^2$ is ($C_1$-$C_6$)alkyl, wherein said alkyl is unsubstituted or substituted with 1, 2 or 3 substituents independently selected from $R^4$. In one embodiment, $R^2$ is unsubstituted ($C_1$-$C_6$)alkyl. In another embodiment, $R^2$ is ($C_1$-$C_4$)alkyl, wherein said alkyl is unsubstituted or substituted with 1, 2 or 3 substituents independently selected from $R^4$. In another embodiment, $R^2$ is unsubstituted ($C_1$-$C_4$)alkyl. In another embodiment, $R^2$ is ($C_2$-$C_6$)alkyl, wherein said alkyl is unsubstituted or substituted with 1, 2 or 3 substituents independently selected from $R^4$. In another embodiment, $R^2$ is unsubstituted $(C_2-C_6)$ alkyl. In one embodiment, $R^2$ is methyl. In another embodiment, $R^2$ is ethyl. In another embodiment, $R^2$ is propyl. In another embodiment, $R^2$ is butyl. In another embodiment, $R^2$ is pentyl. In another embodiment, $R^2$ is hexyl.

In one embodiment, $R^2$ is $(C_1-C_6)$alkyl substituted with 1, 2 or 3 substituents independently selected from $R^4$. In another embodiment, $R^2$ is a monosubstituted $(C_1-C_6)$alkyl substituted with a substituent selected from $R^4$. In another embodiments, $R^2$ is a disubstituted $(C_1-C_6)$alkyl substituted with 2 substituents independently selected from $R^4$. In another embodiments, $R^2$ is a trisubstituted $(C_1-C_6)$alkyl substituted with 3 substituents independently selected from $R^4$. In one embodiment, $R^2$ is $(C_1-C_6)$alkyl substituted 1, 2 or 3 substituents independently selected from halo, SR', —C(O)NH$_2$, —C(O)OH, —NH$_2$ and —NH—C(NH)—NH$_2$. In another embodiment, $R^2$ is $(C_1-C_6)$alkyl monosubstituted with halo. In another embodiment, $R^2$ is $(C_1-C_6)$alkyl disubstituted with 2 halos independently selected. In another embodiment, $R^2$ is $(C_1-C_6)$alkyl trisubstituted with 3 halos independently selected. In another embodiment, $R^2$ is $(C_1-C_6)$alkyl monosubstituted with fluoro. In another embodiment, $R^2$ is $(C_1-C_6)$alkyl disubstituted with fluoro. In another embodiment, $R^2$ is $(C_1-C_6)$alkyl trisubstituted fluoro. In another embodiment, $R^2$ is $(C_1-C_6)$alkyl monosubstituted with SR'. In another embodiment, $R^2$ is $(C_1-C_6)$alkyl monosubstituted with S$(C_1-C_6)$alkyl. In another embodiment, $R^2$ is $(C_1-C_6)$alkyl monosubstituted with —SCH$_3$. In another embodiment, $R^2$ is $(C_1-C_6)$alkyl monosubstituted with —C(O)NH$_2$. In another embodiment, $R^2$ is $(C_1-C_6)$alkyl monosubstituted with —C(O)OH. In another embodiment, $R^2$ is $(C_1-C_6)$alkyl monosubstituted with —NH$_2$. In another embodiment, $R^2$ is $(C_1-C_6)$alkyl monosubstituted with —NH—C(NH)—NH$_2$.

In one embodiment, $R^2$ is a $(C_1-C_4)$alkyl substituted with 1, 2 or 3 substituents independently selected from $R^4$. In another embodiment, $R^2$ is a monosubstituted $(C_1-C_4)$alkyl substituted with a substituent independently selected from $R^4$. In another embodiments, $R^2$ is a disubstituted $(C_1-C_4)$ alkyl substituted with 2 substituents independently selected from $R^4$. In another embodiments, $R^2$ is a trisubstituted $(C_1-C_4)$alkyl substituted with 3 substituents independently selected from $R^4$. In one embodiment, $R^2$ is $(C_1-C_4)$alkyl substituted 1, 2 or 3 substituents independently selected from halo, SR', —C(O)NH$_2$, —C(O)OH, —NH$_2$ and —NH—C(NH)—NH$_2$. In another embodiment, $R^2$ is $(C_1-C_4)$alkyl monosubstituted with halo. In another embodiment, $R^2$ is $(C_1-C_4)$alkyl disubstituted with 2 halos independently selected. In another embodiment, $R^2$ is $(C_1-C_4)$alkyl trisubstituted with 3 halos independently selected. In another embodiment, $R^2$ is $(C_1-C_4)$alkyl monosubstituted with fluoro. In another embodiment, $R^2$ is $(C_1-C_4)$alkyl disubstituted with fluoro. In another embodiment, $R^2$ is $(C_1-C_4)$alkyl trisubstituted fluoro. In another embodiment, $R^2$ is $(C_1-C_4)$alkyl monosubstituted with SR'. In another embodiment, $R^2$ is $(C_1-C_4)$alkyl monosubstituted with S$(C_1-C_6)$alkyl. In another embodiment, $R^2$ is $(C_1-C_4)$alkyl monosubstituted with —SCH$_3$. In another embodiment, $R^2$ is $(C_1-C_4)$alkyl monosubstituted with —C(O)NH$_2$. In another embodiment, $R^2$ is $(C_1-C_4)$alkyl monosubstituted with —C(O)OH. In another embodiment, $R^2$ is $(C_1-C_4)$alkyl monosubstituted with —NH$_2$. In another embodiment, $R^2$ is $(C_1-C_4)$alkyl monosubstituted with —NH—C(NH)—NH$_2$.

In one embodiment, $R^2$ is a $(C_2-C_6)$alkyl substituted with 1, 2 or 3 substituents independently selected from $R^4$. In another embodiment, $R^2$ is a monosubstituted $(C_2-C_6)$alkyl substituted with a substituent independently selected from $R^4$. In another embodiments, $R^2$ is a disubstituted $(C_2-C_6)$ alkyl substituted with 2 substituents independently selected from $R^4$. In another embodiments, $R^2$ is a trisubstituted $(C_2-C_6)$alkyl substituted with 3 substituents independently selected from $R^4$. In one embodiment, $R^2$ is $(C_2-C_6)$alkyl substituted 1, 2 or 3 substituents independently selected from halo, SR', —C(O)NH$_2$, —C(O)OH, —NH$_2$ and —NH—C(NH)—NH$_2$. In another embodiment, $R^2$ is $(C_2-C_6)$alkyl monosubstituted with halo. In another embodiment, $R^2$ is $(C_2-C_6)$alkyl disubstituted with 2 halos independently selected. In another embodiment, $R^2$ is $(C_2-C_6)$alkyl trisubstituted with 3 halos independently selected. In another embodiment, $R^2$ is $(C_2-C_6)$alkyl monosubstituted with fluoro. In another embodiment, $R^2$ is $(C_2-C_6)$alkyl disubstituted with fluoro. In another embodiment, $R^2$ is $(C_2-C_6)$alkyl trisubstituted with fluoro. In another embodiment, $R^2$ is $(C_2-C_6)$alkyl monosubstituted with SR'. In another embodiment, $R^2$ is $(C_2-C_6)$alkyl monosubstituted with S$(C_1-C_6)$alkyl. In another embodiment, $R^2$ is $(C_2-C_6)$alkyl monosubstituted with —SCH$_3$. In another embodiment, $R^2$ is $(C_2-C_6)$alkyl monosubstituted with —C(O)NH$_2$. In another embodiment, $R^2$ is $(C_2-C_6)$alkyl monosubstituted with —C(O)OH. In another embodiment, $R^2$ is $(C_2-C_6)$alkyl monosubstituted with —NH$_2$. In another embodiment, $R^2$ is $(C_2-C_6)$alkyl monosubstituted with —NH—C(NH)—NH$_2$.

In one embodiment, $R^2$ is a monosubstituted $(C_1)$alkyl substituted with a substituent selected from $R^4$. In another embodiment, $R^2$ is $(C_1)$alkyl monosubstituted with a substituent selected from halo, SR', —C(O)NH$_2$, —C(O)OH, —NH$_2$ and —NH—C(NH)—NH$_2$. In another embodiment, $R^2$ is $(C_1)$alkyl monosubstituted with halo. In another embodiment, $R^2$ is $(C_1)$alkyl monosubstituted with fluoro. In another embodiment, $R^2$ is $(C_1)$alkyl monosubstituted with SR'. In another embodiment, $R^2$ is $(C_1)$alkyl monosubstituted with S$(C_1-C_6)$alkyl. In another embodiment, $R^2$ is $(C_1)$alkyl monosubstituted with —SCH$_3$. In another embodiment, $R^2$ is $(C_1)$alkyl monosubstituted with —C(O)NH$_2$. In another embodiment, $R^2$ is $(C_1)$alkyl monosubstituted with —C(O)OH. In another embodiment, $R^2$ is $(C_1)$alkyl monosubstituted with —NH$_2$. In another embodiment, $R^2$ is $(C_1)$alkyl monosubstituted with —NH—C(NH)—NH$_2$. In another embodiments, $R^2$ is a disubstituted $(C_1)$alkyl substituted with 2 halos independently selected. In another embodiment, $R^2$ is $(C_1)$alkyl disubstituted with fluoro. In another embodiment, $R^2$ is $(C_1)$alkyl trisubstituted with 3 halos independently selected. In another embodiment, $R^2$ is $(C_1)$alkyl trisubstituted with fluoro.

In one embodiment, $R^2$ is a monosubstituted $(C_2)$alkyl substituted with a substituent selected from $R^4$. In another embodiment, $R^2$ is $(C_2)$alkyl monosubstituted with a substituent selected from halo, SR', —C(O)NH$_2$, —C(O)OH, —NH$_2$ and —NH—C(NH)—NH$_2$. In another embodiment, $R^2$ is $(C_2)$alkyl monosubstituted with halo. In another embodiment, $R^2$ is $(C_2)$alkyl monosubstituted with fluoro. In another embodiment, $R^2$ is $(C_2)$alkyl monosubstituted with SR'. In another embodiment, $R^2$ is $(C_2)$alkyl monosubstituted with S$(C_1-C_6)$alkyl. In another embodiment, $R^2$ is $(C_2)$alkyl monosubstituted with —SCH$_3$. In another embodiment, $R^2$ is $(C_2)$alkyl monosubstituted with —C(O)NH$_2$. In another embodiment, $R^2$ is $(C_2)$alkyl monosubstituted with —C(O)OH. In another embodiment, $R^2$ is $(C_2)$alkyl monosubstituted with —NH$_2$. In another embodiment, $R^2$ is $(C_2)$alkyl monosubstituted with —NH—C(NH)—NH$_2$. In another embodiments, $R^2$ is a disubstituted $(C_2)$alkyl substituted with 2 halos independently selected. In another embodiment, $R^2$ is $(C_2)$alkyl disubstituted with fluoro. In another embodiment, $R^2$ is ($C_2$)alkyl trisubstituted with 3 halos independently selected. In another embodiment, $R^2$ is ($C_2$)alkyl trisubstituted with fluoro.

In one embodiment, $R^2$ is a monosubstituted ($C_3$)alkyl substituted with a substituent selected from $R^4$. In another embodiment, $R^2$ is ($C_3$)alkyl monosubstituted with a substituent selected from halo, SR', —C(O)$NH_2$, —C(O)OH, —$NH_2$ and —NH—C(NH)—$NH_2$. In another embodiment, $R^2$ is ($C_3$)alkyl monosubstituted with halo. In another embodiment, $R^2$ is ($C_3$)alkyl monosubstituted with fluoro. In another embodiment, $R^2$ is ($C_3$)alkyl monosubstituted with SR'. In another embodiment, $R^2$ is ($C_3$)alkyl monosubstituted with S($C_1$-$C_6$)alkyl. In another embodiment, $R^2$ is ($C_3$)alkyl monosubstituted with —$SCH_3$. In another embodiment, $R^2$ is ($C_3$)alkyl monosubstituted with —C(O)$NH_2$. In another embodiment, $R^2$ is ($C_3$)alkyl monosubstituted with —C(O)OH. In another embodiment, $R^2$ is ($C_3$) alkyl monosubstituted with —$NH_2$. In another embodiment, $R^2$ is ($C_3$)alkyl monosubstituted with —NH—C(NH)—$NH_2$. In another embodiments, $R^2$ is a disubstituted ($C_3$) alkyl substituted with 2 halos independently selected. In another embodiment, $R^2$ is ($C_3$)alkyl disubstituted with fluoro. In another embodiment, $R^2$ is ($C_3$)alkyl trisubstituted with 3 halos independently selected. In another embodiment, $R^2$ is ($C_3$)alkyl trisubstituted with fluoro.

In one embodiment, $R^2$ is a monosubstituted ($C_4$)alkyl substituted with a substituent selected from $R^4$. In another embodiment, $R^2$ is ($C_4$)alkyl monosubstituted with a substituent selected from halo, SR', —C(O)$NH_2$, —C(O)OH, —$NH_2$ and —NH—C(NH)—$NH_2$. In another embodiment, $R^2$ is ($C_4$)alkyl monosubstituted with halo. In another embodiment, $R^2$ is ($C_4$)alkyl monosubstituted with fluoro. In another embodiment, $R^2$ is ($C_4$)alkyl monosubstituted with SR'. In another embodiment, $R^2$ is ($C_4$)alkyl monosubstituted with S($C_1$-$C_6$)alkyl. In another embodiment, $R^2$ is ($C_4$)alkyl monosubstituted with —$SCH_3$. In another embodiment, $R^2$ is ($C_4$)alkyl monosubstituted with —C(O)$NH_2$. In another embodiment, $R^2$ is ($C_4$)alkyl monosubstituted with —C(O)OH. In another embodiment, $R^2$ is ($C_4$) alkyl monosubstituted with —$NH_2$. In another embodiment, $R^2$ is ($C_4$)alkyl monosubstituted with —NH—C(NH)—$NH_2$. In another embodiments, $R^2$ is a disubstituted ($C_4$) alkyl substituted with 2 halos independently selected. In another embodiment, $R^2$ is ($C_4$)alkyl disubstituted with fluoro. In another embodiment, $R^2$ is ($C_4$)alkyl trisubstituted with 3 halos independently selected. In another embodiment, $R^2$ is ($C_4$)alkyl trisubstituted with fluoro.

According to a second embodiment, $R^2$ is a branched ($C_3$-$C_6$)alkyl, wherein said alkyl is unsubstituted or substituted with 1, 2 or 3 substituents selected from $R^4$. In one embodiment, $R^2$ is a substituted, branched $C_3$-$C_6$ alkyl. In another embodiment, $R^2$ is an unsubstituted, branched $C_3$-$C_6$ alkyl. In one embodiment, $R^2$ is selected from the group consisting of iso-propyl, sec-butyl, iso-butyl, tert-butyl, methylpentyl, ethylbutyl, dimethylbutyl, and iso-propylpropyl. In other embodiments, $R^2$ is selected from the group consisting of sec-butyl, iso-butyl, tert-butyl, methylpentyl, ethylbutyl, dimethylbutyl, and iso-propylpropyl.

According to a third embodiment, $R^2$ is ($C_2$-$C_6$)alkenyl, wherein said alkenyl is unsubstituted or substituted with 1, 2 or 3 substituents selected from $R^4$. In some embodiments, $R^2$ is a substituted ($C_2$-$C_6$)alkenyl. In other embodiments, $R^2$ is an unsubstituted ($C_2$-$C_6$)alkenyl. In one embodiment, $R^2$ is an unsubstituted ($C_3$-$C_6$)alkenyl. In another embodiment, $R^2$ is an unsubstituted ($C_3$)alkenyl. In another embodiment, $R^2$ is an unsubstituted ($C_4$)alkenyl. In another embodiment, $R^2$ is an unsubstituted ($C_5$)alkenyl. In another embodiment, $R^2$ is an unsubstituted ($C_6$)alkenyl. In one embodiment, $R^2$ is a substituted ($C_3$-$C_6$)alkenyl. In another embodiment, $R^2$ is a substituted ($C_3$)alkenyl. In another embodiment, $R^2$ is a substituted ($C_4$)alkenyl. In another embodiment, $R^2$ is a substituted ($C_5$)alkenyl. In another embodiment, $R^2$ is a substituted ($C_6$)alkenyl.

According to a fourth embodiment, $R^2$ is a branched ($C_3$-$C_6$)alkenyl, wherein said alkenyl is unsubstituted or substituted with 1, 2 or 3 substituents selected from $R^4$. In one embodiment, $R^2$ is a substituted, branched ($C_3$-$C_6$) alkenyl. In another embodiment, $R^2$ is an unsubstituted, branched ($C_3$-$C_6$)alkenyl. In one embodiment, $R^2$ is an unsubstituted, branched ($C_3$-$C_6$)alkenyl. In another embodiment, $R^2$ is an unsubstituted, branched ($C_3$)alkenyl. In another embodiment, $R^2$ is an unsubstituted, branched ($C_4$) alkenyl. In another embodiment, $R^2$ is an unsubstituted, branched ($C_5$)alkenyl. In another embodiment, $R^2$ is an unsubstituted, branched ($C_6$)alkenyl. In one embodiment, $R^2$ is a substituted, branched ($C_3$-$C_6$)alkenyl. In another embodiment, $R^2$ is a substituted, branched ($C_3$)alkenyl. In another embodiment, $R^2$ is a substituted, branched ($C_4$) alkenyl. In another embodiment, $R^2$ is a substituted, branched ($C_5$)alkenyl. In another embodiment, $R^2$ is a substituted, branched ($C_6$)alkenyl.

According to a fifth embodiment, $R^2$ is ($C_2$-$C_6$)alkynyl, wherein said alkynyl is unsubstituted or substituted with 1, 2 or 3 substituents selected from $R^4$. In some embodiments, $R^2$ is a substituted ($C_2$-$C_6$)alkynyl. In other embodiments, $R^2$ is an unsubstituted ($C_2$-$C_6$)alkynyl. In one embodiment, $R^2$ is an unsubstituted, branched ($C_3$-$C_6$)alkynyl. In another embodiment, $R^2$ is an unsubstituted, branched ($C_3$) alkynyl. In another embodiment, $R^2$ is an unsubstituted, branched ($C_4$) alkynyl. In another embodiment, $R^2$ is an unsubstituted, branched ($C_5$) alkynyl. In another embodiment, $R^2$ is an unsubstituted, branched ($C_6$)alkynyl. In one embodiment, $R^2$ is a substituted, branched ($C_3$-$C_6$)alkynyl. In another embodiment, $R^2$ is a substituted, branched ($C_3$)alkynyl. In another embodiment, $R^2$ is a substituted, branched ($C_4$) alkynyl. In another embodiment, $R^2$ is a substituted, branched ($C_5$)alkynyl. In another embodiment, $R^2$ is a substituted, branched ($C_6$)alkynyl.

According to sixth embodiment, $R^2$ is ($C_1$-$C_6$)alkoxy, wherein said alkoxy is unsubstituted or substituted with 1, 2 or 3 substituents selected from $R^4$. In some embodiments, $R^2$ is a substituted ($C_1$-$C_6$)alkoxy. In other embodiments, $R^2$ is an unsubstituted ($C_1$-$C_6$)alkoxy. In one embodiment, $R^2$ is methoxy. In another embodiment, $R^2$ is ethoxy. In another embodiment, $R^2$ is propoxy.

According to an seventh embodiment, $R^2$ is a branched ($C_3$-$C_6$)alkoxy, wherein said alkoxy is unsubstituted or substituted with 1, 2 or 3 substituents selected from $R^4$. In one embodiment, $R^2$ is a substituted, branched ($C_3$-$C_6$)alkoxy. In another embodiment, $R^2$ is an unsubstituted, branched ($C_3$-$C_6$)alkoxy.

In some aspects of this embodiment, X is S. In other aspects, X is O. In other aspects, X is NH. In other aspects, X is N($C_1$-$C_6$)alkyl. In other aspects, X is $NCH_3$.

In various embodiments of the first embodiment of the compound of formula (3), X is S in one embodiment, X is O in another embodiment, X is NH in an additional embodiment and X is $NCH_3$ in a further embodiment.

In various embodiments of the second embodiment of the compound of formula (3), X is S in one embodiment, X is O in another embodiment, X is NH in an additional embodiment and X is $NCH_3$ in a further embodiment.

In various embodiments of the third embodiment of the compound of formula (3), X is S in one embodiment, X is O in another embodiment, X is NH in an additional embodiment and X is NCH$_3$ in a further embodiment.

In various embodiments of the fourth embodiment of the compound of formula (3), X is S in one embodiment, X is O in another embodiment, X is NH in an additional embodiment and X is NCH$_3$ in a further embodiment.

In various embodiments of the fifth embodiment of the compound of formula (3), X is S in one embodiment, X is O in another embodiment, X is NH in an additional embodiment and X is NCH$_3$ in a further embodiment.

In various embodiments of the sixth embodiment of the compound of formula (3), X is S in one embodiment, X is O in another embodiment, X is NH in an additional embodiment and X is NCH$_3$ in a further embodiment.

In various embodiments of the seventh embodiment of the compound of formula (3), X is S in one embodiment, X is O in another embodiment, X is NH in an additional embodiment and X is NCH$_3$ in a further embodiment.

According to one aspect of this embodiment, a nitroxyl donating compound of the disclosure is a compound of the formula (3a):

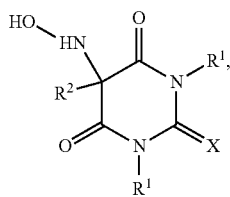

or a pharmaceutically acceptable salt thereof, wherein:
each $R^1$ is H;
$R^2$ is $(C_1-C_4)$alkyl substituted with phenyl, wherein said phenyl is unsubstituted or substituted with 1, 2, 3, 4 or 5 substituents selected from $R^4$ and said alkyl is unsubstituted or substituted with 1, 2 or 3 substituents selected from $R^6$;
X is O, $NR^7$ or S;
each $R^4$ is independently selected from the group consisting of halo, —OH, —NH$_2$, —C≡N, —NO$_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl;
each $R^6$ is independently selected from the group consisting of halo and $(C_1-C_6)$alkyl; and
$R^7$ is H or $(C_1-C_6)$alkyl.

In one embodiment, $R^2$ is $(C_1-C_4)$alkyl substituted with phenyl. In another embodiment, $R^2$ is $(C_1-C_2)$alkyl substituted with phenyl. In another embodiment, $R^2$ is $(C_1)$alkyl substituted with phenyl. In each embodiment of this paragraph, the phenyl is unsubstituted in one embodiment, mono-substituted in another embodiment, di-substituted with two independently selected substituents in an additional embodiment, or tri-substituted with three independently selected substituents in a further embodiment.

In embodiments in which said $(C_1-C_4)$alkyl is substituted with $R^6$, $R^6$ is halo or $(C_1-C_6)$alkyl. In some embodiments, halo or $(C_1-C_4)$alkyl. In other embodiments, $R^6$ is halo or $(C_1-C_2)$alkyl. In other embodiments, $R^6$ is fluoro. In other embodiments, $R^6$ is methyl.

In embodiments in which said phenyl is substituted, each $R^4$ is independently selected from the group consisting of halo, —OH, —NH$_2$, —C≡N, —NO$_2$, —SH, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', —C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl.

In some embodiments, each $R^4$ is independently selected from the group consisting of —OH, —NH$_2$, —SH, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —NHR', —NR'R", —SR', —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl.

In another embodiment, each $R^4$ is independently selected from the group consisting of —OH, —NH$_2$, —SH, $(C_1-C_6)$alkyl, $(C_2-C_6)$alkenyl, $(C_2-C_6)$alkynyl, $(C_1-C_6)$alkoxy, $(C_2-C_6)$alkenyloxy and $(C_2-C_6)$alkynyloxy. In some embodiments, each $R^4$ is independently selected from the group consisting of —OH, —NH$_2$, —SH, $(C_1-C_6)$alkoxy, $(C_2-C_6)$alkenyloxy and $(C_2-C_6)$alkynyloxy. In other embodiments, each $R^4$ is independently selected from the group consisting of $(C_1-C_6)$alkoxy, $(C_2-C_6)$alkenyloxy and $(C_2-C_6)$alkynyloxy. In yet other embodiments, $R^4$ is $(C_1-C_6)$alkoxy. In some embodiments, $R^4$ is selected $(C_1-C_3)$alkoxy. In other embodiments, $R^4$ is methoxy. In other embodiments, $R^4$ is —OH.

In some embodiments, each $R^4$ is independently selected from the group consisting of halo, —C≡N, —NO$_2$, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', —C(O)NHR', —C(O)NR'R", —S(O)R' and —S(O)OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl, and $(C_5-C_7)$heterocycloalkyl.

In another embodiment, each $R^4$ is independently selected from the group consisting of halo, —C≡N, —NO$_2$, —C(O)NH$_2$, —C(O)OH, —COR', —C(O)OR', —C(O)NHR', and —C(O)NR'R", wherein $R^1$ and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl. In some embodiments, $R^4$ is halo. In some embodiments, $R^4$ is Cl.

In some aspects of this embodiment, X is S. In other aspects, X is O. In other aspects, X is NH. In other aspects, X is N$(C_1-C_6)$alkyl. In other aspects, X is NCH$_3$.

In one embodiment, $R^2$ is $(C_1-C_4)$alkyl substituted with phenyl and X is S. In another embodiment, $R^2$ is $(C_1-C_4)$alkyl substituted with phenyl and X is O. In another embodiment, $R^2$ is $(C_1-C_4)$alkyl substituted with phenyl and X is NH. In another embodiment, $R^2$ is $(C_1-C_4)$alkyl substituted with phenyl and X is NCH₃. In each embodiment of this paragraph, the phenyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, halo, or methylsulfonyl, or the substituents are independently selected from methoxy, halo, and methylsulfonyl.

In one embodiment, $R^2$ is $(C_1$-$C_2)$alkyl substituted with phenyl and X is S. In another embodiment, $R^2$ is $(C_1$-$C_2)$ alkyl substituted with phenyl and X is O. In another embodiment, $R^2$ is $(C_1$-$C_2)$alkyl substituted with phenyl and X is NH. In another embodiment, $R^2$ is $(C_1$-$C_2)$alkyl substituted with phenyl and X is NCH₃. In each embodiment of this paragraph, the phenyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is —OH, methoxy, halo, or methylsulfonyl, or the substituents are independently selected from —OH, methoxy, halo, and methylsulfonyl.

In one embodiment, $R^2$ is $(C_1)$alkyl substituted with phenyl and X is S. In another embodiment, $R^2$ is $(C_1)$alkyl substituted with phenyl and X is O. In another embodiment, $R^2$ is $(C_1)$alkyl substituted with phenyl and X is NH. In another embodiment, $R^2$ is $(C_1)$alkyl substituted with phenyl and X is NCH₃. In each embodiment of this paragraph, the phenyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is —OH, methoxy, halo, or methylsulfonyl, or the substituents are independently selected from —OH, methoxy, halo, and methylsulfonyl.

In another embodiment, a nitroxyl donating compound of the disclosure is a compound of the formula (3a-1):

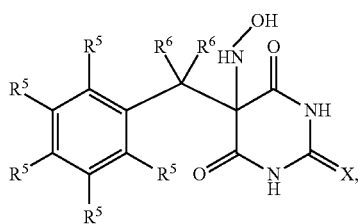

(3a-1)

or a pharmaceutically acceptable salt thereof, wherein:
each $R^5$ is selected from the group consisting of H, halo, —OH, —NH₂, —C≡N, —NO₂, —SH, =O, =S, =N—$(C_1$-$C_4)$alkyl, $(C_1$-$C_6)$alkyl, $(C_2$-$C_6)$alkenyl, $(C_2$-$C_6)$alkynyl, $(C_1$-$C_6)$alkoxy, $(C_2$-$C_6)$alkenyloxy, $(C_2$-$C_6)$alkynyloxy, $(C_6$-$C_{14})$aryl, $(C_3$-$C_6)$cycloalkyl, (5- or 6-membered)heteroaryl, $(C_5$-$C_7)$heterocycloalkyl, —C(O)H, —C(O)NH₂, —C(O)OH, —NH—C(O)—NH₂, —NH—C(S)—NH₂, —SC≡N, —SO₂NH₂, —COR', —C(O)OR', C(O)NHR', —C(O)NR'R", —NHR', —NR'R", —SR', —S(O)R', —S(O)OR', and —OR', wherein R' and R" are independently selected from $(C_1$-$C_6)$alkyl, $(C_2$-$C_6)$alkenyl, $(C_2$-$C_6)$ alkynyl, $(C_6$-$C_{14})$aryl, $(C_3$-$C_6)$cycloalkyl, (5- or 6-membered)heteroaryl and $(C_5$-$C_7)$heterocycloalkyl;

X is O, $NR^7$ or S;

each $R^6$ is independently selected from the group consisting of H, halo and $(C_1$-$C_6)$alkyl; and $R^7$ is H or $(C_1$-$C_6)$alkyl.

In some embodiments, one or more of $R^5$ is selected from the group consisting of H, —OH, $(C_1$-$C_6)$alkoxy, S(O)O($C_1$-$C_6$)alkyl and halo. In some aspects, one or more of $R^5$ is selected from the group consisting of —OH, $(C_1$-$C_6)$alkoxy, S(O)O($C_1$-$C_6$)alkyl and halo. In some aspects, one or more of $R^5$ is methoxy. In other aspects, one or more of $R^5$ is Cl. In some aspects, one or more of $R^5$ is S(O)O($C_1$-$C_6$)alkyl. In another embodiment, one or more of $R^5$ is —OH.

In some aspects, one $R^5$ is methoxy and the other $R^5$ are H. In other aspects, one $R^5$ is Cl and the other $R^5$ are H. In some aspects, one $R^5$ is S(O)O($C_1$-$C_6$)alkyl and the other $R^5$ are H. In another embodiment, one $R^5$ is —OH and the other $R^5$ are H.

In some embodiments, at least one of $R^6$ is H, halo or $(C_1$-$C_4)$alkyl. In other embodiments, at least one of $R^6$ is H, halo or $(C_1$-$C_2)$alkyl. In other embodiments, at least one of $R^6$ is fluoro. In other embodiments, at least one of $R^6$ is methyl. In other embodiments, at least one of $R^6$ is H.

In some aspects of this embodiment, X is S. In other aspects, X is O. In other aspects, X is NH. In other aspects, X is N($C_1$-$C_6)$alkyl. In other aspects, X is NCH₃.

According to one aspect of this embodiment, a nitroxyl donating compound of the disclosure is a compound of the formula (3b):

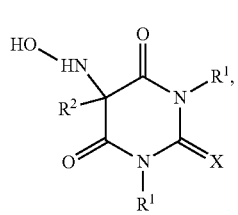

(3b)

or a pharmaceutically acceptable salt thereof, wherein:
each $R^1$ is H;
$R^2$ is $(C_1$-$C_4)$alkyl substituted with $(C_3$-$C_6)$cycloalkyl, wherein said cycloalkyl is unsubstituted or substituted with 1, 2 or 3 substituents selected from $R^4$ and said alkyl is unsubstituted or substituted with 1, 2 or 3 substituents selected from $R^6$;
each $R^4$ is independently selected from the group consisting of halo, —OH, —NH₂, —C≡N, —NO₂, —SH, =O, =S, =N—$(C_1$-$C_4)$alkyl, $(C_1$-$C_6)$alkyl, $(C_2$-$C_6)$ alkenyl, $(C_2$-$C_6)$alkynyl, $(C_1$-$C_6)$alkoxy, $(C_2$-$C_6)$alkenyloxy, $(C_2$-$C_6)$alkynyloxy, $(C_6$-$C_{14})$aryl, $(C_3$-$C_6)$cycloalkyl, (5- or 6-membered)heteroaryl, $(C_5$-$C_7)$ heterocycloalkyl, —C(O)H, —C(O)NH₂, —C(O)OH, —NH—C(O)—NH₂, —NH—C(S)—NH₂, —SC≡N, —SO₂NH₂, —COR', —C(O)OR', C(O)NHR', —C(O)NR'R", —NHR', —NR'R", —SR', —S(O)R', —S(O)OR', and —OR', wherein R' and R" are independently selected from $(C_1$-$C_6)$alkyl, $(C_2$-$C_6)$alkenyl, $(C_2$-$C_6)$ alkynyl, $(C_6$-$C_{14})$aryl, $(C_3$-$C_6)$cycloalkyl, (5- or 6-membered)heteroaryl and $(C_5$-$C_7)$heterocycloalkyl;
X is O, $NR^7$ or S;
each $R^6$ is independently selected from the group consisting of halo and $(C_1$-$C_6)$alkyl; and
$R^7$ is H or $(C_1$-$C_6)$alkyl.

In one embodiment, $R^2$ is $(C_1-C_4)$alkyl substituted with $(C_3-C_6)$cycloalkyl. In another embodiment, $R^2$ is $(C_1-C_2)$ alkyl substituted with $(C_3-C_6)$cycloalkyl. In another embodiment, $R^2$ is $(C_1)$alkyl substituted with $(C_3-C_6)$cycloalkyl. In each embodiment of this paragraph, the $(C_3-C_6)$cycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the $(C_3-C_6)$cycloalkyl is selected from the group consisting of cyclopropyl, cyclobutyl, cyclopentyl and cyclohexyl. In various embodiments of each of the embodiments in this paragraph, the $(C_3-C_6)$ cycloalkyl is cyclohexyl.

In embodiments in which said $(C_1-C_4)$alkyl is substituted with $R^6$, $R^6$ is halo or $(C_1-C_6)$alkyl. In some embodiments, halo or $(C_1-C_4)$alkyl. In other embodiments, $R^6$ is halo or $(C_1-C_2)$alkyl. In other embodiments, $R^6$ is fluoro. In other embodiments, $R^6$ is methyl.

In some aspects of this embodiment, X is S. In other aspects, X is O. In other aspects, X is NH. In other aspects, X is $N(C_1-C_6)$alkyl. In other aspects, X is $NCH_3$.

In one embodiment, $R^2$ is $(C_1-C_4)$alkyl substituted with $(C_3-C_6)$cycloalkyl and X is S. In another embodiment, $R^2$ is $(C_1-C_4)$alkyl substituted with $(C_3-C_6)$cycloalkyl and X is O. In another embodiment, $R^2$ is $(C_1-C_4)$alkyl substituted with $(C_3-C_6)$cycloalkyl and X is NH. In another embodiment, $R^2$ is $(C_1-C_4)$alkyl substituted with $(C_3-C_6)$cycloalkyl and X is $NCH_3$. In each embodiment of this paragraph, the cycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, halo, or methylsulfonyl, or the substituents are independently selected from methoxy, halo, and methylsulfonyl.

In one embodiment, $R^2$ is $(C_1-C_2)$alkyl substituted with $(C_3-C_6)$cycloalkyl and X is S. In another embodiment, $R^2$ is $(C_1-C_2)$alkyl substituted with $(C_3-C_6)$cycloalkyl and X is O. In another embodiment, $R^2$ is $(C_1-C_2)$alkyl substituted with $(C_3-C_6)$cycloalkyl and X is NH. In another embodiment, $R^2$ is $(C_1-C_2)$alkyl substituted with $(C_3-C_6)$cycloalkyl and X is $NCH_3$. In each embodiment of this paragraph, the cycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, halo, or methylsulfonyl, or the substituents are independently selected from methoxy, halo, and methylsulfonyl.

In one embodiment, $R^2$ is $(C_1)$alkyl substituted with $(C_3-C_6)$cycloalkyl and X is S. In another embodiment, $R^2$ is $(C_1)$alkyl substituted with $(C_3-C_6)$cycloalkyl and X is O. In another embodiment, $R^2$ is $(C_1)$alkyl substituted with $(C_3-C_6)$cycloalkyl and X is NH. In another embodiment, $R^2$ is $(C_1)$alkyl substituted with $(C_3-C_6)$cycloalkyl and X is $NCH_3$. In each embodiment of this paragraph, the cycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, halo, or methylsulfonyl, or the substituents are independently selected from methoxy, halo, and methylsulfonyl.

According to one aspect of this embodiment, a nitroxyl donating compound of the disclosure is a compound of the formula (3c):

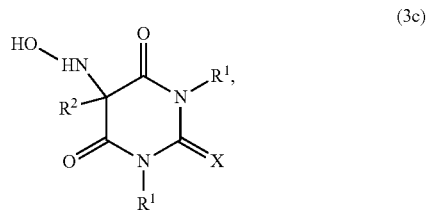

(3c)

or a pharmaceutically acceptable salt thereof, wherein:
each $R^1$ is H;
$R^2$ is $(C_1-C_4)$alkyl substituted with $(C_5-C_7)$heterocycloalkyl, wherein said heterocycloalkyl is unsubstituted or substituted with 1, 2, 3, 4 or 5 substituents selected from $R^4$ and said alkyl is unsubstituted or substituted with 1, 2 or 3 substituents selected from $R^6$;
X is O, $NR^7$ or S;
each $R^4$ is independently selected from the group consisting of halo, —OH, —$NH_2$, —C≡N, —$NO_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl;
each $R^6$ is independently selected from the group consisting of halo and $(C_1-C_6)$alkyl; and
$R^7$ is H or $(C_1-C_6)$alkyl.

In one embodiment, $R^2$ is $(C_1-C_4)$alkyl substituted with $(C_5-C_7)$heterocycloalkyl. In another embodiment, $R^2$ is $(C_1-C_2)$alkyl substituted with $(C_5-C_7)$heterocycloalkyl. In another embodiment, $R^2$ is $(C_1)$alkyl substituted with $(C_5-C_7)$heterocycloalkyl. In each embodiment of this paragraph, the heterocycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heterocycloalkyl is selected from the group consisting of pyrrolidinyl, piperidinyl, piperazinyl, tetrahydro-oxazinyl, tetrahydrofuran, thiolane, dithiolane, pyrroline, pyrrolidine, pyrazoline, pyrazolidine, imidazoline, imidazolidine, tetrahydrofuranone, γ-butyrolactone, 2H-pyran, 4H-pyran, dioxolane, tetrahydropyran, dioxane, dihydrothiophene, piperazine, morpholine, thiomorpholine, oxazine and tetrahydro-oxazinyl.

In one embodiment, the heterocycloalkyl is a $(C_6)$heterocycloalkyl selected from the group consisting of piperidinyl, piperazinyl, tetrahydro-oxazinyl, tetrahydropyran, dioxane, morpholine and thiomorpholine.

In embodiments in which said $(C_1-C_4)$alkyl is substituted with $R^6$, $R^6$ is halo or $(C_1-C_6)$alkyl. In some embodiments, halo or $(C_1-C_4)$alkyl. In other embodiments, $R^6$ is halo or $(C_1-C_2)$alkyl. In other embodiments, $R^6$ is fluoro. In other embodiments, $R^6$ is methyl.

In some aspects of this embodiment, X is S. In other aspects, X is O. In other aspects, X is NH. In other aspects, X is N($C_1$-$C_6$)alkyl. In other aspects, X is $NCH_3$.

In one embodiment, $R^2$ is ($C_1$-$C_4$)alkyl substituted with ($C_5$-$C_7$)heterocycloalkyl and X is S. In another embodiment, $R^2$ is ($C_1$-$C_4$)alkyl substituted with ($C_5$-$C_7$)heterocycloalkyl and X is O. In another embodiment, $R^2$ is ($C_1$-$C_4$)alkyl substituted with ($C_5$-$C_7$)heterocycloalkyl and X is NH. In another embodiment, $R^2$ is ($C_1$-$C_4$)alkyl substituted with ($C_5$-$C_7$)heterocycloalkyl and X is $NCH_3$. In each embodiment of this paragraph, the heterocycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, halo, or methylsulfonyl, or the substituents are independently selected from methoxy, halo, and methylsulfonyl.

In one embodiment, $R^2$ is ($C_1$-$C_2$)alkyl substituted with ($C_5$-$C_7$)heterocycloalkyl and X is S. In another embodiment, $R^2$ is ($C_1$-$C_2$)alkyl substituted with ($C_5$-$C_7$)heterocycloalkyl and X is O. In another embodiment, $R^2$ is ($C_1$-$C_2$)alkyl substituted with ($C_5$-$C_7$)heterocycloalkyl and X is NH. In another embodiment, $R^2$ is ($C_1$-$C_2$)alkyl substituted with ($C_5$-$C_7$)heterocycloalkyl and X is $NCH_3$. In each embodiment of this paragraph, the heterocycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, halo, or methylsulfonyl, or the substituents are independently selected from methoxy, halo, and methylsulfonyl.

In one embodiment, $R^2$ is ($C_1$)alkyl substituted with ($C_5$-$C_7$)heterocycloalkyl and X is S. In another embodiment, $R^2$ is ($C_1$)alkyl substituted with ($C_5$-$C_7$)heterocycloalkyl and X is O. In another embodiment, $R^2$ is ($C_1$)alkyl substituted with ($C_5$-$C_7$)heterocycloalkyl and X is NH. In another embodiment, $R^2$ is ($C_1$)alkyl substituted with ($C_5$-$C_7$)heterocycloalkyl and X is $NCH_3$. In each embodiment of this paragraph, the heterocycloalkyl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, halo, or methylsulfonyl, or the substituents are independently selected from methoxy, halo, and methylsulfonyl.

According to one aspect of this embodiment, a nitroxyl donating compound of the disclosure is a compound of the formula (3d):

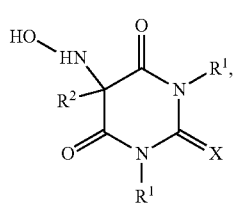

(3d)

or a pharmaceutically acceptable salt thereof, wherein:
each $R^1$ is H;
$R^2$ is ($C_1$-$C_4$)alkyl substituted with (5- or 6-membered) heteroaryl or (9- or 10-membered)heteroaryl, wherein said heteroaryl is unsubstituted or substituted with 1, 2, 3, 4 or 5 substituents selected from $R^4$ and said alkyl is unsubstituted or substituted with 1, 2 or 3 substituents selected from $R^6$;
X is O, $NR^7$ or S;
each $R^4$ is independently selected from the group consisting of halo, —OH, —$CH_2OH$, —$NH_2$, —C≡N, —$NO_2$, —SH, =O, =S, =N—($C_1$-$C_4$)alkyl, ($C_1$-$C_6$) alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O) OH, —NH—C(O)—$NH_2$, —NH—C(S)—$NH_2$, —SC≡N, —$SO_2NH_2$, —COR', —C(O)OR', C(O) NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$) alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$) heterocycloalkyl;
each $R^6$ is independently selected from the group consisting of halo and ($C_1$-$C_6$)alkyl; and
$R^7$ is H or ($C_1$-$C_6$)alkyl.

In one embodiment, $R^2$ is ($C_1$-$C_4$)alkyl substituted with (5- or 6-membered)heteroaryl or (9- or 10-membered)heteroaryl. In another embodiment, $R^2$ is ($C_1$-$C_2$)alkyl substituted with (5- or 6-membered)heteroaryl (9- or 10-membered)heteroaryl. In another embodiment, $R^2$ is ($C_1$)alkyl substituted with (5- or 6-membered)heteroaryl (9- or 10-membered)heteroaryl. In each embodiment of this paragraph, the heteroaryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the heteroaryl is a (5-membered)heteroaryl in one embodiment, a (6-membered)heteroaryl in another embodiment, a (9-membered)heteroaryl in an additional embodiment, and a (10-membered)heteroaryl in a further embodiment.

In some aspects of this embodiment, the heteroaryl is selected from the group consisting of pyridyl, pyrrolyl, pyrazolyl, furyl, thienyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, thiophenyl, indolyl, 1H-indolyl, 3-H-indolyl and benzo[d][1,3]dioxolyl.

In some embodiments, the heteroaryl is selected from the group consisting of furyl, thienyl, imidazolyl, pyridyl, pyridazinyl, pyrimidyl, pyrazinyl, 1,3,5-triazinyl, thiophenyl, indolyl, 1H-indolyl, 3-H-indolyl and benzo[d][1,3]dioxolyl. In one embodiment, the heteroaryl is furyl. In another embodiment, the heteroaryl is thienyl. In another embodiment, the heteroaryl is imidazolyl. In another embodiment, the heteroaryl is pyridyl. In another embodiment, the heteroaryl is 1H-indolyl. In another embodiment, the heteroaryl is 3H-indolyl. In another embodiment, the heteroaryl is benzo[d][1,3]dioxolyl.

In embodiments in which said ($C_1$-$C_4$)alkyl is substituted with $R^6$, $R^6$ is halo or ($C_1$-$C_6$)alkyl. In some embodiments, halo or ($C_1$-$C_4$)alkyl. In other embodiments, $R^6$ is halo or ($C_1$-$C_2$)alkyl. In other embodiments, $R^6$ is fluoro. In other embodiments, $R^6$ is methyl.

In some aspects of this embodiment, X is S. In other aspects, X is O. In other aspects, X is NH. In other aspects, X is N($C_1$-$C_6$)alkyl. In other aspects, X is $NCH_3$.

In one embodiment, R² is (C₁-C₄)alkyl substituted with (5- or 6-membered)heteroaryl or (9- or 10-membered)heteroaryl and X is S. In another embodiment, R² is (C₁-C₄)alkyl substituted with (5- or 6-membered)heteroaryl or (9- or 10-membered)heteroaryl and X is O. In another embodiment, R² is (C₁-C₄)alkyl substituted with (5- or 6-membered)heteroaryl or (9- or 10-membered)heteroaryl and X is NH. In another embodiment, R² is (C₁-C₄)alkyl substituted with (5- or 6-membered)heteroaryl or (9- or 10-membered)heteroaryl and X is NCH₃. In each embodiment of this paragraph, the heteroaryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, —CH₂OH, halo, or methylsulfonyl, or the substituents are independently selected from methoxy, —CH₂OH, halo, and methylsulfonyl. In various embodiments of each of the embodiments in this paragraph, the heteroaryl is furyl. In various embodiments of each of the embodiments in this paragraph, the heteroaryl is thienyl. In various embodiments of each of the embodiments in this paragraph, the heteroaryl is imidazolyl. In various embodiments of each of the embodiments in this paragraph, the heteroaryl is pyridyl. In various embodiments of each of the embodiments in this paragraph, the heteroaryl is 1H-indolyl. In various embodiments of each of the embodiments in this paragraph, the heteroaryl is 3H-indolyl. In various embodiments of each of the embodiments in this paragraph, the heteroaryl is benzo[d][1,3]dioxolyl.

In one embodiment, R² is (C₁-C₂)alkyl substituted with (5- or 6-membered)heteroaryl or (9- or 10-membered)heteroaryl and X is S. In another embodiment, R² is (C₁-C₂)alkyl substituted with (5- or 6-membered)heteroaryl or (9- or 10-membered)heteroaryl and X is O. In another embodiment, R² is (C₁-C₂)alkyl substituted with (5- or 6-membered)heteroaryl or (9- or 10-membered)heteroaryl and X is NH. In another embodiment, R² is (C₁-C₂)alkyl substituted with (5- or 6-membered)heteroaryl or (9- or 10-membered)heteroaryl and X is NCH₃. In each embodiment of this paragraph, the heteroaryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, —CH₂OH, halo, or methylsulfonyl, or the substituents are independently selected from methoxy, —CH₂OH, halo, and methylsulfonyl. In various embodiments of each of the embodiments in this paragraph, the heteroaryl is furyl. In various embodiments of each of the embodiments in this paragraph, the heteroaryl is thienyl. In various embodiments of each of the embodiments in this paragraph, the heteroaryl is imidazolyl. In various embodiments of each of the embodiments in this paragraph, the heteroaryl is pyridyl. In various embodiments of each of the embodiments in this paragraph, the heteroaryl is 1H-indolyl. In various embodiments of each of the embodiments in this paragraph, the heteroaryl is 3H-indolyl. In various embodiments of each of the embodiments in this paragraph, the heteroaryl is benzo[d][1,3]dioxolyl.

In one embodiment, R² is (C₁)alkyl substituted with (5- or 6-membered)heteroaryl or (9- or 10-membered)heteroaryl and X is S. In another embodiment, R² is (C₁)alkyl substituted with (5- or 6-membered)heteroaryl or (9- or 10-membered)heteroaryl and X is O. In another embodiment, R² is (C₁)alkyl substituted with (5- or 6-membered)heteroaryl or (9- or 10-membered)heteroaryl and X is NH. In another embodiment, R² is (C₁)alkyl substituted with (5- or 6-membered)heteroaryl or (9- or 10-membered)heteroaryl and X is NCH₃. In each embodiment of this paragraph, the heteroaryl is unsubstituted in one embodiment, mono-substituted in another embodiment, di-substituted with two independently selected substituents in an additional embodiment, or tri-substituted with three independently selected substituents in a further embodiment. In various embodiments of each of the embodiments in this paragraph, the substituent is methoxy, —CH₂OH, halo, or methylsulfonyl, or the substituents are independently selected from methoxy, —CH₂OH, halo, and methylsulfonyl. In various embodiments of each of the embodiments in this paragraph, the heteroaryl is furyl. In various embodiments of each of the embodiments in this paragraph, the heteroaryl is thienyl. In various embodiments of each of the embodiments in this paragraph, the heteroaryl is imidazolyl. In various embodiments of each of the embodiments in this paragraph, the heteroaryl is pyridyl. In various embodiments of each of the embodiments in this paragraph, the heteroaryl is 1H-indolyl. In various embodiments of each of the embodiments in this paragraph, the heteroaryl is 3H-indolyl. In various embodiments of each of the embodiments in this paragraph, the heteroaryl is benzo[d][1,3]dioxolyl.

According to one embodiment, the compound of formula (3) is:

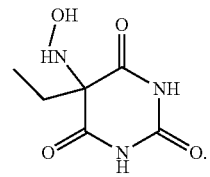

4

According to one embodiment, the compound of formula (3) is:

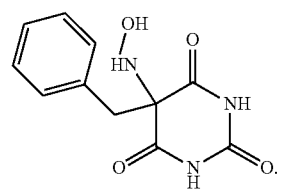

5

According to one embodiment, the compound of formula (3) is:

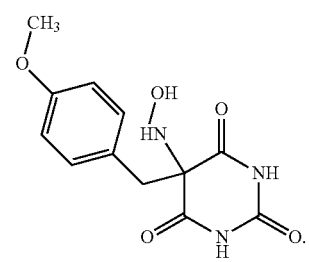

6

According to one embodiment, the compound of formula (3) is:

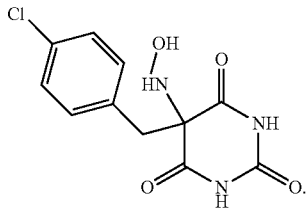

7

In particular embodiments, compounds 4, 5, 6 or 7 are utilized as a pharmaceutically acceptable salt thereof.

In another particular embodiment, the present disclosure provides a nitroxyl donating compound of the formula (4):

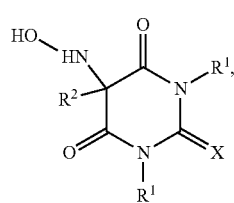

(4)

or a pharmaceutically acceptable salt thereof, wherein:
each $R^1$ is independently H or $(C_1)$alkyl;
$R^2$ is $(C_6$-$C_{10})$aryl, $(C_3$-$C_6)$cycloalkyl, $(C_5$-$C_7)$heterocycloalkyl and (5- or 6-membered)heteroaryl, wherein said aryl, cycloalkyl, heterocycloalkyl and heteroaryl are unsubstituted or substituted with 1, 2, 3, 4 or 5 substituents selected from $R^4$;
X is O, $NR^7$ or S;
each $R^4$ is independently selected from the group consisting of halo, —OH, —$NH_2$, —C≡N, —$NO_2$, —SH, =O, =S, =N—$(C_1$-$C_4)$alkyl, $(C_1$-$C_6)$alkyl, $(C_2$-$C_6)$alkenyl, $(C_2$-$C_6)$alkynyl, $(C_1$-$C_6)$alkoxy, $(C_2$-$C_6)$alkenyloxy, $(C_2$-$C_6)$alkynyloxy, $(C_6$-$C_{14})$aryl, $(C_3$-$C_6)$cycloalkyl, (5- or 6-membered)heteroaryl, $(C_5$-$C_7)$heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R'', —NHR', —NR'R'', —SR', —S(O)R', —S(O)OR', and —OR', wherein R' and R'' are independently selected from $(C_1$-$C_6)$alkyl, $(C_2$-$C_6)$alkenyl, $(C_2$-$C_6)$alkynyl, $(C_6$-$C_{14})$aryl, $(C_3$-$C_6)$cycloalkyl, (5- or 6-membered)heteroaryl and $(C_5$-$C_7)$heterocycloalkyl; and
$R^7$ is H or $(C_1$-$C_6)$alkyl.

In one embodiment, at least one of $R^1$ is H. In another, each $R^1$ is H.

In another embodiment, at least one of $R^1$ is $(C_1)$alkyl. In another embodiment, each $R^1$ is $(C_1)$alkyl.

In some aspects of this embodiment, X is S. In other aspects, X is O. In other aspects, X is NH. In other aspects, X is N$(C_1$-$C_6)$alkyl. In other aspects, X is $NCH_3$.

In one embodiment, at least one $R^1$ is H and X is S. In another embodiment, at least one $R^1$ is H and X is O. In another embodiment, at least one $R^1$ is H and X is NH. In another embodiment, at least one $R^1$ is H and X is N$(C_1$-$C_6)$alkyl. In another embodiment, at least one $R^1$ is H and X is $NCH_3$.

In another embodiment, each $R^1$ is H and X is S. In another embodiment, each $R^1$ is H and X is O. In another embodiment, each $R^1$ is H and X is NH. In another embodiment, each $R^1$ is H and X is N$(C_1$-$C_6)$alkyl. In another embodiment, each $R^1$ is H and X is $NCH_3$.

In one embodiment, at least one of $R^1$ is $(C_1)$alkyl and X is S. In another embodiment, at least one of $R^1$ is $(C_1)$alkyl and X is O. In another embodiment, at least one of $R^1$ is $(C_1)$alkyl and X is NH. In another embodiment, at least one $R^1$ is H and X is N$(C_1$-$C_6)$alkyl. In another embodiment, at least one $R^1$ is H and X is $NCH_3$.

In another embodiment, each $R^1$ is $(C_1)$alkyl and X is S. In another embodiment, each $R^1$ is $(C_1)$alkyl and X is O. In another embodiment, each $R^1$ is $(C_1)$alkyl and X is NH. In another embodiment, each $R^1$ is H and X is N$(C_1$-$C_6)$alkyl. In another embodiment, each $R^1$ is H and X is $NCH_3$.

In another embodiment, a nitroxyl donating compound of the disclosure is a compound of the formula (4a):

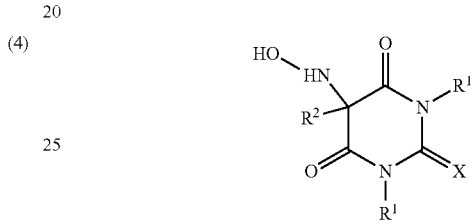

or a pharmaceutically acceptable salt thereof, wherein:
each $R^1$ is independently H or $(C_1)$alkyl;
X is O, $NR^7$ or S;
$R^2$ is $(C_6$-$C_{10})$aryl, wherein said aryl is unsubstituted or substituted with 1, 2, 3, 4 or 5 substituents selected from $R^4$;
each $R^4$ is independently selected from the group consisting of halo, —OH, —$NH_2$, —C≡N, —$NO_2$, —SH, =O, =S, =N—$(C_1$-$C_4)$alkyl, $(C_1$-$C_6)$alkyl, $(C_2$-$C_6)$alkenyl, $(C_2$-$C_6)$alkynyl, $(C_1$-$C_6)$alkoxy, $(C_2$-$C_6)$alkenyloxy, $(C_2$-$C_6)$alkynyloxy, $(C_6$-$C_{14})$aryl, $(C_3$-$C_6)$cycloalkyl, (5- or 6-membered)heteroaryl, $(C_5$-$C_7)$heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R'', —NHR', —NR'R'', —SR', —S(O)R', —S(O)OR', and —OR', wherein R' and R'' are independently selected from $(C_1$-$C_6)$alkyl, $(C_2$-$C_6)$alkenyl, $(C_2$-$C_6)$alkynyl, $(C_6$-$C_{14})$aryl, $(C_3$-$C_6)$cycloalkyl, (5- or 6-membered)heteroaryl and $(C_5$-$C_7)$heterocycloalkyl; and
$R^7$ is H or $(C_1$-$C_6)$alkyl.

In some aspects of this embodiment, at least one of $R^1$ is H. In other aspects, each $R^1$ is H.

In some aspects of this embodiment, at least one of $R^1$ is $(C_1)$alkyl. In other aspects, each $R^1$ is $(C_1)$alkyl.

In some aspects of this embodiment, X is O. In other aspects, X is NH. In other aspects, X is S. In other aspects, X is N$(C_1$-$C_6)$alkyl. In other aspects, X is $NCH_3$.

In some aspects of this embodiment, $R^2$ is $(C_6$-$C_{10})$aryl, wherein said aryl is unsubstituted or substituted with 1, 2 or 3 substituent(s) independently selected from $R^4$. In some embodiments, $R^2$ is $(C_6$-$C_{10})$aryl, wherein said aryl is unsubstituted or substituted with 1, 2 or 3 substituent(s) independently selected from halo, —OH, —$NH_2$, —C≡N, —$NO_2$, —SH, $(C_1$-$C_6)$alkyl or $(C_1$-$C_6)$alkoxy. In another embodiment, $R^2$ is $(C_6$-$C_{10})$aryl, wherein said aryl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, R$^2$ is (C$_6$-C$_{10}$)aryl, wherein said aryl is unsubstituted or substituted with 1 substituent selected from halo, —OH, —NH$_2$, —C≡N, —NO$_2$, —SH, (C$_1$-C$_6$)alkyl or (C$_1$-C$_6$) alkoxy. In another embodiment, R$^2$ is unsubstituted (C$_6$-C$_{10}$) aryl. In another embodiment, R$^2$ is (C$_6$-C$_{10}$)aryl substituted with 1 substituent selected from halo, —OH, —NH$_2$, —C≡N, —NO$_2$, —SH, (C$_1$-C$_6$)alkyl or (C$_1$-C$_6$)alkoxy.

In some aspects, R$^2$ is phenyl, wherein said phenyl is unsubstituted or substituted with 1, 2 or 3 substituent(s) independently selected from halo, —OH, —NH$_2$, —C≡N, —NO$_2$, —SH, (C$_1$-C$_6$)alkyl or (C$_1$-C$_6$)alkoxy. In another embodiment, R$^2$ is phenyl, wherein said phenyl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, R$^2$ is phenyl, wherein said phenyl is unsubstituted or substituted with 1 substituent selected from halo, —OH, —NH$_2$, —C≡N, —NO$_2$, —SH, (C$_1$-C$_6$)alkyl or (C$_1$-C$_6$)alkoxy. In another embodiment, R$^2$ is unsubstituted phenyl. In another embodiment, R$^2$ is phenyl substituted with 1 substituent selected from halo, —OH, —NH$_2$, —C≡N, —NO$_2$, —SH, (C$_1$-C$_6$)alkyl or (C$_1$-C$_6$)alkoxy.

In some embodiments, at least one of R$^1$ is H and R$^2$ is phenyl, wherein said phenyl is unsubstituted or substituted with 1, 2 or 3 substituent(s) independently selected from halo, —OH, —NH$_2$, —C≡N, —NO$_2$, —SH, (C$_1$-C$_6$)alkyl or (C$_1$-C$_6$)alkoxy. In another embodiment, at least one of R$^1$ is H and R$^2$ is phenyl, wherein said phenyl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, at least one of R$^1$ is H and R$^2$ is phenyl, wherein said phenyl is unsubstituted or substituted with 1 substituent selected from halo, —OH, —NH$_2$, —C≡N, —NO$_2$, —SH, (C$_1$-C$_6$) alkyl or (C$_1$-C$_6$)alkoxy. In another embodiment, at least one of R$^1$ is H and R$^2$ is unsubstituted phenyl. In another embodiment, at least one of R$^1$ is H and R$^2$ is phenyl substituted with 1 substituent selected from halo, —OH, —NH$_2$, —C≡N, —NO$_2$, —SH, (C$_1$-C$_6$)alkyl or (C$_1$-C$_6$) alkoxy.

In some embodiments, each R$^1$ is H and R$^2$ is phenyl, wherein said phenyl is unsubstituted or substituted with 1, 2 or 3 substituent(s) independently selected from halo, —OH, —NH$_2$, —C≡N, —NO$_2$, —SH, (C$_1$-C$_6$)alkyl or (C$_1$-C$_6$) alkoxy. In another embodiment, each R$^1$ is H and R$^2$ is phenyl, wherein said phenyl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, each R$^1$ is H and R$^2$ is phenyl, wherein said phenyl is unsubstituted or substituted with 1 substituent selected from halo, —OH, —NH$_2$, —C≡N, —NO$_2$, —SH, (C$_1$-C$_6$)alkyl or (C$_1$-C$_6$)alkoxy. In another embodiment, each R$^1$ is H and R$^2$ is unsubstituted phenyl. In another embodiment, each R$^1$ is H and R$^2$ is phenyl substituted with 1 substituent selected from halo, —OH, —NH$_2$, —C≡N, —NO$_2$, —SH, (C$_1$-C$_6$)alkyl or (C$_1$-C$_6$)alkoxy.

In some embodiments, at least one of R$^1$ is (C$_1$)alkyl and R$^2$ is phenyl, wherein said phenyl is unsubstituted or substituted with 1, 2 or 3 substituent(s) independently selected from halo, —OH, —NH$_2$, —C≡N, —NO$_2$, —SH, (C$_1$-C$_6$) alkyl or (C$_1$-C$_6$)alkoxy. In another embodiment, at least one of R$^1$ is (C$_1$)alkyl and R$^2$ is phenyl, wherein said phenyl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, at least one of R$^1$ is (C$_1$)alkyl and R$^2$ is phenyl, wherein said phenyl is unsubstituted or substituted with 1 substituent selected from halo, —OH, —NH$_2$, —C≡N, —NO$_2$, —SH, (C$_1$-C$_6$)alkyl or (C$_1$-C$_6$)alkoxy. In another embodiment, at least one of R$^1$ is (C$_1$)alkyl and R$^2$ is unsubstituted phenyl. In another embodiment, at least one of R$^1$ is (C$_1$)alkyl and R$^2$ is phenyl substituted with 1 substituent selected from halo, —OH, —NH$_2$, —C≡N, —NO$_2$, —SH, (C$_1$-C$_6$)alkyl or (C$_1$-C$_6$)alkoxy.

In some embodiments, each R$^1$ is (C$_1$)alkyl and R$^2$ is phenyl, wherein said phenyl is unsubstituted or substituted with 1, 2 or 3 substituent(s) independently selected from halo, —OH, —NH$_2$, —C≡N, —NO$_2$, —SH, (C$_1$-C$_6$)alkyl or (C$_1$-C$_6$)alkoxy. In another embodiment, each R$^1$ is (C$_1$) alkyl and R$^2$ is phenyl, wherein said phenyl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, each R$^1$ is (C$_1$)alkyl and R$^2$ is phenyl, wherein said phenyl is unsubstituted or substituted with 1 substituent selected from halo, —OH, —NH$_2$, —C≡N, —NO$_2$, —SH, (C$_1$-C$_6$) alkyl or (C$_1$-C$_6$)alkoxy. In another embodiment, each R$^1$ is (C$_1$)alkyl and R$^2$ is unsubstituted phenyl. In another embodiment, each R$^1$ is (C$_1$)alkyl and R$^2$ is phenyl substituted with 1 substituent selected from halo, —OH, —NH$_2$, —C≡N, —NO$_2$, —SH, (C$_1$-C$_6$)alkyl or (C$_1$-C$_6$)alkoxy.

In some embodiments, at least one of R$^1$ is H and X is S. In another embodiment, at least one of R$^1$ is H and X is NH. In another embodiment, at least one of R$^1$ is H and X is O. In another embodiment, at least one R$^1$ is H and X is N(C$_1$-C$_6$)alkyl. In another embodiment, at least one R$^1$ is H and X is NCH$_3$.

In some embodiments, each R$^1$ is H and X is S. In another embodiment, each R$^1$ is H and X is NH. In another embodiment, each R$^1$ is H and X is O. In another embodiment, each R$^1$ is H and X is N(C$_1$-C$_6$)alkyl. In another embodiment, each R$^1$ is H and X is NCH$_3$.

In some embodiments, at least one of R$^1$ is (C$_1$)alkyl and X is S. In another embodiment, at least one of R$^1$ is (C$_1$)alkyl and X is NH. In another embodiment, at least one of R$^1$ is (C$_1$)alkyl and X is O. In another embodiment, at least one R$^1$ is H and X is N(C$_1$-C$_6$)alkyl. In another embodiment, at least one R$^1$ is H and X is NCH$_3$.

In some embodiments, each R$^1$ is (C$_1$)alkyl and X is S. In another embodiment, each R$^1$ is (C$_1$)alkyl and X is NH. In another embodiment, each R$^1$ is (C$_1$)alkyl and X is O. In another embodiment, each R$^1$ is H and X is N(C$_1$-C$_6$)alkyl. In another embodiment, each R$^1$ is H and X is NCH$_3$.

In another embodiment, a nitroxyl donating compound of the disclosure is a compound of the formula (4b):

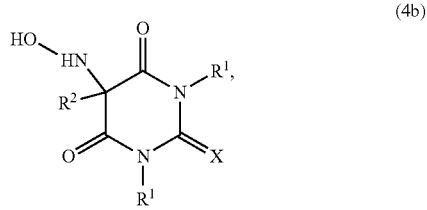

(4b)

or a pharmaceutically acceptable salt thereof, wherein:
each R$^1$ is independently H or (C$_1$)alkyl;
X is O, NR$^7$ or S;
R$^2$ is (C$_3$-C$_6$)cycloalkyl, wherein said cycloalkyl is unsubstituted or substituted with 1, 2, 3, 4 or 5 substituents selected from R$^4$;
each R$^4$ is independently selected from the group consisting of halo, —OH, —NH$_2$, —C≡N, —NO$_2$, —SH, =O, =S, =N—(C$_1$-C$_4$)alkyl, (C$_1$-C$_6$)alkyl, (C$_2$-C$_6$) alkenyl, (C$_2$-C$_6$)alkynyl, (C$_1$-C$_6$)alkoxy, (C$_2$-C$_6$)alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R'', —NHR', —NR'R'', —SR', —S(O)R', —S(O)OR', and —OR', wherein R' and R'' are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl; and R$^7$ is H or $(C_1-C_6)$alkyl.

In some aspects of this embodiment, at least one of R$^1$ is H. In other aspects, each R$^1$ is H. In some aspects of this embodiment, at least one of R$^1$ is $(C_1)$alkyl. In other aspects, each R$^1$ is $(C_1)$alkyl.

In some aspects of this embodiment, X is O. In other aspects, X is NH. In other aspects, X is S. In other aspects, X is N$(C_1-C_6)$alkyl. In other aspects, X is NCH$_3$.

In some aspects of this embodiment, R$^2$ is $(C_3-C_6)$cycloalkyl, wherein said cycloalkyl is unsubstituted or substituted with 1, 2 or 3 substituent(s) independently selected from R$^4$. In some embodiments, R$^2$ is $(C_3-C_6)$cycloalkyl, wherein said cycloalkyl is unsubstituted or substituted with 1, 2 or 3 substituent(s) independently selected from halo, —OH, —NH$_2$, —C≡N, —NO$_2$, —SH, $(C_1-C_6)$alkyl or $(C_1-C_6)$alkoxy. In another embodiment, R$^2$ is $(C_3-C_6)$cycloalkyl, wherein said cycloalkyl is unsubstituted or substituted with 1 or 2 substituent(s) independently selected from halo, —OH, —NH$_2$, —C≡N, —NO$_2$, —SH, $(C_1-C_6)$alkyl or $(C_1-C_6)$alkoxy. In another embodiment, R$^2$ is $(C_3-C_6)$cycloalkyl, wherein said cycloalkyl is unsubstituted or substituted with 1 substituent selected from halo, —OH, —NH$_2$, —C≡N, —NO$_2$, —SH, $(C_1-C_6)$alkyl or $(C_1-C_6)$alkoxy. In another embodiment, R$^2$ is unsubstituted $(C_3-C_6)$cycloalkyl. In another embodiment, R$^2$ is $(C_3-C_6)$cycloalkyl substituted with 1 substituent selected from halo, —OH, —NH$_2$, —C≡N, —NO$_2$, —SH, $(C_1-C_6)$alkyl or $(C_1-C_6)$alkoxy.

In some aspects, R$^2$ is cyclohexyl, wherein said cyclohexyl is unsubstituted or substituted with 1, 2, 3, 4 or 5 substituent(s) independently selected from R$^4$. In some aspects, R$^2$ is cyclohexyl, wherein said cyclohexyl is unsubstituted or substituted with 1, 2 or 3 substituent(s) independently selected from R$^4$. In some embodiments, R$^2$ is cyclohexyl, wherein said cyclohexyl is unsubstituted or substituted with 1, 2 or 3 substituent(s) independently selected from halo, —OH, —NH$_2$, —C≡N, —NO$_2$, —SH, $(C_1-C_6)$alkyl or $(C_1-C_6)$alkoxy. In another embodiment, R$^2$ is cyclohexyl, wherein said cyclohexyl is unsubstituted or substituted with 1 or 2 substituent(s) independently selected from halo, —OH, —NH$_2$, —C≡N, —NO$_2$, —SH, $(C_1-C_6)$alkyl or $(C_1-C_6)$alkoxy. In another embodiment, R$^2$ is cyclohexyl, wherein said cyclohexyl is unsubstituted or substituted with 1 substituent selected from halo, —OH, —NH$_2$, —C≡N, —NO$_2$, —SH, $(C_1-C_6)$alkyl or $(C_1-C_6)$alkoxy. In another embodiment, R$^2$ is unsubstituted cyclohexyl. In another embodiment, R$^2$ is cyclohexyl substituted with 1 substituent selected from halo, —OH, —NH$_2$, —C≡N, —NO$_2$, —SH, $(C_1-C_6)$alkyl or $(C_1-C_6)$alkoxy.

In some embodiments, at least one of R$^1$ is H and R$^2$ is cyclohexyl, wherein said cyclohexyl is unsubstituted or substituted with 1, 2 or 3 substituent(s) independently selected from R$^4$. In some embodiments, at least one of R$^1$ is H and R$^2$ is cyclohexyl, wherein said cyclohexyl is unsubstituted or substituted with 1, 2 or 3 substituent(s) independently selected from halo, —OH, —NH$_2$, —C≡N, —NO$_2$, —SH, $(C_1-C_6)$alkyl or $(C_1-C_6)$alkoxy. In another embodiment, at least one of R$^1$ is H and R$^2$ is cyclohexyl, wherein said cyclohexyl is unsubstituted or substituted with 1 or 2 substituent(s) independently selected from halo, —OH, —NH$_2$, —C≡N, —NO$_2$, —SH, $(C_1-C_6)$alkyl or $(C_1-C_6)$alkoxy. In another embodiment, at least one of R$^1$ is H and R$^2$ is cyclohexyl, wherein said cyclohexyl is unsubstituted or substituted with 1 substituent selected from halo, —OH, —NH$_2$, —C≡N, —NO$_2$, —SH, $(C_1-C_6)$alkyl or $(C_1-C_6)$alkoxy. In another embodiment, at least one of R$^1$ is H and R$^2$ is unsubstituted cyclohexyl. In another embodiment, at least one of R$^1$ is H and R$^2$ is cyclohexyl substituted with 1 substituent selected from halo, —OH, —NH$_2$, —C≡N, —NO$_2$, —SH, $(C_1-C_6)$alkyl or $(C_1-C_6)$alkoxy.

In some embodiments, each R$^1$ is H and R$^2$ is cyclohexyl, wherein said cyclohexyl is unsubstituted or substituted with 1, 2 or 3 substituent(s) independently selected from R$^4$. In some embodiments, each R$^1$ is H and R$^2$ is cyclohexyl, wherein said cyclohexyl is unsubstituted or substituted with 1, 2 or 3 substituent(s) independently selected from halo, —OH, —NH$_2$, —C≡N, —NO$_2$, —SH, $(C_1-C_6)$alkyl or $(C_1-C_6)$alkoxy. In another embodiment, each R$^1$ is H and R$^2$ is cyclohexyl, wherein said cyclohexyl is unsubstituted or substituted with 1 or 2 substituent(s) independently selected from halo, —OH, —NH$_2$, —C≡N, —NO$_2$, —SH, $(C_1-C_6)$alkyl or $(C_1-C_6)$alkoxy. In another embodiment, each R$^1$ is H and R$^2$ is cyclohexyl, wherein said cyclohexyl is unsubstituted or substituted with 1 substituent selected from halo, —OH, —NH$_2$, —C≡N, —NO$_2$, —SH, $(C_1-C_6)$alkyl or $(C_1-C_6)$alkoxy. In another embodiment, each R$^1$ is H and R$^2$ is unsubstituted cyclohexyl. In another embodiment, each R$^1$ is H and R$^2$ is cyclohexyl substituted with 1 substituent selected from halo, —OH, —NH$_2$, —C≡N, —NO$_2$, —SH, $(C_1-C_6)$alkyl or $(C_1-C_6)$alkoxy.

In some embodiments, at least one of R$^1$ is $(C_1)$alkyl and R$^2$ is cyclohexyl, wherein said cyclohexyl is unsubstituted or substituted with 1, 2 or 3 substituent(s) independently selected from R$^4$. In some embodiments, at least one of R$^1$ is $(C_1)$alkyl and R$^2$ is cyclohexyl, wherein said cyclohexyl is unsubstituted or substituted with 1, 2 or 3 substituent(s) independently selected from halo, —OH, —NH$_2$, —C≡N, —NO$_2$, —SH, $(C_1-C_6)$alkyl or $(C_1-C_6)$alkoxy. In another embodiment, at least one of R$^1$ is $(C_1)$alkyl and R$^2$ is cyclohexyl, wherein said cyclohexyl is unsubstituted or substituted with 1 or 2 substituent(s) independently selected from halo, —OH, —NH$_2$, —C≡N, —NO$_2$, —SH, $(C_1-C_6)$alkyl or $(C_1-C_6)$alkoxy. In another embodiment, at least one of R$^1$ is $(C_1)$alkyl and R$^2$ is cyclohexyl, wherein said cyclohexyl is unsubstituted or substituted with 1 substituent selected from halo, —OH, —NH$_2$, —C≡N, —NO$_2$, —SH, $(C_1-C_6)$alkyl or $(C_1-C_6)$alkoxy. In another embodiment, at least one of R$^1$ is $(C_1)$alkyl and R$^2$ is unsubstituted cyclohexyl. In another embodiment, at least one of R$^1$ is $(C_1)$alkyl and R$^2$ is cyclohexyl substituted with 1 substituent selected from halo, —OH, —NH$_2$, —C≡N, —NO$_2$, —SH, $(C_1-C_6)$alkyl or $(C_1-C_6)$alkoxy.

In some embodiments, each R$^1$ is $(C_1)$alkyl and R$^2$ is cyclohexyl, wherein said cyclohexyl is unsubstituted or substituted with 1, 2 or 3 substituent(s) independently selected from R$^4$. In some embodiments, each R$^1$ is $(C_1)$alkyl and R$^2$ is cyclohexyl, wherein said cyclohexyl is unsubstituted or substituted with 1, 2 or 3 substituent(s) independently selected from halo, —OH, —NH$_2$, —C≡N, —NO$_2$, —SH, $(C_1-C_6)$alkyl or $(C_1-C_6)$alkoxy. In another embodiment, each R$^1$ is $(C_1)$alkyl and R$^2$ is cyclohexyl, wherein said cyclohexyl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, each R$^1$ is (C$_1$)alkyl and R$^2$ is cyclohexyl, wherein said cyclohexyl is unsubstituted or substituted with 1 substituent selected from halo, —OH, —NH$_2$, —C≡N, —NO$_2$, —SH, (C$_1$-C$_6$)alkyl or (C$_1$-C$_6$)alkoxy. In another embodiment, each R$^1$ is (C$_1$)alkyl and R$^2$ is unsubstituted cyclohexyl. In another embodiment, each R$^1$ is (C$_1$)alkyl and R$^2$ is cyclohexyl substituted with 1 substituent selected from halo, —OH, —NH$_2$, —C≡N, —NO$_2$, —SH, (C$_1$-C$_6$)alkyl or (C$_1$-C$_6$)alkoxy.

In some embodiments, at least one of R$^1$ is H and X is S. In another embodiment, at least one of R$^1$ is H and X is NH. In another embodiment, at least one of R$^1$ is H and X is O. In another embodiment, at least one R$^1$ is H and X is N(C$_1$-C$_6$)alkyl. In another embodiment, at least one R$^1$ is H and X is NCH$_3$.

In some embodiments, each R$^1$ is H and X is S. In another embodiment, each R$^1$ is H and X is NH. In another embodiment, each R$^1$ is H and X is O. In another embodiment, each R$^1$ is H and X is N(C$_1$-C$_6$)alkyl. In another embodiment, each R$^1$ is H and X is NCH$_3$.

In some embodiments, at least one of R$^1$ is (C$_1$)alkyl and X is S. In another embodiment, at least one of R$^1$ is (C$_1$)alkyl and X is NH. In another embodiment, at least one of R$^1$ is (C$_1$)alkyl and X is O. In another embodiment, at least one R$^1$ is H and X is N(C$_1$-C$_6$)alkyl. In another embodiment, at least one R$^1$ is H and X is NCH$_3$.

In some embodiments, each R$^1$ is (C$_1$)alkyl and X is S. In another embodiment, each R$^1$ is (C$_1$)alkyl and X is NH. In another embodiment, each R$^1$ is (C$_1$)alkyl and X is O. In another embodiment, each R$^1$ is H and X is N(C$_1$-C$_6$)alkyl. In another embodiment, each R$^1$ is H and X is NCH$_3$.

In another embodiment, a nitroxyl donating compound of the disclosure is a compound of the formula (4c):

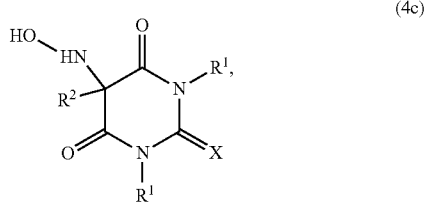

(4c)

or a pharmaceutically acceptable salt thereof, wherein:
each R$^1$ is independently H or (C$_1$)alkyl;
X is O, NR$^7$ or S;
R$^2$ is (C$_5$-C$_7$)heterocycloalkyl, wherein said heterocycloalkyl is unsubstituted or substituted with 1, 2, 3, 4 or 5 substituents selected from R$^4$;
each R$^4$ is independently selected from the group consisting of halo, —OH, —NH$_2$, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_5$-C$_7$)heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R'', —NHR', —NR'R'', —SR', —S(O)R', —S(O)OR', and —OR', wherein R' and R'' are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_5$-C$_7$)heterocycloalkyl; and
R$^7$ is H or (C$_1$-C$_6$)alkyl.

In some aspects of this embodiment, at least one of R$^1$ is H. In other aspects, each R$^1$ is H.

In some aspects of this embodiment, at least one of R$^1$ is (C$_1$)alkyl. In other aspects, each R$^1$ is (C$_1$)alkyl.

In some aspects of this embodiment, X is O. In other aspects, X is NH. In other aspects, X is S. In other aspects, X is N(C$_1$-C$_6$)alkyl. In other aspects, X is NCH$_3$.

In some aspects of this embodiment, R$^2$ is (C$_5$-C$_7$)heterocycloalkyl, wherein said heterocycloalkyl is unsubstituted or substituted with 1, 2 or 3 substituent(s) independently selected from R$^4$. In some embodiments, R$^2$ is (C$_5$-C$_7$)heterocycloalkyl, wherein said heterocycloalkyl is unsubstituted or substituted with 1, 2 or 3 substituent(s) independently selected from halo, —OH, —NH$_2$, —C≡N, —NO$_2$, —SH, (C$_1$-C$_6$)alkyl or (C$_1$-C$_6$)alkoxy. In another embodiment, R$^2$ is (C$_5$-C$_7$)heterocycloalkyl, wherein said heterocycloalkyl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, R$^2$ is (C$_5$-C$_7$)heterocycloalkyl, wherein said heterocycloalkyl is unsubstituted or substituted with 1 substituent selected from halo, —OH, —NH$_2$, —C≡N, —NO$_2$, —SH, (C$_1$-C$_6$)alkyl or (C$_1$-C$_6$)alkoxy. In another embodiment, R$^2$ is unsubstituted (C$_5$-C$_7$)heterocycloalkyl. In another embodiment, R$^2$ is (C$_5$-C$_7$)heterocycloalkyl substituted with 1 substituent selected from halo, —OH, —NH$_2$, —C≡N, —NO$_2$, —SH, (C$_1$-C$_6$)alkyl or (C$_1$-C$_6$)alkoxy.

In some aspects, R$^2$ is (C$_6$)heterocycloalkyl, wherein heterocycloalkyl is unsubstituted or substituted with 1, 2 or 3 substituent(s) independently selected from R$^4$. In some embodiments, R$^2$ is (C$_6$)heterocycloalkyl, wherein said heterocycloalkyl is unsubstituted or substituted with 1, 2 or 3 substituent(s) independently selected from halo, —OH, —NH$_2$, —C≡N, —NO$_2$, —SH, (C$_1$-C$_6$)alkyl or (C$_1$-C$_6$)alkoxy. In another embodiment, R$^2$ is (C$_6$)heterocycloalkyl, wherein said heterocycloalkyl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, R$^2$ is (C$_6$)heterocycloalkyl, wherein said heterocycloalkyl is unsubstituted or substituted with 1 substituent selected from halo, —OH, —NH$_2$, —C≡N, —NO$_2$, —SH, (C$_1$-C$_6$)alkyl or (C$_1$-C$_6$)alkoxy. In another embodiment, R$^2$ is unsubstituted (C$_6$)heterocycloalkyl. In another embodiment, R$^2$ is (C$_6$)heterocycloalkyl substituted with 1 substituent selected from halo, —OH, —NH$_2$, —C≡N, —NO$_2$, —SH, (C$_1$-C$_6$)alkyl or (C$_1$-C$_6$)alkoxy.

In some embodiments, at least one of R$^1$ is H and R$^2$ is (C$_6$)heterocycloalkyl, wherein (C$_6$)heterocycloalkyl is unsubstituted or substituted with 1, 2 or 3 substituent(s) independently selected from R$^4$. In some embodiments, at least one of R$^1$ is H and R$^2$ is (C$_6$)heterocycloalkyl, wherein said (C$_6$)heterocycloalkyl is unsubstituted or substituted with 1, 2 or 3 substituent(s) independently selected from halo, —OH, —NH$_2$, —C≡N, —NO$_2$, —SH, (C$_1$-C$_6$)alkyl or (C$_1$-C$_6$)alkoxy. In another embodiment, at least one of R$^1$ is H and R$^2$ is (C$_6$)heterocycloalkyl, wherein said (C$_6$)heterocycloalkyl is unsubstituted or substituted with 1 or 2 substituent(s) independently selected from halo, —OH, —NH$_2$, —C≡N, —NO$_2$, —SH, (C$_1$-C$_6$)alkyl or (C$_1$-C$_6$)alkoxy. In another embodiment, at least one of R$^1$ is H and R$^2$ is (C$_6$)heterocycloalkyl, wherein said (C$_6$)heterocycloalkyl is unsubstituted or substituted with 1 substituent selected from halo, —OH, —NH$_2$, —C≡N, —NO$_2$, —SH, (C$_1$-C$_6$)alkyl or (C$_1$-C$_6$)alkoxy. In another embodiment, at least one of R$^1$ is H and R$^2$ is unsubstituted (C$_6$)heterocycloalkyl. In another embodiment, at least one of $R^1$ is H and $R^2$ is $(C_6)$heterocycloalkyl substituted with 1 substituent selected from halo, —OH, —NH$_2$, —NO$_2$, —SH, $(C_1$-$C_6)$ alkyl or $(C_1$-$C_6)$alkoxy.

In some embodiments, each $R^1$ is H and $R^2$ is $(C_6)$ heterocycloalkyl, wherein $(C_6)$heterocycloalkyl is unsubstituted or substituted with 1, 2 or 3 substituent(s) independently selected from $R^4$. In some embodiments, each $R^1$ is H and $R^2$ is $(C_6)$heterocycloalkyl, wherein said $(C_6)$heterocycloalkyl is unsubstituted or substituted with 1, 2 or 3 substituent(s) independently selected from halo, —OH, —NH$_2$, —C≡N, —NO$_2$, —SH, $(C_1$-$C_6)$alkyl or $(C_1$-$C_6)$ alkoxy. In another embodiment, each $R^1$ is H and $R^2$ is $(C_6)$heterocycloalkyl, wherein said $(C_6)$heterocycloalkyl is unsubstituted or substituted with 1 or 2 substituent(s) independently selected from halo, —OH, —NH$_2$, —C≡N, —NO$_2$, —SH, $(C_1$-$C_6)$alkyl or $(C_1$-$C_6)$alkoxy. In another embodiment, each $R^1$ is H and $R^2$ is $(C_6)$heterocycloalkyl, wherein said $(C_6)$heterocycloalkyl is unsubstituted or substituted with 1 substituent selected from halo, —OH, —NH$_2$, —C≡N, —NO$_2$, —SH, $(C_1$-$C_6)$alkyl or $(C_1$-$C_6)$ alkoxy. In another embodiment, each $R^1$ is H and $R^2$ is unsubstituted $(C_6)$heterocycloalkyl. In another embodiment, each $R^1$ is H and $R^2$ is $(C_6)$heterocycloalkyl substituted with 1 substituent selected from halo, —OH, —NH$_2$, —C≡N, —NO$_2$, —SH, $(C_1$-$C_6)$alkyl or $(C_1$-$C_6)$alkoxy.

In some embodiments, at least one of $R^1$ is $(C_1)$alkyl and $R^2$ is $(C_6)$heterocycloalkyl, wherein said $(C_6)$heterocycloalkyl is unsubstituted or substituted with 1, 2 or 3 substituent(s) independently selected from $R^4$. In some embodiments, at least one of $R^1$ is $(C_1)$alkyl and $R^2$ is $(C_6)$heterocycloalkyl, wherein said $(C_6)$heterocycloalkyl is unsubstituted or substituted with 1, 2 or 3 substituent(s) independently selected from halo, —OH, —NH$_2$, —C≡N, —NO$_2$, —SH, $(C_1$-$C_6)$alkyl or $(C_1$-$C_6)$alkoxy. In another embodiment, at least one of $R^1$ is $(C_1)$alkyl and $R^2$ is $(C_6)$heterocycloalkyl, wherein said $(C_6)$heterocycloalkyl is unsubstituted or substituted with 1 or 2 substituent(s) independently selected from halo, —OH, —NH$_2$, —C≡N, —NO$_2$, —SH, $(C_1$-$C_6)$alkyl or $(C_1$-$C_6)$alkoxy. In another embodiment, at least one of $R^1$ is $(C_1)$alkyl and $R^2$ is $(C_6)$heterocycloalkyl, wherein said $(C_6)$heterocycloalkyl is unsubstituted or substituted with 1 substituent selected from halo, —OH, —NH$_2$, —C≡N, —NO$_2$, —SH, $(C_1$-$C_6)$alkyl or $(C_1$-$C_6)$alkoxy. In another embodiment, at least one of $R^1$ is $(C_1)$alkyl and $R^2$ is unsubstituted $(C_6)$heterocycloalkyl. In another embodiment, at least one of $R^1$ is $(C_1)$alkyl and $R^2$ is $(C_6)$heterocycloalkyl substituted with 1 substituent selected from halo, —OH, —NH$_2$, —C≡N, —NO$_2$, —SH, $(C_1$-$C_6)$alkyl or $(C_1$-$C_6)$alkoxy.

In some embodiments, each $R^1$ is $(C_1)$alkyl and $R^2$ is $(C_6)$heterocycloalkyl, wherein $(C_6)$heterocycloalkyl is unsubstituted or substituted with 1, 2 or 3 substituent(s) independently selected from $R^4$. In some embodiments, each $R^1$ is $(C_1)$alkyl and $R^2$ is $(C_6)$heterocycloalkyl, wherein said $(C_6)$heterocycloalkyl is unsubstituted or substituted with 1, 2 or 3 substituent(s) independently selected from halo, —OH, —NH$_2$, —C≡N, —NO$_2$, —SH, $(C_1$-$C_6)$alkyl or $(C_1$-$C_6)$alkoxy. In another embodiment, each $R^1$ is $(C_1)$alkyl and $R^2$ is $(C_6)$heterocycloalkyl, wherein said $(C_6)$heterocycloalkyl is unsubstituted or substituted with 1 or 2 substituent(s) independently selected from halo, —OH, —NH$_2$, —C≡N, —NO$_2$, —SH, $(C_1$-$C_6)$alkyl or $(C_1$-$C_6)$alkoxy. In another embodiment, each $R^1$ is $(C_1)$alkyl and $R^2$ is $(C_6)$ heterocycloalkyl, wherein said $(C_6)$heterocycloalkyl is unsubstituted or substituted with 1 substituent selected from halo, —OH, —NH$_2$, —C≡N, —NO$_2$, —SH, $(C_1$-$C_6)$alkyl or $(C_1$-$C_6)$alkoxy. In another embodiment, each $R^1$ is $(C_1)$ alkyl and $R^2$ is unsubstituted $(C_6)$heterocycloalkyl. In another embodiment, each $R^1$ is $(C_1)$alkyl and $R^2$ is $(C_6)$ heterocycloalkyl substituted with 1 substituent selected from halo, —OH, —NH$_2$, —C≡N, —NO$_2$, —SH, $(C_1$-$C_6)$alkyl or $(C_1$-$C_6)$alkoxy.

In some embodiments, at least one of $R^1$ is H and X is S. In another embodiment, at least one of $R^1$ is H and X is NH. In another embodiment, at least one of $R^1$ is H and X is O. In another embodiment, at least one $R^1$ is H and X is $N(C_1$-$C_6)$alkyl. In another embodiment, at least one $R^1$ is H and X is NCH$_3$.

In some embodiments, each $R^1$ is H and X is S. In another embodiment, each $R^1$ is H and X is NH. In another embodiment, each $R^1$ is H and X is O. In another embodiment, each $R^1$ is H and X is $N(C_1$-$C_6)$alkyl. In another embodiment, each $R^1$ is H and X is NCH$_3$.

In some embodiments, at least one of $R^1$ is $(C_1)$alkyl and X is S. In another embodiment, at least one of $R^1$ is $(C_1)$alkyl and X is NH. In another embodiment, at least one of $R^1$ is $(C_1)$alkyl and X is O. In another embodiment, at least one $R^1$ is H and X is $N(C_1$-$C_6)$alkyl. In another embodiment, at least one $R^1$ is H and X is NCH$_3$.

In some embodiments, each $R^1$ is $(C_1)$alkyl and X is S. In another embodiment, each $R^1$ is $(C_1)$alkyl and X is NH. In another embodiment, each $R^1$ is $(C_1)$alkyl and X is O. In another embodiment, each $R^1$ is H and X is $N(C_1$-$C_6)$alkyl. In another embodiment, each $R^1$ is H and X is NCH$_3$.

In another embodiment, a nitroxyl donating compound of the disclosure is a compound of the formula (4d):

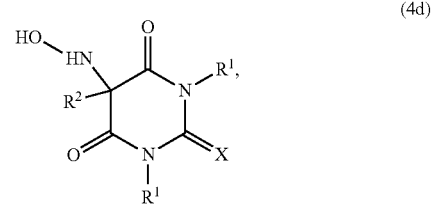

(4d)

or a pharmaceutically acceptable salt thereof, wherein:
each $R^1$ is independently H or $(C_1)$alkyl;
X is O, NR$^7$ or S;
$R^2$ is (5- or 6-membered)heteroaryl, wherein said heteroaryl is unsubstituted or substituted with 1, 2, 3, 4 or 5 substituents selected from $R^4$;
each $R^4$ is independently selected from the group consisting of halo, —OH, —NH$_2$, —C≡N, —NO$_2$, —SH, =O, =S, =N—$(C_1$-$C_4)$alkyl, $(C_1$-$C_6)$alkyl, $(C_2$-$C_6)$ alkenyl, $(C_2$-$C_6)$alkynyl, $(C_1$-$C_6)$alkoxy, $(C_2$-$C_6)$alkenyloxy, $(C_2$-$C_6)$alkynyloxy, $(C_6$-$C_{14})$aryl, $(C_3$-$C_6)$cycloalkyl, (5- or 6-membered)heteroaryl, $(C_5$-$C_7)$ heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O) NR'R", —NHR', —NR'R", —SR', —S(O)R', —S(O) OR', and —OR', wherein R' and R" are independently selected from $(C_1$-$C_6)$alkyl, $(C_2$-$C_6)$alkenyl, $(C_2$-$C_6)$ alkynyl, $(C_6$-$C_{14})$aryl, $(C_3$-$C_6)$cycloalkyl, (5- or 6-membered)heteroaryl and $(C_5$-$C_7)$heterocycloalkyl; and
$R^7$ is H or $(C_1$-$C_6)$alkyl.

In some aspects of this embodiment, at least one of $R^1$ is H. In other aspects, each $R^1$ is H.

In some aspects of this embodiment, at least one of $R^1$ is $(C_1)$alkyl. In other aspects, each $R^1$ is $(C_1)$alkyl.

In some aspects of this embodiment, X is O. In other aspects, X is NH. In other aspects, X is S. In other aspects, X is $N(C_1\text{-}C_6)$alkyl. In other aspects, X is $NCH_3$.

In some aspects of this embodiment, $R^2$ is (5- or 6-membered)heteroaryl, wherein said heteroaryl is unsubstituted or substituted with 1, 2 or 3 substituent(s) independently selected from $R^4$. In some embodiments, $R^2$ is (5- or 6-membered)heteroaryl, wherein said heteroaryl is unsubstituted or substituted with 1, 2 or 3 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, $R^2$ is (5- or 6-membered)heteroaryl, wherein said heteroaryl is unsubstituted or substituted with 1 or 2 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, $R^2$ is (5- or 6-membered)heteroaryl, wherein said heteroaryl is unsubstituted or substituted with 1 substituent selected from halo, —OH, —$NH_2$, —C≡N, —$NO_2$, —SH, $(C_1\text{-}C_6)$alkyl or $(C_1\text{-}C_6)$alkoxy. In another embodiment, $R^2$ is unsubstituted (5- or 6-membered)heteroaryl. In another embodiment, $R^2$ is (5- or 6-membered)heteroaryl substituted with 1 substituent selected from halo, —OH, —$NH_2$, —C≡N, —$NO_2$, —SH, $(C_1\text{-}C_6)$alkyl or $(C_1\text{-}C_6)$alkoxy.

In some embodiments, at least one of $R^1$ is H and $R^2$ is (5- or 6-membered)heteroaryl, wherein said heteroaryl is unsubstituted or substituted with 1, 2 or 3 substituent(s) independently selected from $R^4$. In some embodiments, at least one of $R^1$ is H and $R^2$ is (5- or 6-membered)heteroaryl, wherein said heteroaryl is unsubstituted or substituted with 1, 2 or 3 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, at least one of $R^1$ is H and $R^2$ is (5- or 6-membered)heteroaryl, wherein said heteroaryl is unsubstituted or substituted with 1 or 2 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, at least one of $R^1$ is H and $R^2$ is (5- or 6-membered)heteroaryl, wherein said heteroaryl is unsubstituted or substituted with 1 substituent selected from halo, —OH, —$NH_2$, —C≡N, —$NO_2$, —SH, $(C_1\text{-}C_6)$alkyl or $(C_1\text{-}C_6)$alkoxy. In another embodiment, at least one of $R^1$ is H and $R^2$ is unsubstituted (5- or 6-membered)heteroaryl. In another embodiment, at least one of $R^1$ is H and $R^2$ is (5- or 6-membered)heteroaryl substituted with 1 substituent selected from halo, —OH, —$NH_2$, —C≡N, —$NO_2$, —SH, $(C_1\text{-}C_6)$alkyl or $(C_1\text{-}C_6)$alkoxy.

In some embodiments, each $R^1$ is H and $R^2$ is (5- or 6-membered)heteroaryl, wherein said heteroaryl is unsubstituted or substituted with 1, 2 or 3 substituent(s) independently selected from $R^4$. In some embodiments, each $R^1$ is H and $R^2$ is (5- or 6-membered)heteroaryl, wherein said heteroaryl is unsubstituted or substituted with 1, 2 or 3 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, each $R^1$ is H and $R^2$ is (5- or 6-membered)heteroaryl, wherein said heteroaryl is unsubstituted or substituted with 1 or 2 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, each $R^1$ is H and $R^2$ is (5- or 6-membered)heteroaryl, wherein said heteroaryl is unsubstituted or substituted with 1 substituent selected from halo, —OH, —$NH_2$, —C≡N, —$NO_2$, —SH, $(C_1\text{-}C_6)$alkyl or $(C_1\text{-}C_6)$alkoxy. In another embodiment, each $R^1$ is H and $R^2$ is unsubstituted (5- or 6-membered)heteroaryl. In another embodiment, each $R^1$ is H and $R^2$ is (5- or 6-membered)heteroaryl substituted with 1 substituent selected from halo, —OH, —$NH_2$, —C≡N, —$NO_2$, —SH, $(C_1\text{-}C_6)$alkyl or $(C_1\text{-}C_6)$alkoxy.

In some embodiments, at least one of $R^1$ is $(C_1)$alkyl and $R^2$ is (5- or 6-membered)heteroaryl, wherein said heteroaryl is unsubstituted or substituted with 1, 2 or 3 substituent(s) independently selected from $R^4$. In some embodiments, at least one of $R^1$ is $(C_1)$alkyl and $R^2$ is (5- or 6-membered)heteroaryl, wherein said heteroaryl is unsubstituted or substituted with 1, 2 or 3 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, at least one of $R^1$ is $(C_1)$alkyl and $R^2$ is (5- or 6-membered)heteroaryl, wherein said heteroaryl is unsubstituted or substituted with 1 or 2 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, at least one of $R^1$ is $(C_1)$alkyl and $R^2$ is (5- or 6-membered)heteroaryl, wherein said heteroaryl is unsubstituted or substituted with 1 substituent selected from halo, —OH, —$NH_2$, —C≡N, —$NO_2$, —SH, $(C_1\text{-}C_6)$alkyl or $(C_1\text{-}C_6)$alkoxy. In another embodiment, at least one of $R^1$ is $(C_1)$alkyl and $R^2$ is unsubstituted (5- or 6-membered)heteroaryl. In another embodiment, at least one of $R^1$ is $(C_1)$alkyl and $R^2$ is (5- or 6-membered)heteroaryl substituted with 1 substituent selected from halo, —OH, —$NH_2$, —C≡N, —$NO_2$, —SH, $(C_1\text{-}C_6)$alkyl or $(C_1\text{-}C_6)$alkoxy.

In some embodiments, each $R^1$ is $(C_1)$alkyl and $R^2$ is (5- or 6-membered)heteroaryl, wherein said heteroaryl is unsubstituted or substituted with 1, 2 or 3 substituent(s) independently selected from $R^4$. In some embodiments, each $R^1$ is $(C_1)$alkyl and $R^2$ is (5- or 6-membered)heteroaryl, wherein said heteroaryl is unsubstituted or substituted with 1, 2 or 3 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, each $R^1$ is $(C_1)$alkyl and $R^2$ is (5- or 6-membered)heteroaryl, wherein said heteroaryl is unsubstituted or substituted with 1 or 2 substituent(s) independently selected from halo, —OH, —$NH_2$, —C≡N, —$NO_2$, —SH, $(C_1\text{-}C_6)$alkyl or $(C_1\text{-}C_6)$alkoxy. In another embodiment, each $R^1$ is $(C_1)$alkyl and $R^2$ is (5- or 6-membered)heteroaryl, wherein said heteroaryl is unsubstituted or substituted with 1 substituent selected from halo, —OH, —$NH_2$, —C≡N, —$NO_2$, —SH, $(C_1\text{-}C_6)$alkyl or $(C_1\text{-}C_6)$alkoxy. In another embodiment, each $R^1$ is $(C_1)$alkyl and $R^2$ is unsubstituted (5- or 6-membered)heteroaryl. In another embodiment, each $R^1$ is $(C_1)$alkyl and $R^2$ is ((5- or 6-membered)heteroaryl substituted with 1 substituent selected from halo, —OH, —$NH_2$, —C≡N, —$NO_2$, —SH, $(C_1\text{-}C_6)$alkyl or $(C_1\text{-}C_6)$alkoxy.

In some embodiments, at least one of $R^1$ is H and X is S. In another embodiment, at least one of $R^1$ is H and X is NH. In another embodiment, at least one of $R^1$ is H and X is O. In another embodiment, at least one $R^1$ is H and X is $N(C_1\text{-}C_6)$alkyl. In another embodiment, at least one $R^1$ is H and X is $NCH_3$.

In some embodiments, each $R^1$ is H and X is S. In another embodiment, each $R^1$ is H and X is NH. In another embodiment, each $R^1$ is H and X is O. In another embodiment, each $R^1$ is H and X is $N(C_1\text{-}C_6)$alkyl. In another embodiment, each $R^1$ is H and X is $NCH_3$.

In some embodiments, at least one of $R^1$ is $(C_1)$alkyl and X is S. In another embodiment, at least one of $R^1$ is $(C_1)$alkyl and X is NH. In another embodiment, at least one of $R^1$ is ($C_1$)alkyl and X is O. In another embodiment, at least one $R^1$ is H and X is N($C_1$-$C_6$)alkyl. In another embodiment, at least one $R^1$ is H and X is $NCH_3$.

In some embodiments, each $R^1$ is ($C_1$)alkyl and X is S. In another embodiment, each $R^1$ is ($C_1$)alkyl and X is NH. In another embodiment, each $R^1$ is ($C_1$)alkyl and X is O. In another embodiment, each $R^1$ is H and X is N($C_1$-$C_6$)alkyl. In another embodiment, each $R^1$ is H and X is $NCH_3$.

In addition to the compounds of formulae (1)-(4), the present disclosure provides prodrugs thereof. In particular, the present disclosure provides compound of formula (5):

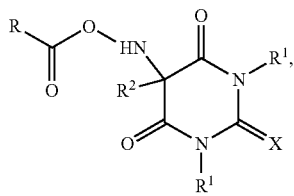

(5)

or a pharmaceutically acceptable salt thereof, wherein:

$R^1$, $R^2$ and X together are as defined herein for each of compounds of formulae (1), (1a), (1a-1), (1a-2), (1b), (1c), (1d), (2), (3), (3a), (3a-1), (3b), (3c), (3d), (4), (4a), (4b), (4c) and (4d); and R is hydrogen, —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —$NH_2$, —NH—($C_1$-$C_4$)alkyl, or —N(($C_1$-$C_4$)alkyl)$_2$, wherein said —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —NH—($C_1$-$C_4$)alkyl, or —N(($C_1$-$C_4$)alkyl)$_2$ can be unsubstituted or substituted with 1, 2 or 3 substituents selected from halo, —($C_1$-$C_6$)alkyl, —($C_2$-$C_4$)alkenyl, —($C_2$-$C_3$)alkynyl, -(5- or 6-membered)heteroaryl, —O—($C_1$-$C_6$)alkyl, —S—($C_1$-$C_6$)alkyl, —C(halo)$_3$, —CH(halo)$_2$, —$CH_2$(halo), —CN, —$NO_2$, —$NH_2$, —NH—($C_1$-$C_4$)alkyl, —N(—($C_1$-$C_4$)alkyl)$_2$, —C(O)($C_1$-$C_4$)alkyl, —C(O)O($C_1$-$C_4$)alkyl, —OC(O)($C_1$-$C_4$)alkyl, —OC(O)$NH_2$, —S(O)($C_1$-$C_4$)alkyl, or —S(O)$_2$($C_1$-$C_4$)alkyl.

In particular embodiments, R is methyl, ethyl, benzyl, or phenyl. In particular embodiments, R is methyl or ethyl. In particular embodiments, R is methyl. In particular embodiments, R is ethyl. In particular embodiments, R is benzyl or phenyl. In particular embodiments, R is benzyl. In particular embodiments, R is phenyl.

Table 1 provides representative compounds of the disclosure.

TABLE 1

| Compound No. | Compound Structure | Compound Name |
|---|---|---|
| 1 | | 5-(N-hydroxylamino)-5-benzyl-N,N-dimethylbarbituric acid |
| 2 | 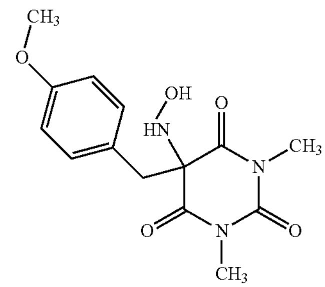 [SMILES: COc1ccc(CC2(NO)C(=O)N(C)C(=O)N(C)C2=O)cc1] | 5-(N-hydroxylamino)-5-(4-methoxybenzyl)-N,N-dimethylbarbituric acid |
| 3 | 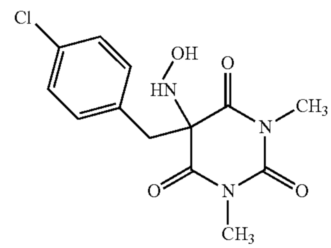 [SMILES: CN1C(=O)N(C)C(=O)C(Cc2ccc(Cl)cc2)(NO)C1=O] | 5-(N-hydroxylamino)-5-(4-chlorobenzyl)-N,N-dimethylbarbituric acid |
| 4 | 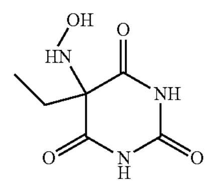 | 5-(N-hydroxylamino)-5-ethyl-barbituric acid |
| 5 | 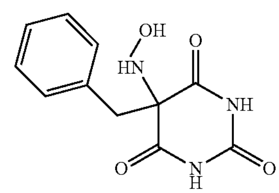 [SMILES: O=C1NC(=O)C(Cc2ccccc2)(NO)C(=O)N1] | 5-(N-hydroxylamino)-5-benzyl-barbituric acid |
| 6 | 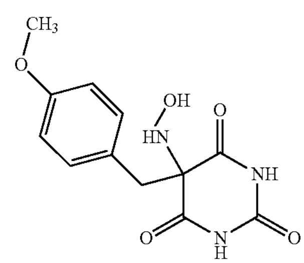 [SMILES: COc1ccc(CC2(NO)C(=O)NC(=O)NC2=O)cc1] | 5-(N-hydroxylamino)-5-(4-methoxybenzyl)-barbituric acid |
| 7 | 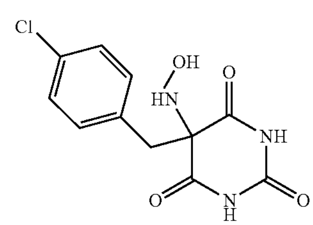 [SMILES: O=C1NC(=O)C(Cc2ccc(Cl)cc2)(NO)C(=O)N1] | 5-(N-hydroxylamino)-5-(4-chlorobenzyl)-barbituric acid |

TABLE 1-continued

| Compound No. | Compound Structure | Compound Name |
|---|---|---|
| 8 | 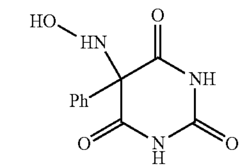 [SMILES: O=C1NC(=O)C(NO)(c2ccccc2)C(=O)N1] | 5-(N-hydroxylamino-5-phenyl-barbituric acid |
| 9 | 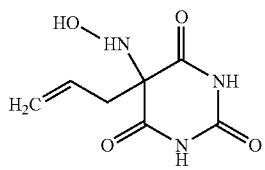 | 5-(N-hydroxylamino)-5-(2-propen-1-yl)-barbituric acid |
| 10 | 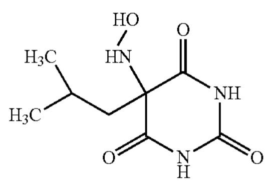 | 5-(N-hydroxylamino)-5-(2-methylpropyl)-barbituric acid |
| 11 | 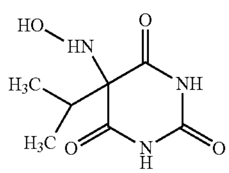 | 5-(N-hydroxylamino)-5-(1-methylethyl)-barbituric acid |
| 12 | 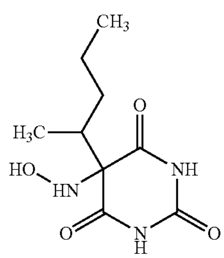 [SMILES: CCCC(C)C1(NO)C(=O)NC(=O)NC1=O] | 5-(N-hydroxylamino)-5-(1-methylbutyl)-barbituric acid |
| 13 | 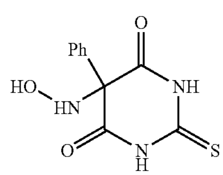 [SMILES: O=C1NC(=S)NC(=O)C1(NO)c1ccccc1] | 5-(N-hydroxylamino)-5-phenyl-thiobarbituric acid |
| 14 | 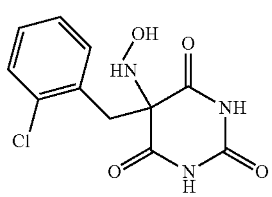 [SMILES: O=C1NC(=O)C(Cc2ccccc2Cl)(NO)C(=O)N1] | 5-(N-hydroxylamino)-5-(2-chlorobenzyl)-barbituric acid |
| 15 | 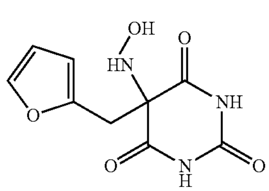 [SMILES: O=C1NC(=O)C(Cc2ccco2)(NO)C(=O)N1] | 5-(N-hydroxylamino)-5-(2-furylmethyl)-barbituric acid |
| 16 | 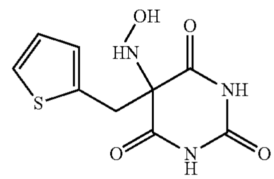 [SMILES: O=C1NC(=O)C(Cc2cccs2)(NO)C(=O)N1] | 5-(N-hydroxylamino)-5-(2-thienylmethyl)-barbituric acid |
| 17 | 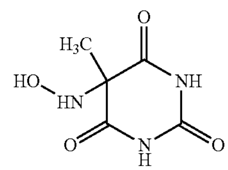 | 5-(N-hydroxylamino)-5-methyl-barbituric acid |
| 18 | 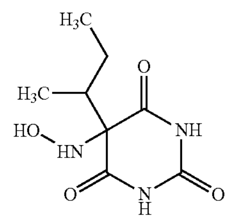 | 5-(N-hydroxylamino)-5-(1-methylpropyl)-barbituric acid |
| 19 | 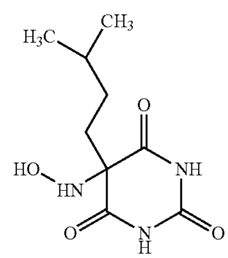 | 5-(hydroxylamino)-5-(3-methylbutyl) barbituric acid |
| 20 | 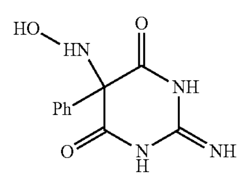 [SMILES: N=C1NC(=O)C(NO)(c2ccccc2)C(=O)N1] | 5-(hydroxyamino)-2-imino-5-phenyldihydro-pyrimidine-4,6(1H,5H)-dione |
| 21 | 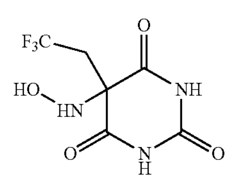 | 5-(hydroxylamino)-5-(2,2,2-trifluoroethyl) barbituric acid |
| 22 | 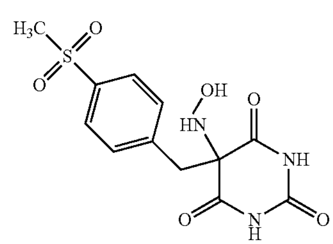 [SMILES: CS(=O)(=O)c1ccc(CC2(NO)C(=O)NC(=O)NC2=O)cc1] | 5-(hydroxylamino)-5-(4-(methylsulfonyl) benzyl) barbituric acid |

TABLE 1-continued

| Compound No. | Compound Name |
|---|---|
| 23 | 5-(hydroxylamino)-5-(benzo[d][1,3]dioxol-5-ylmethyl)barbituric acid |
| 24 | 5-(hydroxylamino)-5-(pyridin-4-ylmethyl)barbituric acid |
| 25 | 5-(hydroxylamino)-5-(3-ethyl-5-hydroxy-6-methylpyridin-4-ylmethyl)barbituric acid |
| 26 | 5-(hydroxylamino)-5-(3-hydroxy-5-(hydroxylmethyl)-2-methylpyridin-4-ylmethyl)barbituric acid |
| 27 | 5-(hydroxylamino)5-(2-(methylthio)ethyl)barbituric acid |
| 28 | 5-(hydroxyamino)-5-(4-hydroxybenzyl)barbituric acid |
| 29 | 5-((1H-indol-2-yl)methyl)-5-(hydroxyamino)barbituric acid |
| 30 | 2-(5-(hydroxyamino)-2,4,6-trioxohexahydropyrimidin-5-yl)acetic acid |
| 31 | 3-(5-(hydroxyamino)-2,4,6-trioxohexahydropyrimidin-5-yl)propanoic acid |
| 32 | 2-(5-(hydroxyamino)-2,4,6-trioxohexahydropyrimidin-5-yl)acetamide |
| 33 | 3-(5-(hydroxyamino)-2,4,6-trioxohexahydropyrimidin-5-yl)propanamide |
| 34 | 5-((1H-imidazol-5-yl)methyl)-5-(hydroxyamino)barbituric acid |
| 35 | 5-(4-aminobutyl)-5-(hydroxyamino)barbituric acid |
| 36 | 1-(3-(5-(hydroxyamino)-2,4,6-trioxohexahydropyrimidin-5-yl)propyl)guanidine |

4.3 Measuring Nitroxyl Donating Ability

Compounds are easily tested for nitroxyl donation by routine experiments. Although it is typically impractical to directly measure whether nitroxyl is donated, several analytical approaches are accepted as suitable for determining whether a compound donates nitroxyl. For example, the compound of interest can be placed in solution, for example in phosphate buffered saline ("PBS") or in a phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectrometry. If the gas $N_2O$ is formed (which occurs by HNO dimerization), the test is positive for nitroxyl donation and the compound is deemed to be a nitroxyl donor.

Alternatively, the compound of interest can be placed in a solution of tris(4,6-dimethyl-3-sulfanatophenyl)phosphine trisodium salt (TXPTS) in e.g., a phosphate buffered solution at a pH of about 7.4. The amount of nitroxyl released from the compound of interest can be detected by monitoring the formation of TXPTS aza-ylide by $^1$H NMR. See Reisz et al., *Org. Lett.* 11:2719-2721 (2009), Reisz et al., *J. Am. Chem. Soc.* 133:11675-11685 (2011) and Guthrie et al., *J. Org. Chem.* 80:1338-1348 (2015). Accordingly, if TXPTS aza-ylide is formed, the test is positive for nitroxyl donation.

If desired, nitroxyl donation also can be detected by exposing the test compound to metmyoglobin ("$Mb^{3+}$"). See Bazylinski et al., *J. Amer. Chem. Soc.* 107(26):7982-7986 (1985). Nitroxyl reacts with $Mb^{3+}$ to form a $Mb^{2+}$-NO complex, which can be detected by changes in the ultraviolet/visible spectrum or by electron paramagnetic resonance ("EPR"). The $Mb^{2+}$-NO complex has an EPR signal centered around a g-value of about 2. Nitric oxide, on the other hand, reacts with $Mb^{3+}$ to form an $Mb^{3+}$-NO complex that has a negligible, if any, EPR signal. Accordingly, if a compound reacts with $Mb^{3+}$ to form a complex detectable by common methods, such as ultraviolet/visible or EPR, then the test is positive for nitroxyl donation.

The level of nitroxyl donating ability can be expressed as a percentage of a compound's theoretical stoichiometric maximum. A compound that donates a "significant level of nitroxyl" means, in various embodiments, a compound that donates about 40% or more, about 50% or more, about 60% or more, about 70% or more, about 80% or more, about 90% or more, or about 95% or more of its theoretical maximum amount of nitroxyl. In particular embodiments, a compound donates from about 70% to about 90% of its theoretical maximum amount of nitroxyl. In particular embodiments, a compound donates from about 85% to about 95% of its theoretical maximum amount of nitroxyl. In particular embodiments, a compound donates from about 90% to about 95% of its theoretical maximum amount of nitroxyl. Compounds that donate less than about 40%, or less than about 50%, of their theoretical maximum amount of nitroxyl are still nitroxyl donors and can be used in the methods disclosed. A compound that donates less than about 50% of its theoretical amount of nitroxyl can be used in the methods disclosed, but may require higher dosing levels as compared to a compound that donates a higher level of nitroxyl.

Testing for nitroxyl donation can be performed at a physiologically relevant pH. In particular embodiments, a compound of the disclosure is capable of donating nitroxyl at physiological pH (i.e., a pH of about 7.4) and physiological temperature (i.e., a temperature of about 37° C.) (together, "physiological conditions"). In particular embodiments, a compound of the disclosure can donate about 40% or more of its theoretical maximum (i.e., 100%) amount of nitroxyl under physiological conditions. In particular embodiments, a compound of the disclosure can donate about 50% or more of its theoretical maximum amount of nitroxyl under physiological conditions. In particular embodiments, a compound of the disclosure can donate about 60% or more of its theoretical maximum amount of nitroxyl under physiological conditions. In particular embodiments, a compound of the disclosure can donate about 70% or more of its theoretical maximum amount of nitroxyl under physiological conditions. In particular embodiments, a compound of the disclosure can donate about 80% or more of its theoretical maximum amount of nitroxyl under physiological conditions. In particular embodiments, a compound of the disclosure can donate about 90% or more of its theoretical maximum amount of nitroxyl under physiological conditions.

It will be understood that a compound of the disclosure might also donate a limited amount of nitric oxide, so long as the amount of nitroxyl donation exceeds the amount of nitric oxide donation. In certain embodiments, a compound of the disclosure can donate about 25 mole % or less of nitric oxide under physiological conditions. In particular embodiments, a compound of the disclosure can donate about 20 mole % or less of nitric oxide under physiological conditions. In particular embodiments, a compound of the disclosure can donate about 15 mole % or less of nitric oxide under physiological conditions. In particular embodiments, a compound of the disclosure can donate about 10 mole % or less of nitric oxide under physiological conditions. In particular embodiments, a compound of the disclosure can donates about 5 mole % or less of nitric oxide under physiological conditions. In particular embodiments, a compound of the disclosure can donate about 2 mole % or less of nitric oxide under physiological conditions. In particular embodiments, a compound of the disclosure can donate an insignificant amount (e.g., about 1 mole % or less) of nitric oxide under physiological conditions.

4.4 Pharmaceutical Compositions

The disclosure encompasses pharmaceutical compositions comprising a nitroxyl donor at least one pharmaceutically acceptable excipient. Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in Troy, Ed., *Remington: The Science and Practice of Pharmacy*, 21$^{st}$ Ed. (Lippincott Williams & Wilkins, Baltimore, Md., 2005).

The pharmaceutical compositions can be formulated for administration in solid or liquid form, including those adapted for the following: (1) oral administration, for example, as drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; or (2) parenteral administration by, for example, subcutaneous, intramuscular, intravenous or epidural injection as, for example, a sterile solution or suspension. The pharmaceutical compositions can be for immediate, sustained or controlled release.

The compounds and pharmaceutical compositions disclosed herein can be prepared as any appropriate unit dosage form, such as capsules, sachets, tablets, powder, granules, solution, suspension in an aqueous liquid, suspension in a non-aqueous liquid, oil-in-water liquid emulsion, water-in-oil liquid emulsion, liposomes or bolus.

4.4.1 Compositions for Parenteral Administration

The disclosure provides nitroxyl donating compositions for parenteral (e.g., intravenous) administration. In one embodiment, the pharmaceutical composition is formulated for intravenous administration by continuous infusion.

Various embodiments of pharmaceutical compositions suitable for parenteral administration include, without limitation, either aqueous sterile injection solutions or non-aqueous sterile injection solutions, each containing, for example, anti-oxidants, buffers, bacteriostats and solutes that render the formulation isotonic with the blood of the intended recipient; and aqueous sterile suspensions and non-aqueous sterile suspensions, each containing, for example, suspending agents and thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use. Alternately, the formulation can be in the form of a liquid.

Pharmaceutical compositions administered parenterally can be administered in an acidic, neutral or basic solution. In one embodiment, pharmaceutical compositions comprising a nitroxyl donor can be formulated in an acidic solution having a pH of from about 4 to about 5, for instance, a pH of about 4, about 4.5, about 4.8, or about 5, including values there between.

Accordingly, in certain embodiments, an N-hydroxylamino-barbituric acid type nitroxyl donor useful in a pharmaceutical composition of the disclosure is formulated for parenteral injection at a pH of from about 5 to about 6.5 in some embodiments, from about 5 to about 6 in some embodiments, from about 5.5 to about 6 in some embodiments, from about 5 to about 5.5 in some embodiments, from about 5.2 to about 6.2 in some embodiments, from about 5.5 to about 6.2 in some embodiments, from about 5.8 to about 6.2 in some embodiments, and at a pH of about 6 in particular embodiments. In another embodiment, an N-hydroxylamino-barbituric acid type nitroxyl donor useful in a pharmaceutical composition of the disclosure is formulated for parenteral injection at a pH of about 5.

To achieve the desired pH of the pharmaceutical composition, an N-hydroxylamino-barbituric acid type nitroxyl donor can be formulated in an aqueous buffer. For example, an N-hydroxylamino-barbituric acid type nitroxyl donor can be formulated in a phosphate or acetate buffer. In particular embodiments, an N-hydroxylamino-barbituric acid type nitroxyl donor is formulated in a potassium phosphate or sodium phosphate buffer. In other embodiments, an N-hydroxylamino-barbituric acid type nitroxyl donor is formulated in a potassium phosphate buffer or sodium phosphate buffer. In other embodiments, an N-hydroxylamino-barbituric acid type nitroxyl donor is formulated in a potassium citrate buffer or sodium citrate buffer.

The aqueous buffer can also include an appropriate sugar in order to maintain an appropriate osmolality. For instance, the pharmaceutical composition can include an appropriate amount of dextrose. The pharmaceutical compositions can generally prepared by diluting a concentrate comprising an N-hydroxylamino-barbituric acid type nitroxyl donor, optionally a cyclodextrin (see Section 4.3.3) and an appropriate buffer into an aqueous solution comprising 5% dextrose (D5W) or 2.5% dextrose (D2.5W).

4.4.2 Compositions for Oral Administration

Pharmaceutical compositions comprising an N-hydroxylamino-barbituric acid type nitroxyl donors can be formulated for oral administration. Compounds for oral administration can be formulated as liquid or solid dosage forms. In particular embodiments where the nitroxyl donors are formulated as oral liquid dosage forms, polyethylene glycol (e.g., polyethylene glycol 300 (PEG300) or polyethylene glycol 400 (PEG400)) can usefully serve as an excipient.

Tablets for oral administration can be made by compression or molding, optionally with one or more accessory ingredients. Compressed tablets can be prepared by compressing in a suitable machine the therapeutic agent or agents in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide slow or controlled release of the active ingredient therein. Methods of formulating such slow or controlled release compositions of pharmaceutically active ingredients, such as the therapeutic agents herein and other compounds known in the art, are known in the art and disclosed in issued U.S. patents, some of which include, but are not limited to, U.S. Pat. Nos. 4,369,174, 4,842,866, and the references cited therein. Coatings can be used for delivery of compounds to the intestine (see, e.g., U.S. Pat. Nos. 6,638,534, 5,217,720, 6,569,457, and the references cited therein). An artisan will recognize that in addition to tablets, other dosage forms can be formulated to provide slow or controlled release of the active ingredient. Such dosage forms include, but are not limited to, capsules, granulations and gel-caps.

4.5 Methods of Using the Compounds and Pharmaceutical Compositions of the Disclosure In one aspect, the disclosure provides a method of increasing in vivo nitroxyl levels, comprising administering to a patient in need thereof an effective amount of a compound or a pharmaceutical composition as disclosed herein. In various embodiments, the patient has, is suspected of having, or is at risk of having or developing a condition that is responsive to nitroxyl therapy.

In particular embodiments, the disclosure provides a method of treating, preventing or delaying the onset and/or development of a condition, comprising administering to a patient (including a patient identified as in need of such treatment, prevention or delay) an effective amount of a compound or a pharmaceutical composition as disclosed herein. Identifying a patient in need thereof can be in the judgment of a physician, clinical staff, emergency response personnel or other health care professional and can be subjective (e.g., opinion) or objective (e.g., measurable by a test or diagnostic method).

Particular conditions embraced by the methods disclosed herein include, without limitation, cardiovascular diseases, ischemia/reperfusion injury, pulmonary hypertension (PH), alcoholism, vascular dysfunction, and cancer.

4.5.1 Cardiovascular Diseases

In one embodiment, the disclosure provides a method of treating a cardiovascular disease, comprising administering an effective amount of a compound or a pharmaceutical composition as disclosed herein to a patient in need thereof.

Examples of cardiovascular diseases and symptoms that can usefully be treated with the compounds and compositions disclosed herein include cardiovascular diseases that are responsive to nitroxyl therapy, coronary obstructions, coronary artery disease (CAD), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

4.5.1.1 Heart Failure

The nitroxyl donating compositions of the disclosure can be used to treat patients suffering from heart failure. The heart failure can be of any type or form, including any of the heart failures disclosed herein. Nonlimiting examples of heart failure include early stage heart failure, Class I, II, III and IV heart failure, acute heart failure, congestive heart failure (CHF) and acute congestive heart failure. In one embodiment, the compounds and compositions of the disclosure can be used to treat acute decompensated heart failure.

In embodiments in which the nitroxyl donating compositions of the disclosure are used to treat patients suffering from heart failure, another active agent that treats heart failure can also be administered. In one such embodiment, the nitroxyl donor can be administered in conjunction with a positive inotrope such as a beta-agonist. Examples of beta-agonists include, without limitation, dopamine, dobutamine, isoproterenol, analogs of such compounds and derivatives of such compounds. In another embodiment, nitroxyl donor can be administered in conjunction with a beta-adrenergic receptor antagonist (also referred to herein as beta-antagonist or beta-blocker). Examples of beta-antagonists include, without limitation, propranolol, metoprolol, bisoprolol, bucindolol, and carvedilol.

4.5.1.2 Ischemia/Reperfusion Injury

In another embodiment, the disclosure provides a method of treating, preventing or delaying the onset and/or development of ischemia/reperfusion injury, comprising administering an effective amount of a compound or pharmaceutical composition as disclosed herein to a subject in need thereof.

In a particular embodiment, the method is for preventing ischemia/reperfusion injury. In a particular embodiment, a pharmaceutical composition of the disclosure is administered prior to the onset of ischemia. In a particular embodiment, a pharmaceutical composition of the disclosure is administered prior to procedures in which myocardial ischemia can occur, for example an angioplasty or surgery, such as a coronary artery bypass graft surgery. In a particular embodiment, a pharmaceutical composition of the disclosure is administered after ischemia but before reperfusion. In a particular embodiment, a pharmaceutical composition of the disclosure is administered after ischemia and reperfusion.

In another embodiment, a pharmaceutical composition of the disclosure can be administered to a patient who is at risk for an ischemic event. In a particular embodiment, a pharmaceutical composition of the disclosure is administered to a patient at risk for a future ischemic event, but who has no present evidence of ischemia. The determination of whether a patient is at risk for an ischemic event can be performed by any method known in the art, such as by examining the patient or the patient's medical history. In a particular embodiment, the patient has had a prior ischemic event. Thus, the patient can be at risk of a first or subsequent ischemic event. Examples of patients at risk for an ischemic event include patients with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction, elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, myocardial infarction (MI) and neurovascular ischemia, such as a cerebrovascular accident (CVA).

In another embodiment, the subject of treatment is an organ that is to be transplanted. In a particular embodiment, a pharmaceutical composition of the disclosure can be administered prior to reperfusion of the organ in a transplant recipient. In a particular embodiment, a pharmaceutical composition of the disclosure can be administered prior to removal of the organ from the donor, for example through the perfusion cannulas used in the organ removal process. If the organ donor is a live donor, for example a kidney donor, the compounds or pharmaceutical compositions of the disclosure can be administered to the organ donor. In a particular embodiment, the compounds or pharmaceutical compositions of the disclosure are administered by storing the organ in a solution comprising the compound or pharmaceutical composition. For example, a compound or pharmaceutical composition of the disclosure can be included in the organ preservation solution, such as the University of Wisconsin "UW" solution, which is a solution comprising hydroxyethyl starch substantially free of ethylene glycol, ethylene chlorohydrin and acetone (see U.S. Pat. No. 4,798, 824). In a particular embodiment, a pharmaceutical composition of the disclosure that is administered is such that ischemia/reperfusion injury to the tissues of the organ is reduced upon reperfusion in the recipient of transplanted organ. In a particular embodiment, the method reduces tissue necrosis (the size of infarct) in at-risk tissues.

Ischemia/reperfusion injury can damage tissues other than those of the myocardium and the disclosed subject matter embraces methods of treating or preventing such damage. In various embodiments, the ischemia/reperfusion injury is non-myocardial. In particular embodiments, the method reduces injury from ischemia/reperfusion in the tissue of the brain, liver, gut, kidney, bowel, or any part of the body other than the myocardium. In another embodiment, the patient is at risk for such injury. Selecting a person at risk for non-myocardial ischemia could include a determination of the indicators used to assess risk for myocardial ischemia. However, other factors can indicate a risk for ischemia/ reperfusion in other tissues. For example, surgery patients often experience surgery related ischemia. Thus, patients scheduled for surgery could be considered at risk for an ischemic event. The following risk factors for stroke (or a subset of these risk factors) could demonstrate a patient's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, *Postgrad. Med.* 107(6):34-50 (2000). Further, complications of untreated infectious diarrhea in the elderly can include myocardial, renal, cerebrovascular and intestinal ischemia. Slotwiner-Nie et al., *Gastroenterol. Clin. N. Amer.* 30(3):625-635 (2001). Alternatively, patients could be selected based on risk factors for ischemic bowel, kidney and/or liver disease. For example, treatment would be initiated in elderly patients at risk of hypotensive episodes (such as surgical blood loss). Thus, patients presenting with such an indication would be considered at risk for an ischemic event. In another embodiment, the patient has any one or more of the conditions listed herein, such as diabetes mellitus and hypertension. Other conditions that can result in ischemia, such as cerebral arteriovenous malformation, could demonstrate a patient's risk for an ischemic event.

4.5.2 Pulmonary Hypertension

In another embodiment, a pharmaceutical composition of the disclosure can be used to prevent or delay the onset and/or development of pulmonary hypertension. In one such embodiment, a pharmaceutical composition of the disclosure can be used to prevent or delay the onset and/or development of pulmonary arterial hypertension (PAH).

In another embodiment, the disclosure provides a method of reducing mean pulmonary arterial pressure (MPAP), comprising administering an effective amount of a compound or a pharmaceutical composition disclosed herein to a patient in need thereof. In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to about 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

4.6 Administration Modes, Regimens and Dose Levels

The compounds and pharmaceutical compositions of the disclosure can be administered via parenteral (e.g., subcutaneous, intramuscular, intravenous or intradermal) administration. In certain embodiments, the N-hydroxylamino-barbituric acid type nitroxyl donor useful in a pharmaceutical composition of the disclosure is administered by intravenous infusion. In other embodiments, the compounds and pharmaceutical compositions of the disclosure can be administered by oral administration.

When a pharmaceutical composition comprising a compound of the present disclosure is administered, dosages are expressed based on the amount of active pharmaceutical ingredient, i.e., the amount of nitroxyl donor compound(s) of the disclosure present in the pharmaceutical composition. For intravenous administration, the dose can usefully be expressed per unit time, either as a fixed amount per unit time or as a weight-based amount per unit time.

In various embodiments, a N-hydroxylamino-barbituric acid type nitroxyl donor in a pharmaceutical composition of the disclosure is administered intravenously in an amount of at least about 0.1 µg/kg/min, at least about 0.2 µg/kg/min, at least about 0.3 µg/kg/min, at least about 0.4 µg/kg/min, at least about 0.5 µg/kg/min, at least about 1 µg/kg/min, at least about 2.5 µg/kg/min, at least about 5 µg/kg/min, at least about 7.5 µg/kg/min, at least about 10 µg/kg/min, at least about 11 µg/kg/min, at least about 12 µg/kg/min, at least about 13 µg/kg/min, at least about 14 µg/kg/min, at least about 15 µg/kg/min, at least about 16 µg/kg/min, at least about 17 µg/kg/min, at least about 18 µg/kg/min, at least about 19 µg/kg/min, at least about 20 µg/kg/min, at least about 21 µg/kg/min, at least about 22 µg/kg/min, at least about 23 µg/kg/min, at least about 24 µg/kg/min, at least about 25 µg/kg/min, at least about 26 µg/kg/min, at least about 27 µg/kg/min, at least about 28 µg/kg/min, at least about 29 µg/kg/min, at least about 30 µg/kg/min, at least about 31 µg/kg/min, at least about 32 µg/kg/min, at least about 33 µg/kg/min, at least about 34 µg/kg/min, at least about 35 µg/kg/min, at least about 36 µg/kg/min, at least about 37 µg/kg/min, at least about 38 µg/kg/min, at least about 39 µg/kg/min, or at least about 40 µg/kg/min.

In various embodiments, the N-hydroxylamino-barbituric acid type nitroxyl donor useful in a pharmaceutical composition of the disclosure is administered intravenously in an amount of no more than about 100 µg/kg/min, no more than about 90 µg/kg/min, no more than about 80 µg/kg/min, no more than about 70 µg/kg/min, no more than about 60 µg/kg/min, no more than about 50 µg/kg/min, no more than about 49 µg/kg/min, no more than about 48 µg/kg/min, no more than about 47 µg/kg/min, no more than about 46 µg/kg/min, no more than about 45 µg/kg/min, no more than about 44 µg/kg/min, no more than about 43 µg/kg/min, no more than about 42 µg/kg/min, no more than about 41 µg/kg/min, no more than about 40 µg/kg/min, no more than about 39 µg/kg/min, no more than about 38 µg/kg/min, no more than about 37 µg/kg/min, no more than about 36 µg/kg/min, no more than about 35 µg/kg/min, no more than about 34 µg/kg/min, no more than about 33 µg/kg/min, no more than about 32 µg/kg/min, no more than about 31 µg/kg/min, or no more than about 30 µg/kg/min In some embodiments, the N-hydroxylamino-barbituric acid type nitroxyl donor useful in a pharmaceutical composition of the disclosure is administered intravenously in an amount ranging from about 0.1 µg/kg/min to about 100 µg/kg/min, about 1 µg/kg/min to about 100 µg/kg/min, about 2.5 µg/kg/min to about 100 µg/kg/min, about 5 µg/kg/min to about 100 µg/kg/min, about 10 µg/kg/min to about 100 µg/kg/min, about 1.0 µg/kg/min to about 80 µg/kg/min, from about 10.0 µg/kg/min to about 70 µg/kg/min, from about 20 µg/kg/min to about 60 µg/kg/min, from about 15 µg/kg/min to about 50 µg/kg/min, from about 0.01 µg/kg/min to about 1.0 µg/kg/min, from about 0.01 µg/kg/min to about 10 µg/kg/min, from about 0.1 µg/kg/min to about 1.0 µg/kg/min, from about 0.1 µg/kg/min to about 10 µg/kg/min, from about 1.0 µg/kg/min to about 5 µg/kg/min, from about 70 µg/kg/min to about 100 µg/kg/min, or from about 80 µg/kg/min to about 90 µg/kg/min.

In particular embodiments, the N-hydroxylamino-barbituric acid type nitroxyl donor useful in a pharmaceutical composition of the disclosure is administered intravenously in an amount ranging from about 10 µg/kg/min to about 50

µg/kg/min, about 20 µg/kg/min to about 40 µg/kg/min, about 25 µg/kg/min to about 35 µg/kg/min, or about 30 µg/kg/min to about 40 µg/kg/min. In particular embodiments, an N-hydroxylamino barbituric acid type nitroxyl donor useful in a pharmaceutical composition of the disclosure is administered intravenously in an amount of from about 20 µg/kg/min to about 30 µg/kg/min.

In a variety of embodiments, including various oral administration embodiments, the compounds or pharmaceutical compositions of the disclosure are administered according to a weight-based daily dosing regimen, either as a single daily dose (QD) or in multiple divided doses administered, e.g., twice a day (BID), three times a day (TID), or four times a day (QID).

In certain embodiments, the N-hydroxylamino-barbituric acid type nitroxyl donor useful in a pharmaceutical composition of the disclosure is administered in a dose of at least about 0.5 mg/kg/d, at least about 0.75 mg/kg/d, at least about 1.0 mg/kg/d, at least about 1.5 mg/kg/d, at least about 2 mg/kg/d, at least about 2.5 mg/kg/d, at least about 3 mg/kg/d, at least about 4 mg/kg/d, at least about 5 mg/kg/d, at least about 7.5 mg/kg/d, at least about 10 mg/kg/d, at least about 12.5 mg/kg/d, at least about 15 mg/kg/d, at least about 17.5 mg/kg/d, at least about 20 mg/kg/d, at least about 25 mg/kg/d, at least about 30 mg/kg/d, at least about 35 mg/kg/d, at least about 40 mg/kg/d, at least about 45 mg/kg/d, at least about 50 mg/kg/d, at least about 60 mg/kg/d, at least about 70 mg/kg/d, at least about 80 mg/kg/d, at least about 90 mg/kg/d, or at least about 100 mg/kg/d.

In certain embodiments, the N-hydroxylamino-barbituric acid type nitroxyl donor useful in a pharmaceutical composition of the disclosure is administered at a dose of no more than about 100 mg/kg/d, no more than about 100 mg/kg/d, no more than about 90 mg/kg/d, no more than about 80 mg/kg/d, no more than about 80 mg/kg/d, no more than about 75 mg/kg/d, no more than about 70 mg/kg/d, no more than about 60 mg/kg/d, no more than about 50 mg/kg/d, no more than about 45 mg/kg/d, no more than about 40 mg/kg/d, no more than about 35 mg/kg/d, no more than about 30 mg/kg/d.

In a variety of embodiments, the dose is from about 0.001 mg/kg/d to about 10,000 mg/kg/d. In certain embodiments, the dose is from about 0.01 mg/kg/d to about 1,000 mg/kg/d. In certain embodiments, the dose is from about 0.01 mg/kg/d to about 100 mg/kg/d. In certain embodiments, the dose is from about 0.01 mg/kg/d to about 10 mg/kg/d. In certain embodiments, the dose is from about 0.1 mg/kg/d to about 1 mg/kg/d. In certain embodiments, the dose is less than about 1 g/kg/d.

In certain embodiments, the N-hydroxylamino-barbituric acid type nitroxyl donor useful in a pharmaceutical composition of the disclosure is administered in a dose range in which the low end of the range is any amount from about 0.1 mg/kg/day to about 90 mg/kg/day and the high end of the range is any amount from about 1 mg/kg/day to about 100 mg/kg/day (e.g., from about 0.5 mg/kg/day to about 2 mg/kg/day in one series of embodiments and from about 5 mg/kg/day to about 20 mg/kg/day in another series of embodiment).

In particular embodiments, the N-hydroxylamino-barbituric acid type nitroxyl donor useful in a pharmaceutical composition of the disclosure is administered in a dose amount from about 3 to about 30 mg/kg, administered from once a day (QD) to three times a day (TID).

In certain embodiments, compounds or pharmaceutical compositions of the disclosure are administered according to a flat (i.e., non-weight-based) dosing regimen, either as a single daily dose (QD) or in multiple divided doses administered, e.g., twice a day (BID), three times a day (TID), or four times a day (QID).

In various embodiments, the N-hydroxylamino-barbituric acid type nitroxyl donor useful in a pharmaceutical composition of the disclosure is administered at a dose of at least about 0.01 grams/day (g/d), at least about 0.05 g/d, at least about 0.1 g/d, at least about 0.5 g/d, at least about 1 g/d, at least about 1.5 g/d, at least about 2.0 g/d, at least about 2.5 g/d, at least about 3.0 g/d, or at least about 3.5 g/d.

In various embodiments, the N-hydroxylamino-barbituric acid type nitroxyl donor useful in a pharmaceutical composition of the disclosure is administered at a dose of no more than about 5 g/d, no more than about 4.5 g/d, no more than about 4 g/d, no more than about 3.5 g/d, no more than about 3 g/d, no more than about 2.5 g/d, or no more than about 2 g/d.

In certain embodiments, the N-hydroxylamino-barbituric acid type nitroxyl donor useful in a pharmaceutical composition of the disclosure is administered in a dose of about 0.01 grams per day to about 4.0 grams per day. In certain embodiments, the N-hydroxylamino-barbituric acid type nitroxyl donor useful in a pharmaceutical composition of the disclosure can be administered at a dose in which the low end of the range is any amount from about 0.1 mg/day to about 400 mg/day and the high end of the range is any amount from about 1 mg/day to about 4000 mg/day. In certain embodiments, the N-hydroxylamino-barbituric acid type nitroxyl donor useful in a pharmaceutical composition of the disclosure is administered in a dose of about 5 mg/day to about 100 mg/day. In various embodiments, the N-hydroxylamino-barbituric acid type nitroxyl donor useful in a pharmaceutical composition of the disclosure is administered at a dose of from about 150 mg/day to about 500 mg/day.

The dosing interval for parenteral or oral administration can be adjusted according to the needs of the patient. For longer intervals between administrations, extended release or depot formulations can be used.

An N-hydroxylamino-barbituric acid type nitroxyl donor useful in a pharmaceutical composition of the disclosure as disclosed herein can be administered prior to, at substantially the same time with, or after administration of an additional therapeutic agent. The administration regimen can include pretreatment and/or co-administration with the additional therapeutic agent. In such case, the N-hydroxylamino-barbituric acid type nitroxyl donor useful in a pharmaceutical composition of the disclosure and the additional therapeutic agent can be administered simultaneously, separately, or sequentially.

Examples of administration regimens include without limitation: administration of each compound, pharmaceutical composition or therapeutic agent in a sequential manner; and co-administration of each compound, pharmaceutical composition or therapeutic agent in a substantially simultaneous manner (e.g., as in a single unit dosage form) or in multiple, separate unit dosage forms for each compound, pharmaceutical composition or therapeutic agent.

It will be appreciated by those in the art that the "effective amount" or "dose" ("dose level") will depend on various factors such as the particular administration mode, administration regimen, compound, and pharmaceutical composition selected, as well as the particular condition and patient being treated. For example, the appropriate dose level can vary depending upon the activity, rate of excretion and potential for toxicity of the specific N-hydroxylamino-barbituric acid type nitroxyl donor useful in a pharmaceutical composition of the disclosure employed; the age, body weight, general health, gender and diet of the patient being treated; the frequency of administration; the other therapeutic agent(s) being co-administered; and the type and severity of the condition.

4.7 Kits Comprising the Compounds or Pharmaceutical Compositions

The disclosure provides kits comprising a compound or a pharmaceutical composition disclosed herein. In a particular embodiment, the kit comprises a compound or a pharmaceutical composition disclosed herein, each in dry form, and a pharmaceutically acceptable liquid diluent.

Either a compound in dry form or a pharmaceutical composition in dry form contains about 2.0% or less water by weight, about 1.5% or less water by weight, about 1.0% or less water by weight, about 0.5% or less water by weight, about 0.3% or less water by weight, about 0.2% or less water by weight, about 0.1% or less water by weight, about 0.05% or less water by weight, about 0.03% or less water by weight, or about 0.01% or less water by weight.

Pharmaceutically acceptable liquid diluents are known in the art and include but are not limited to sterile water, saline solutions, aqueous dextrose, glycerol, glycerol solutions, and the like. Other examples of suitable liquid diluents are disclosed by Nairn, "Solutions, Emulsions, Suspensions and Extracts," pp. 721-752 in Gennaro, Ed., *Remington: The Science and Practice of Pharmacy*, 20th Ed. (Lippincott Williams & Wilkins, Baltimore, Md., 2000).

In one embodiment, the kit further comprises instructions for using the compound or pharmaceutical composition. The instructions can be in any appropriate form, such as written or electronic form. In another embodiment, the instructions can be written instructions. In another embodiment, the instructions are contained in an electronic storage medium (e.g., magnetic diskette or optical disk). In another embodiment, the instructions include information as to the compound or pharmaceutical composition and the manner of administering the compound or pharmaceutical composition to a patient. In another embodiment, the instructions relate to a method of use disclosed herein (e.g., treating, preventing and/or delaying onset and/or development of a condition selected from cardiovascular diseases, ischemia/reperfusion injury, pulmonary hypertension and other conditions responsive to nitroxyl therapy).

In another embodiment, the kit further comprises suitable packaging. Where the kit comprises more than one compound or pharmaceutical composition, the compounds or pharmaceutical compositions can be packaged patiently in separate containers, or combined in one container when cross-reactivity and shelf life permit.

4.8 Methods of Synthesizing the Compounds

The compounds of this disclosure may be prepared in light of the specification using steps know to those in the art. Scheme 2 depicts a general method for making compounds of formula (1).

Scheme 2.

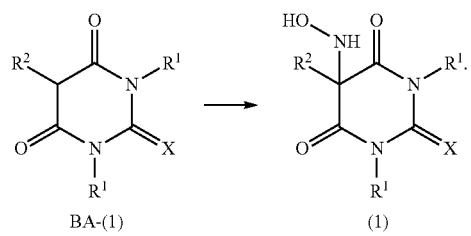

BA-(1)    (1)

Barbituric acid (BA) compound BA-(1) undergoes the nitroso-aldol reaction under standard conditions known to those skilled in the art to give compounds of formula (1). This general method can be followed to prepare compounds of formulae (2)-(4).

Should there be doubt over the agreement of a depicted chemical structure and a chemical name, the chemical name governs.

5. EXAMPLES

The following examples are presented for illustrative purposes and should not serve to limit the scope of the disclosed subject matter.

5.1 Synthesis of Compounds

The compounds disclosed herein can be made according to the methods disclosed below or by procedures known in the art. Starting materials for the reactions can be commercially available or can be prepared by known procedures or obvious modifications thereof. For example, some of the starting materials are available from commercial suppliers such as Sigma-Aldrich (St. Louis, Mo.). Others can be prepared by procedures or obvious modifications thereof disclosed in standard reference texts such as *March's Advanced Organic Chemistry* (John Wiley and Sons) and *Larock's Comprehensive Organic Transformations* (VCH Publishers).

Example 1

Preparation of 5-(N-hydroxylamino)-5-benzyl-N,N-dimethylbarbituric acid (1)

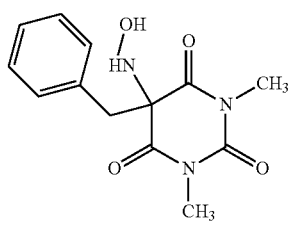 [SMILES: CN1C(=O)N(C)C(=O)C(Cc2ccccc2)(NO)C1=O]

To 5-benzyl-N,N-dimethylbarbituric acid (BA1) (1.231 g, 5 mmol), Angeli's salt (1.22 g, 10 mmol), and powdered DTPA (0.983 g, 2.5 mmol) under nitrogen at room temperature was cannulated a degassed mixture of 50% aqueous ethanol (25 mL). The reaction was allowed to vigorously stir for 10 minutes in order to dissolve all solids followed by normal stirring under a gentle stream of nitrogen for an additional 1.5 hours. At which time, precipitation of a white solid was observed. The reaction was then diluted with ethanol (200 mL) and concentrated to dryness in vacuo with minimum heat (<30° C.). The resultant material was then taken up in dichloromethane (3×20 mL), filtered through cotton, and concentrated in vacuo to give 1 as a white solid (1.385 g, 99%). Mp: 155-157° C. $^1$H NMR (400 MHz, CDCl$_3$) δ: 7.26 (m, 3H), 6.96 (m, 2H), 6.28 (d, 1H, J=3.2 Hz), 4.98 (d, 1H, J=3.4 Hz, 1H), 3.13 (s, 6H), 3.08 (s, 2H). $^{13}$C NMR (100 MHz, CDCl$_3$) δ: 170.01, 150.02, 131.75, 129.19, 128.95, 128.71, 73.64, 42.89, 28.78. HR-MS (FAB). found m/z=278.11411 (MH$^+$); calc. for $C_{13}H_{16}N_3O_4$: 278.11408.

Example 2

Preparation of 5-(N-hydroxylamino)-5-(4-methoxybenzyl)-N,N-dimethylbarbituric acid (2)

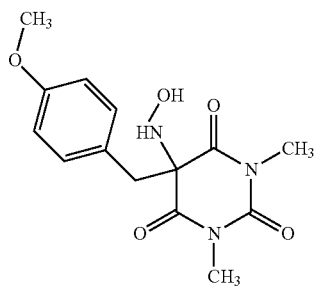 [SMILES: COc1ccc(CC2(NO)C(=O)N(C)C(=O)N(C)C2=O)cc1]

To 5-(4-methoxybenzyl)-N,N-dimethylbarbituric acid (BA2) (55 mg, 0.2 mmol), Angeli's salt (49 mg, 0.4 mmol), and powdered DTPA (39 mg, 0.1 mmol) under argon at room temperature was added a degassed mixture of 50% aqueous ethanol (1 mL). The reaction was allowed to stir for 1.5 hours, diluted with ethanol (>5 mL), and concentrated to dryness in vacuo with minimum heat (<30° C.). The material was then taken up in dichloromethane, filtered through cotton, and concentrated in vacuo to give 2 as a white solid (61 mg, 99%). Mp: 108-110° C. $^1$H NMR (400 MHz, CDCl$_3$) δ: 6.88 (d, 2H, J=8.6 Hz), 6.76 (d, 2H, J=8.7 Hz), 6.25 (br. s, 1H), 5.09 (br. s, 1H), 3.76 (s, 3H), 3.15 (s, 6H), 3.03 (s, 2H). $^{13}$C NMR (100 MHz, CDCl$_3$) δ: 159.73, 150.11, 130.32, 123.47, 114.27, 73.70, 55.43, 42.08, 28.82. HR-MS (FAB). found m/z=308.12476 (MH$^+$); calc. for $C_{14}H_{18}N_3O_5$: 308.12465.

Example 3

Preparation of 5-(N-hydroxylamino)-5-(4-chlorobenzyl)-N,N-dimethylbarbituric acid (3)

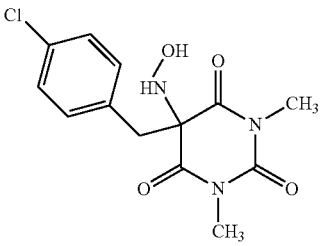 [SMILES: CN1C(=O)N(C)C(=O)C(Cc2ccc(Cl)cc2)(NO)C1=O]

To 5-(4-chlorobenzyl)-N,N-dimethylbarbituric acid (BA3) (56 mg, 0.2 mmol), Angeli's salt (49 mg, 0.4 mmol), and powdered DTPA (39 mg, 0.1 mmol) under argon at room temperature was added a degassed mixture of 50% aqueous ethanol (1 mL). The reaction was allowed to stir for 1.5 hours, diluted with ethanol (>5 mL), and concentrated to dryness in vacuo with minimum heat (<30° C.). The material was then taken up in dichloromethane, filtered through cotton, and concentrated in vacuo to give 3 as a white solid (61 mg, 99%). Mp: 155-157° C. $^1$H NMR (400 MHz, CDCl$_3$) δ: 7.24 (d, 2H, J=8.5 Hz), 6.91 (d, 2H, J=8.5 Hz), 6.23 (d, 1H, J=3.3 Hz), 4.98 (d, 1H, J=3.3 Hz), 3.17 (s, 6H), 3.06 (s, 2H). $^{13}$C NMR (100 MHz, CDCl$_3$) δ: 169.96, 149.93, 134.71, 130.60, 130.31, 129.19, 73.14, 41.74, 28.88. HR-MS (FAB). found m/z=312.07483 (MH$^+$, $^{35}$Cl), 314.07293 (MH$^+$, $^{37}$Cl); calc. for $C_{13}H_{15}ClN_3O_4$: 312.07511 (MH$^+$, $^{35}$Cl), 314.07246 (MH$^+$, $^{37}$Cl).

Example 4

Preparation of 5-(N-hydroxylamino)-5-ethyl-barbituric acid (4)

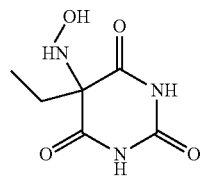

To 5-ethyl-barbituric acid (BA4) (0.781 g, 5 mmol), Angeli's salt (1.22 g, 10 mmol), and powdered DTPA (0.983 g, 2.5 mmol) under nitrogen at room temperature was cannulated a degassed mixture of 50% aqueous ethanol (25 mL). The reaction was allowed to vigorously stir for 10 minutes in order to dissolve all solids followed by normal stirring under a gentle stream of nitrogen for an additional 1.5 hours. The reaction was then diluted with ethanol (200 mL), filtered through cotton, and the clear filtrate was concentrated to dryness in vacuo with minimum heat (<30° C.). The resultant material was then triturated with diethylether and filtered to give 4 as a light yellow solid (0.707 g, 76%). Mp: >300° C. $^1$H NMR (400 MHz, DMSO-d$_6$) δ: 11.50 (br. s, 2H), 7.95 (s, 1H), 6.23 (s, 1H), 1.66 (q, 2H, J=7.5 Hz), 0.73 (t, 3H, J=7.5 Hz). $^{13}$C NMR (100 MHz, DMSO-d$_6$) δ: 172.07, 149.96, 70.88, 26.92, 7.79. HR-MS (FAB). found m/z=188.06752 (MH$^+$); calc. for $C_6H_{10}N_3O_4$: 188.06713 (MH$^+$).

Example 5

Preparation of 5-(N-hydroxylamino)-5-benzyl-barbituric acid (5)

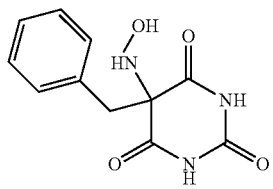

In a solution of 50% v/v aqueous ethanol (10 mL), 5-benzyl-barbituric acid (BA5) (0.044 g, 0.2 mmol), N-tert-butoxycarbonyl-hydroxylamine (0.032 g, 0.24 mmol), and potassium carbonate (0.050 g) were dissolved under sonication for 30 minutes at 25° C. To the solution, sodium periodate (0.051 g, 0.24 mmol) was added and the reaction was allowed to vigorously stir for an additional 2 hours. The reaction mixture was diluted with ethanol (10 mL), filtered and concentrated to dryness in vacuo. The resultant material dissolved in minimum ethanol, filtered thru a short pad of silica, and concentrated to dryness in vacuo to give 5-(N-tert-butoxycarbonyl-hydroxylamino)-5-benzyl-barbituric acid as a white solid (70 mg, 100%). 5-(N-tert-butoxycarbonyl-hydroxylamino)-5-benzyl-barbituric acid (0.040 g, 0.11 mmol) was dissolved in a solution of ethanol (2.5 mL) to which concentrated hydrochloric acid was added (1 mL). The solution was left to stand overnight at 4° C., then diluted with ethanol (20 mL) and concentrated to dryness in vacuo (40° C.). The resultant material was triturated with ether and petroleum ether and filtered to give the HCl salt of 5 as a white solid (0.009 g, 29%). $^1$H NMR (400 MHz, MeOD-d$_4$) δ: 7.26 (m, 3H), 7.11 (m, 2H), 3.08 (2H). $^{13}$C NMR (100 MHz, MeOD-d$_4$) δ: 173.11, 150.78, 133.82, 130.97, 129.89, 129.09, 73.88, 41.65.

Example 6

Preparation of 5-(N-hydroxylamino)-5-(4-methoxybenzyl)-barbituric acid (6)

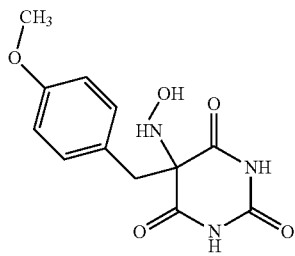 [SMILES: COc1ccc(CC2(NO)C(=O)NC(=O)NC2=O)cc1]

In a solution of 50% v/v aqueous ethanol (10 mL), 5-(4-methoxybenzyl)-barbituric acid (BA6) (0.050 g, 0.2 mmol), N-tert-butoxycarbonyl-hydroxylamine (0.032 g, 0.24 mmol), and potassium carbonate (0.050 g) were dissolved under sonication for 30 minutes at 25° C. To the solution, sodium periodate (0.051 g, 0.24 mmol) was added and the reaction was allowed to vigorously stir for an additional 2 hours. The reaction mixture was diluted with ethanol (10 mL), filtered and concentrated to dryness in vacuo. The resultant material dissolved in minimum ethanol, filtered thru a short pad of silica, and concentrated to dryness in vacuo to give 5-(N-tert-butoxycarbonyl-hydroxylamino)-5-(4-methoxybenzyl)-barbituric acid as a white solid (77 mg, 101%). 5-(N-tert-butoxycarbonyl-hydroxylamino)-5-(4-methoxybenzyl)-barbituric acid (0.035 g, 0.09 mmol) was dissolved in a solution of ethanol (2.5 mL) to which concentrated hydrochloric acid was added (1 mL). The solution was left to stand overnight at 4° C., then diluted with ethanol (20 mL) and concentrated to dryness in vacuo (40° C.). The resultant material was triturated with ether and petroleum ether and filtered to give the HCl salt of 6 as a white solid (0.012 g, 42%). $^1$H NMR (400 MHz, DMSO-d$_6$) δ: 11.35 (s, 2H), 6.92 (d, 2H, J=8.7 Hz), 6.82 (d, 2H, J=8.7 Hz), 3.70 (s, 3H), 2.92 (s, 2H). $^{13}$C NMR (100 MHz, DMSO-d$_6$) δ: 171.41, 158.50, 149.36, 130.62, 124.53, 113.90, 71.69, 55.00, 38.45.

Example 7

Preparation of 5-(N-hydroxylamino)-5-(4-chlorobenzyl)-barbituric acid (7)

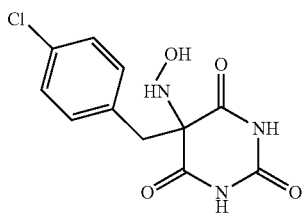

In a solution of 50% v/v aqueous ethanol (10 mL), 5-(4-chlorobenzyl)-barbituric acid (BA7) (0.050 g, 0.2 mmol), N-tert-butoxycarbonyl-hydroxylamine (0.032 g, 0.24 mmol), and potassium carbonate (0.050 g) were dissolved under sonication for 30 minutes at 25° C. To the solution, sodium periodate (0.051 g, 0.24 mmol) was added and the reaction was allowed to vigorously stir for an additional 2 hours. The reaction mixture was diluted with ethanol (10 mL), filtered and concentrated to dryness in vacuo. The resultant material dissolved in minimum ethanol, filtered thru a short pad of silica, and concentrated to dryness in vacuo to give 5-(N-tert-butoxycarbonyl-hydroxylamino)-5-(4-chlorobenzyl)-barbituric acid as a white solid (83 mg, 108%). 5-(N-tert-butoxycarbonyl-hydroxylamino)-5-(4-chlorobenzyl)-barbituric acid (0.037 g, 0.10 mmol) was dissolved in a solution of ethanol (2.5 mL) to which concentrated hydrochloric acid was added (1 mL). The solution was left to stand overnight at 4° C., then diluted with ethanol (20 mL) and concentrated to dryness in vacuo (40° C.). The resultant material was triturated with ether and petroleum ether and filtered to give 7 as a white solid (0.012 g, 42%). $^1$H NMR (400 MHz, DMSO-d$_6$) δ: 11.40 (s, 2H), 8.1 (s, 1H), 7.36 (d, 2H, J=8.4 Hz), 7.02 (d, 2H, J=8.4 Hz), 6.49 (br. s, 1H), 2.98 (s, 2H). $^{13}$C NMR (100 MHz, DMSO-d$_6$) δ: 171.37, 149.35, 132.20, 132.18, 131.42, 128.47, 71.37, 38.36.

Example 8

Preparation of 5-(N-hydroxylamino)-5-phenyl-barbituric acid (8)

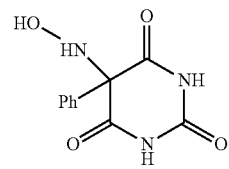

In a solution of 50% v/v aqueous ethanol (50 mL), sodium 5-phenyl-barbiturate (BA8) (2.262 g, 10 mmol), and N-tert-butoxycarbonyl-hydroxylamine (1.598 g, 12 mmol) were dissolved under sonication for 30 minutes at 25° C. To the solution, sodium periodate (2.567 g, 12 mmol) was added and the reaction was allowed to vigorously stir for an additional 2.5 hours. The reaction mixture was diluted with ethanol (100 mL), filtered and concentrated to dryness in vacuo. The resultant material dissolved in 50 mL of saturated ammonium chloride, extracted with diethyl ether (200 mL), washed with water and saturated sodium chloride, dried over magnesium sulfate, and concentrated to dryness in vacuo to give 5-(N-tert-butoxycarbonyl-hydroxylamino)-5-phenyl-barbituric acid as a white solid. The 5-(N-tert-butoxycarbonyl-hydroxylamino)-5-phenyl-barbituric acid was dissolved in a solution of ethanol (25 mL) to which concentrated hydrochloric acid (10 mL) was added. The solution was left to stand overnight at −20° C., then diluted with ethanol (100 mL) and concentrated to dryness in vacuo (40° C.). The resulting material was triturated with ether and petroleum ether and filtered to give the HCl salt of 8 as a white solid (1.1 g, 40% over two steps). $^1$H NMR (400 MHz, DMSO-d$_6$) δ: 11.76 (s, 2H), 8.60 (br. s, 2H), 7.38 (m, 5H). $^{13}$C NMR (100 MHz, DMSO-d$_6$) δ: 170.17, 149.62, 134.11, 129.34, 128.93, 126.53, 73.14.

Example 9

Preparation of 5-(N-hydroxylamino)-5-(2-propen-1-yl)-barbituric acid (9)

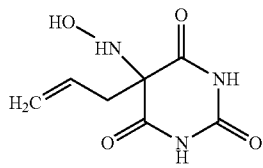

In a solution of 50% v/v aqueous ethanol (50 mL), sodium 5-(2-propen-1-yl)-barbiturate (BA9) (1.901 g, 10 mmol), and N-tert-butoxycarbonyl-hydroxylamine (1.598 g, 12 mmol) were dissolved under sonication for 30 minutes at 25° C. To the solution, sodium periodate (2.567 g, 12 mmol) was added and the reaction was allowed to vigorously stir for an additional 3 hours. The reaction mixture was diluted with ethanol (100 mL), filtered and concentrated to dryness in vacuo. The resultant material dissolved in 50 mL of saturated ammonium chloride, extracted with diethyl ether (200 mL), washed with water and saturated sodium chloride, dried over magnesium sulfate, and concentrated to dryness in vacuo to give 5-(N-tert-butoxycarbonyl-hydroxylamino)-5-(2-propen-1-yl)-barbituric acid as a white solid. The 5-(N-tert-butoxycarbonyl-hydroxylamino)-5-(2-propen-1-yl)-barbituric acid was dissolved in a solution of ethanol (25 mL) to which concentrated hydrochloric acid (10 mL) was added. The solution was left to stand overnight at −20° C., then diluted with ethanol (100 mL) and concentrated to dryness in vacuo (40° C.). The resultant material was dissolved in water (20 mL) and extracted with dichloromethane (150 mL). Sodium acetate (2.6 g) was added to the remaining aqueous solution and the mixture was extracted by ethyl acetate (200 mL). The organic layers were combined, dried over magnesium sulfate, and concentrated to dryness in vacuo. The resulting material was triturated with ether and petroleum ether and filtered to give 9 as a white solid (0.288 g, 14% over two steps). $^1$H NMR (400 MHz, DMSO-d$_6$) δ: 11.51 (s, 2H), 8.02 (d, 1H, J=2.4 Hz), 6.31 (d, 1H, J=2.4 Hz), 5.52 (m, 1H), 5.12 (dd, 1H, J=2.0, 8.3 Hz), 5.07 (dd, 1H, J=1.9, 16.8 Hz), 2.42 (d, 2H, J=7.5 Hz). $^{13}$C NMR (100 MHz, DMSO-d$_6$) δ: 171.56, 149.87, 129.63, 120.86, 69.95, 37.87.

Example 10

Preparation of 5-(N-hydroxylamino)-5-(2-methylpropyl)-barbituric acid (10)

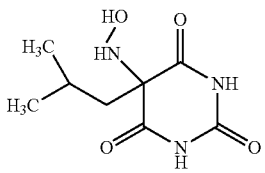

In a solution of 50% v/v aqueous ethanol (50 mL), sodium 5-(2-methylpropyl)-barbiturate (BA10) (2.152 g, 10 mmol), and N tert-butoxycarbonyl-hydroxylamine (1.598 g, 12 mmol) were dissolved at 25° C. To the solution, sodium periodate (2.567 g, 12 mmol) was added and the reaction was allowed to vigorously stir for an additional 2 hours. The reaction mixture was diluted with ethanol (100 mL), filtered and concentrated to dryness in vacuo. The resultant material dissolved in 50 mL of saturated ammonium chloride, extracted with diethyl ether (200 mL), washed with water and saturated sodium chloride, dried over magnesium sulfate, and concentrated to dryness in vacuo to give 5-(N-tert-butoxycarbonyl-hydroxylamino)-5-(2-methylpropyl)-barbituric acid as a white solid. The solid was dissolved in a solution of ethanol (25 mL) to which concentrated hydrochloric acid (6 mL) was added. The solution was left to stand for 1.5 days at −20° C., diluted with ethanol (100 mL), then concentrated to dryness in vacuo (40° C.). The resultant material was dissolved in water (20 mL) and washed with dichloromethane (150 mL). Sodium acetate (2.6 g) was added to the remaining aqueous solution and the mixture was extracted by ethyl acetate (200 mL) and the solution was washed with water and saturated sodium chloride, dried over magnesium sulfate, and concentrated to dryness in vacuo. The resulting material was triturated with ether and petroleum ether and filtered to give 10 as a white solid (0.847 g, 39% over two steps). $^1$H NMR (400 MHz, DMSO-d$_6$) δ: 11.54 (s, 2H), 7.99 (d, 1H, J=2.6 Hz), 6.21 (d, 1H, J=2.6 Hz), 1.62 (d, 2H, J=6.6 Hz), 1.49 (dq, 1H, J=6.6, 13 Hz), 0.79 (d, 6H, J=6.6 Hz). $^{13}$C NMR (100 MHz, DMSO-d$_6$) δ: 172.36, 149.99, 69.24, 41.52, 23.97, 23.28.

Example 11

Preparation of 5-(N-hydroxylamino)-5-(1-methylethyl)-barbituric acid (11)

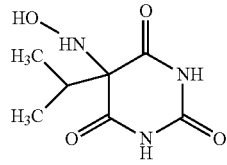

In a solution of 50% v/v aqueous ethanol (50 mL), sodium 5-(1-methylethyl)-barbiturate (BA11) (1.922 g, 10 mmol), and N-tert-butoxycarbonyl-hydroxylamine (1.598 g, 12 mmol) were dissolved under sonication for 30 minutes at 25° C. To the solution, sodium periodate (2.567 g, 12 mmol) was added and the reaction was allowed to vigorously stir for an additional 3 hours. The reaction mixture was diluted with ethanol (100 mL), filtered and concentrated to dryness in vacuo. The resultant material dissolved in 50 mL of saturated ammonium chloride, extracted with diethyl ether (200 mL), washed with water and saturated sodium chloride, dried over magnesium sulfate, and concentrated to dryness in vacuo to give a white solid, which was triturated with ether and petroleum ether at 0° C. and filtered to give 5-(N-tert-butoxycarbonyl-hydroxylamino)-5-(1-methylethyl)-barbituric acid as a white solid (1.243 g, 41%). The 5-(N-tert-butoxycarbonyl-hydroxylamino)-5-(1-methylethyl)-barbituric acid was dissolved in a solution of ethanol (25 mL) to which concentrated hydrochloric acid (10 mL) was added. The solution was left to stand overnight at 4° C., then diluted with ethanol (100 mL) and concentrated to dryness in vacuo (40° C.). The resultant material was triturated with ether and petroleum ether and filtered to give the HCl salt of 11 as a white solid (0.448 g, 54%). $^1$H NMR (400 MHz, DMSO-d$_6$) δ: 11.91 (s, 2H), 8.10 (br. s, 2H), 2.28 (t, 1H, J=6.9 Hz), 0.92 (d, 6H, J=6.8 Hz). $^{13}$C NMR (100 MHz, DMSO-d$_6$) δ: 168.69, 149.60, 73.52, 33.95, 17.02.

Example 12

Preparation of 5-(N-hydroxylamino)-5-(1-methylbutyl)-barbituric acid (12)

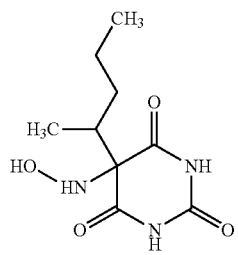

In a solution of 50% v/v aqueous ethanol (10 mL), sodium 5-(1-methylbutyl)-barbiturate (BA12) (0.440 g, 2 mmol), and N-tert-butoxycarbonyl-hydroxylamine (0.320 g, 2.4 mmol) were dissolved under sonication for 30 minutes at 25° C. To the solution, sodium periodate (0.513 g, 2.4 mmol) was added and the reaction was allowed to vigorously stir for an additional 4 hours. The reaction mixture was diluted with ethanol (25 mL), filtered and concentrated to dryness in vacuo. The resultant material dissolved in 10 mL of ammonium chloride, extracted with diethyl ether (200 mL), dried over magnesium sulfate, concentrated to dryness in vacuo to give a white solid, which was triturated with ether and petroleum ether, and the solution was left to stand for 2 days at −20° C. and filtered to give 5-(N-tert-butoxycarbonyl-hydroxylamino)-5-(1-methylbutyl)-barbituric acid as a white solid (0.164 g, 25%). 5-(N-tert-butoxycarbonyl-hydroxylamino)-5-(1-methylbutyl)-barbituric acid (0.100 g, 0.3 mmol) was dissolved in a solution of ethanol (2.5 mL) to which concentrated hydrochloric acid was added (1 mL). The solution was left to stand overnight at 4° C., then diluted with ethanol (20 mL) and concentrated to dryness in vacuo (40° C.). The resultant material was dissolved in ether, triturated with petroleum ether and filtered to give the HCl salt of 12 as a white solid (0.027 g, 40%). $^1$H NMR (400 MHz, DMSO-d$_6$) δ: 11.49 (d, 2H, J=3.6 Hz), 1.96 (m, 1H,), 1.39 (m, 2H), 1.07 (m, 2H), 0.89 (d, 3H, J=6.8 Hz), 0.81 (t, 3H, J=7.1 Hz). $^{13}$C NMR (100 MHz, DMSO-d$_6$) δ: 171.80, 149.99, 73.34, 38.37, 32.53, 19.85, 13.84, 13.59.

Example 13

Preparation of 5-(N-hydroxylamino)-5-(2-chlorobenzyl)-barbituric acid (14)

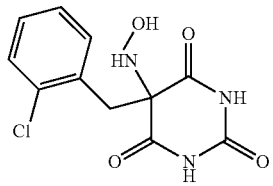 [SMILES: O=C1NC(=O)C(Cc2ccccc2Cl)(NO)C(=O)N1]

In a solution of 50% v/v aqueous ethanol (10 mL), 5-(2-chlorobenzyl)-barbituric acid (BA14) (0.050 g, 0.2 mmol), N-tert-butoxycarbonyl-hydroxylamine (0.032 g, 0.24 mmol), and potassium carbonate (0.050 g) were dissolved under sonication for 30 minutes at 25° C. To the solution, sodium periodate (0.051 g, 0.24 mmol) was added and the reaction was allowed to vigorously stir for an additional 2 hours. The reaction mixture was diluted with ethanol (10 mL), filtered and concentrated to dryness in vacuo. The resultant material dissolved in minimum ethanol, filtered thru a short pad of silica, and concentrated to dryness in vacuo to give 5-(N-tert-butoxycarbonyl-hydroxylamino)-5-(2-chlorobenzyl)-barbituric acid as a white solid (83 mg, 108%). 5-(N-tert-butoxycarbonyl-hydroxylamino)-5-(2-chlorobenzyl)-barbituric acid (0.043 g, 0.11 mmol) was dissolved in a solution of ethanol (2.5 mL) to which concentrated hydrochloric acid was added (1 mL). The solution was left to stand overnight at 4° C., then diluted with ethanol (20 mL) and concentrated to dryness in vacuo (40° C.). The resultant material was triturated with ether and petroleum ether and filtered to give 14 as a white solid (0.019 g, 61%). $^1$H NMR (400 MHz, DMSO-d$_6$) δ: 11.44 (s, 2H), 8.1 (s, 1H), 7.27 (m, 4H), 6.46 (br. s, 1H), 3.18 (s, 2H). $^{13}$C NMR (100 MHz, DMSO-d$_6$) δ: 170.79, 149.49, 133.93, 131.94, 131.43, 129.42, 129.17, 127.00, 70.34, 36.18.

Example 14

Preparation of 5-(N-hydroxylamino)-5-(2-thienylmethyl)-barbituric acid (16)

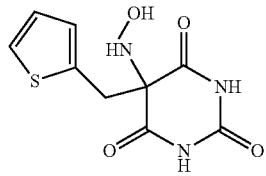 [SMILES: O=C1NC(=O)C(Cc2cccs2)(NO)C(=O)N1]

In a solution of 50% v/v aqueous ethanol (10 mL), 5-(2-thienylmethyl)-barbituric acid (BA16) (0.448 g, 2 mmol), and N-tert-butoxycarbonyl-hydroxylamine (0.320 g, 2.4 mmol) were dissolved under sonication for 30 minutes at 25° C. To the solution, sodium periodate (0.513 g, 2.4 mmol) was added and the reaction was allowed to vigorously stir for an additional 2 hours. The reaction mixture was diluted with ethanol (25 mL), filtered and concentrated to dryness in vacuo. The resultant material dissolved in 10 mL of ammonium chloride, extracted with diethyl ether (200 mL), dried over magnesium sulfate, concentrated to dryness in vacuo to give a white solid, which was triturated with ether and petroleum ether and filtered to give 5-(N-tert-butoxycarbonyl-hydroxylamino)-5-(2-thienylmethyl)-barbituric acid as an off-white solid (0.138 g, 19%). 5-(N-tert-butoxycarbonyl-hydroxylamino)-5-(2-thienylmethyl)-barbituric acid (0.052 g, 0.15 mmol) was dissolved in a solution of ethanol (2.5 mL) to which concentrated hydrochloric acid was added (1 mL). The solution was left to stand overnight at 4° C., then diluted with ethanol (20 mL) and concentrated to dryness in vacuo (40° C.). The resultant material was dissolved in ether, triturated with petroleum ether and filtered to give 16 as a white solid (0.026 g, 70%). $^1$H NMR (400 MHz, DMSO-$d_6$) δ: 11.45 (s, 2H), 8.13 (s, 1H), 7.39 (s, 1H), 6.94 (s, 1H), 6.73 (s, 1H), 6.53 (br. s, 1H), 3.21 (s, 2H). $^{13}$C NMR (100 MHz, DMSO-$d_6$) δ: 171.59, 149.56, 134.24, 127.73, 127.12, 126.02, 71.08, 32.95.

Example 15

Preparation of 5-(N-hydroxylamino)-5-methyl-barbituric acid (17)

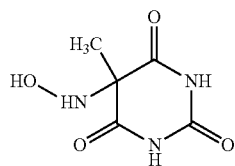

In a solution of 50% v/v aqueous ethanol (10 mL), sodium 5-methyl-barbiturate (BA17) (0.328 g, 2 mmol), and N-tert-butoxycarbonyl-hydroxylamine (0.320 g, 2.4 mmol) were dissolved under vigorous stirring for 30 minutes at 25° C. To the solution, sodium periodate (0.513 g, 2.4 mmol) was added, and the reaction was allowed to vigorously stir for an additional 2 hours. The reaction mixture was diluted with ethanol (25 mL), filtered and concentrated to dryness in vacuo. The resultant material dissolved in 10 mL of saturated ammonium chloride, extracted with diethylether (200 mL), dried over magnesium sulfate, and concentrated in vacuo to give a white solid, which was triturated with ether and petroleum ether and filtered to give 5-(N-tert-butoxycarbonyl-hydroxylamino)-5-methyl-barbituric acid as a white solid (0.243 g, 45%). 5-(N-tert-butoxycarbonyl-hydroxylamino)-5-methyl-barbituric acid (0.214 g, 0.8 mmol) was dissolved in a solution of ethanol (5 mL) to which concentrated hydrochloric acid was added (2 mL). The solution was left to stand overnight at 4° C., then diluted with ethanol (20 mL) and concentrated to dryness in vacuo (40° C.). The resultant material was triturated with ether and petroleum ether and filtered to give the HCl salt of 17 as a white solid (0.156 g, 45%). $^1$H NMR (400 MHz, DMSO-$d_6$) δ: 11.78 (s, 2H), 7.56 (br. s, 2H), 1.49 (s, 3H). $^{13}$C NMR (100 MHz, DMSO-$d_6$) δ: 169.32, 149.49, 65.72, 19.20.

Example 16

Preparation of 5-(N-hydroxylamino)-5-(1-methylpropyl)-barbituric acid (18)

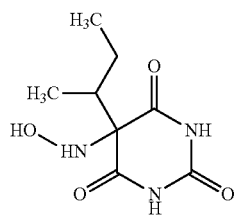

In a solution of 50% v/v aqueous ethanol (10 mL), sodium 5-(1-methylpropyl)-barbiturate (BA18) (0.412 g, 2 mmol), and N-tert-butoxycarbonyl-hydroxylamine (0.320 g, 2.4 mmol) were dissolved under sonication for 30 minutes at 25° C. To the solution, sodium periodate (0.513 g, 2.4 mmol) was added and the reaction was allowed to vigorously stir for an additional 2 hours. The reaction mixture was diluted with ethanol (25 mL), filtered and concentrated to dryness in vacuo. The resultant material dissolved in 10 mL of saturated ammonium chloride, extracted with diethyl ether (200 mL), dried over magnesium sulfate, and concentrated to dryness in vacuo to give a white solid, which was triturated with ether and petroleum ether and filtered to give 5-(N-tert-butoxycarbonyl-hydroxylamino)-5-(1-methylpropyl)-barbituric acid as a white solid (130 mg, 21%). 5-(N-tert-butoxycarbonyl-hydroxylamino)-5-(1-methylpropyl)-barbituric acid (0.101 g, 0.3 mmol) was dissolved in a solution of ethanol (2.5 mL) to which concentrated hydrochloric acid was added (1 mL). The solution was left to stand overnight at 4° C., then diluted with ethanol (20 mL) and concentrated to dryness in vacuo (40° C.). The resultant material was triturated with ether and petroleum ether and filtered to give the HCl salt of 18 as a white solid (0.026 g, 34%). $^1$H NMR (400 MHz, DMSO-$d_6$) δ: 11.51 (s, 2H), 1.86 (m, 1H), 1.49 (m, 1H), 0.97 (m, 1H), 0.88 (d, 3H, J=6.9 Hz), 0.81 (t, 3H, J=7.4 Hz), 0.80 (m, 1H). $^{13}$C NMR (100 MHz, DMSO-$d_6$) δ: 171.49, 149.97, 73.46, 40.47, 23.30, 13.06, 11.84.

5.2 Example 17

Nitroxyl Production, Rate and Half-Life Determined Via $^1$H NMR Protocol Using TXPTS The $^1$H NMR procedure used was based on an HPLC protocol developed by S. Bruce King and co-workers (Reisz et al., Org. Lett. 11:2719-2721 (2009), Reisz et al., J. Am. Chem. Soc. 133:11675-11685 (2011) and Guthrie et al., J. Org. Chem. 80:1338-1348 (2015).). According to this procedure, the amount of HNO released from a compound of the disclosure was determined by reacting the compound with a triarylphosphine and monitoring the resulting aza-ylide formation. Scheme 3 shows the conversion of a compound of formula (1) to its corresponding barbituric acid compound "BA-(1)" anion and HNO (trapped as one molecule of aza-ylide and one molecule of phosphine oxide.

Scheme 3

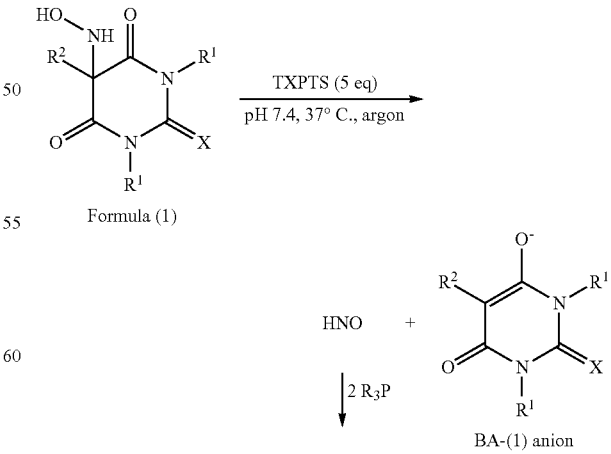

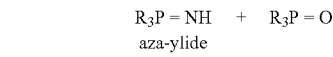

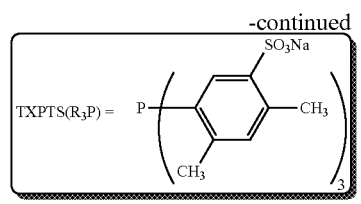

A procedure for determining the amount of HNO released from the compounds of the present disclosure is as follows. In the procedure that follows, the barbituric acid corresponding to a compound is referred to as "BA" followed by the compound number. For example, the barbituric acid corresponding to Compound 1 is referred to as BA1.

Compounds BA1-12, 14 and 16-18 are all known compounds, and were prepared according to literature procedures (Jursic, B. S.; Stevens, E. D. *Tet. Lett.*, 2003, 44, 2203-2210; Lofberg, C.; Grigg, R.; Keep, A.; Derrick, A.; Sridharan, V.; Kilner, *C. Chem. Commun.*, 2006, 5000-5002). Tris(4,6-dimethyl-3-sulfanatophenyl)phosphine trisodium salt (TXPTS) was of reagent grade and used without further purification. Synthetic TXPTS aza-ylide was obtained through the amidation of TXPTS using hydroxylamine O-sulfonic acid in water (Armstrong, A.; Jones, L. H.; Knight, J. D.; Kelsey, R. D. *Org. Lett.*, 2005, 7, 713-716). All other materials were of reagent grade and used without further purification.

All $^1$H NMR spectra were obtained in pH 7.4 solution containing 0.25 M phosphate buffer, 0.2 mM of the metal chelator diethylenetriaminepentaacetic acid (DTPA), and 10% $D_2O$ on a Bruker Avance 400 MHz FT-NMR spectrometer using a 1 second presaturation pulse to suppress the water signal. The data were processed with the academic version of ACDLabs NMR processor software: each free induction decay was Fourier transformed, phased, baseline corrected, and integral areas measured for the N-methyl groups of compounds 1-3 and BA1-BA3, the upfield alkyl groups of 4, 11, 12, and 16 and BA4, BA11, BA12, and BA16, and the downfield methyl group of TXPTS aza-ylide. The $^1$H NMR spectrum of the HNO derived TXPTS aza-ylide product matched that of synthetic TXPTS aza-ylide. The HNO yield from compounds 1-4, 11, 12, and 16 was determined from the final TXPTS aza-ylide yield.

To an argon-purged NMR solution (1.00 mL) containing TXPTS (3.3 mg, 5 mM) was added 1-4, 11, 12, and 18 (10 μL of 100 mM in methanol-$d_4$) to give 1 mM as the initial concentration of 1-4, 11, 12, and 18. The solution was briefly mixed, ca. 0.5 mL was transferred to an argon-purged NMR tube, and the sample was then either (1) externally incubated at 37° C. and $^1$H NMR spectra were collected at regular time intervals or (2) internally incubated at 43° C. and $^1$H NMR spectra were collected using a canned Bruker pulse sequence, zg2d, modified to include a 1 second presaturation pulse during the relaxation delay.

Table 2 shows the incubation of 1-4, 11, 12, and 18 in pH 7.4 phosphate buffer at 37° C. or 43° C. under argon with added TXPTS. Importantly, no other organic products arising from compounds 1-4, 11, 12, and 18 are observed.

TABLE 2

| Compound No.[a] | Compound Structure | $t_{1/2}$ (min) | $k(s^{-1})$[b] | HNO[c] |
|---|---|---|---|---|
| 1 | 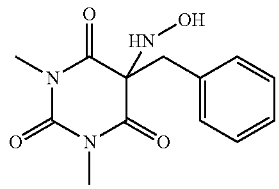 [SMILES: CN1C(=O)N(C)C(=O)C(Cc2ccccc2)(NO)C1=O] | 38 | $3.1 \times 10^{-4}$ | 99[d] |
| 2 | 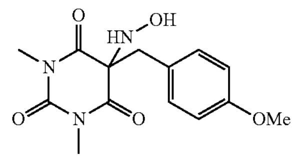 [SMILES: COc1ccc(CC2(NO)C(=O)N(C)C(=O)N(C)C2=O)cc1] | 79 | $1.5 \times 10^{-4}$ | 96[d] |
| 3 | 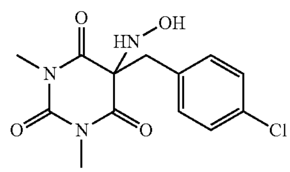 [SMILES: CN1C(=O)N(C)C(=O)C(Cc2ccc(Cl)cc2)(NO)C1=O] | 19 | $6.0 \times 10^{-4}$ | 92[d] |
| 4 | 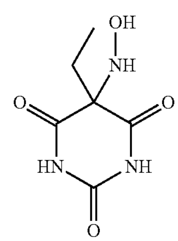 | 107 | $1.1 \times 10^{-4}$ | 97[d] |
| 11 | 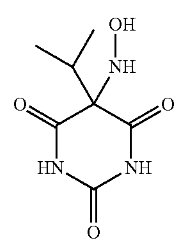 | 3746 | $3.1 \times 10^{-6}$ | 98 |
| 12 | 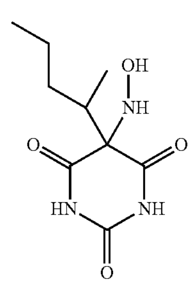 [SMILES: CCCC(C)C1(NO)C(=O)NC(=O)NC1=O] | 2311 | $5.0 \times 10^{-6}$ | 102 |

TABLE 2-continued

| Compound No.[a] | Compound Structure | $t_{1/2}$ (min) | $k(s^{-1})$[b] | HNO[c] |
|---|---|---|---|---|
| 18 | [structure: 5-sec-butyl-5-(N-hydroxyamino) barbituric acid] | 1973 | $5.9 \times 10^{-6}$ | 102 |

[a]Incubation conditions: Compound of the disclosure (1 mM) and TXPTS (5 mM) in 10% D$_2$O, pH 7.4 phosphate buffer (0.25M) with DTPA (0.2 mM) at 37° C. under argon; compounds 1-4 were incubated at 43° C.
[b]The rates are calculated best fits to a single exponential function of the integrated $^1$H NMR data for disappearance of the compound of the disclosure and appearance of its corresponding barbituric acid (BA) byproduct.
[c]HNO yields were determined from the final TXPTS aza-ylide yield.
[d]HNO yield determined at 43° C.

The complete decomposition of 1 to give BA1 and HNO-derived TXPTS aza-ylide under physiologically relevant conditions following the $^1$H NMR assay is shown in FIG. 1a. FIG. 1b shows the decompositions of 1, 2, 3, and 4.

5.3 Example 18

Rate and Half-Life Determined Via UV-Vis Protocol Using Glutathione

A procedure for determining the rate and half-life of the compounds of the present disclosure is as follows.

To an argon-purged pH 7.4, phosphate buffered saline solution (0.1 M, 4.00 mL) at 37° C. containing glutathione (ca. 120 µM) was added 1-5, 7, 9, and 11-16 (50 µL of 1 mM in methanol) to give ca. 12 µM as the initial concentration of 1-5, 7, 9, and 11-16. The solution was briefly mixed and UV-vis spectra were collected at regular time intervals until the reaction was complete as indicated by the appearance of the barbituric acid (BA) byproduct.

Table 3 shows the incubation of 1-5, 7, 9, and 11-16 in pH 7.4 phosphate buffered saline at 37° C. under argon with added glutathione.

TABLE 3

| Compound No.[a] | Compound Structure | $t_{1/2}$ (min) | $k(s^{-1})$[b] | $\lambda_{max}$ of BA (nm)[c] |
|---|---|---|---|---|
| 1 | [structure] | 77 | $1.5 \times 10^{-4}$ | 268 |
| 2 | [structure with OMe] | 145 | $8.0 \times 10^{-5}$ | 269 |
| 3 | [structure with Cl] | 46 | $2.5 \times 10^{-4}$ | 268 |
| 4 | [structure, ethyl] | 189 | $3.7 \times 10^{-5}$ | 268 |
| 5 | [structure, benzyl] | 92 | $1.3 \times 10^{-4}$ | 266 |
| 6 | [structure with OMe] | 132 | $8.8 \times 10^{-5}$ | 267 |
| 7 | [structure with Cl] | 71 | $1.6 \times 10^{-4}$ | 266 |
| 8 | [structure, Ph] | 14 | $8.2 \times 10^{-4}$ | 265 |
| 9 | [structure, allyl] | 90 | $1.3 \times 10^{-4}$ | 266 |

TABLE 3-continued

| Compound No.[a] | Compound Structure | $t_{1/2}$ (min) | $k(s^{-1})$[b] | $\lambda_{max}$ of BA (nm)[c] |
|---|---|---|---|---|
| 10 | 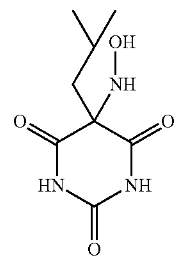 | 23 | $5.0 \times 10^{-4}$ | 269 |
| 11 | 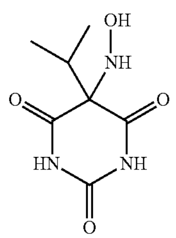 | N/A | N/A | N/A |
| 12 | 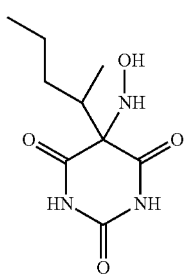 [SMILES: CCCC(C)C1(NO)C(=O)NC(=O)NC1=O] | N/A | N/A | N/A |
| 14 | 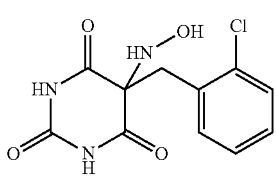 [SMILES: O=C1NC(=O)C(Cc2ccccc2Cl)(NO)C(=O)N1] | 41 | $2.9 \times 10^{-4}$ | 265 |
| 16 | 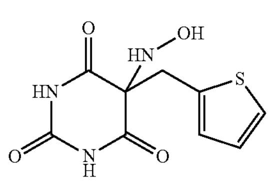 [SMILES: O=C1NC(=O)C(Cc2cccs2)(NO)C(=O)N1] | 40 | $2.9 \times 10^{-4}$ | 265 |
| 17 | 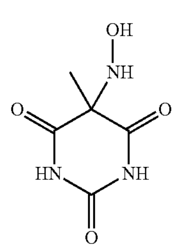 | 46 | $2.5 \times 10^{-4}$ | 266 |
| 18 | | N/A | N/A | N/A |

[a]Incubation conditions: Compound of the disclosure (12 μM) and glutathione (120 μM) in pH 7.4 phosphate buffered saline (0.1M) with DTPA (0.1 mM) at 37° C. under argon.
[b]The rates are calculated best fits to a single exponential function of the appearance of the corresponding barbituric acid (BA) byproduct.
[c]The maximum absorbance of the corresponding BA byproduct under the incubation conditions

5.4 Example 19

Graphical Titration Method for p$K_a$ Determination of BA Compounds

All pH measurements were made using a Fisher Scientific Accumet AB15 Basic pH meter and carried out under ambient conditions at 22-25° C. The AB15 glass electrode was calibrated before titration against Fisher Scientific pH 4.00, 7.00, and 10.00 buffer solutions. A stock solution of 200 mM sodium hydroxide was prepared in 50% v/v aqueous ethanol. To 10 mL of 50% v/v aqueous ethanol was added 0.20 mmol of BA byproduct and sonicated for 30 s. The solution was filtered through a cotton plug and titrated with 10 μL increments of the sodium hydroxide stock solution under constant stirring. The pH was recorded after each addition of base. The actual concentration of byproduct in the aqueous ethanol solution does not matter as long as the sodium hydroxide solution is ten times as concentrated to be able to titrate beyond the endpoint without adding a significant volume of solvent.

Table 4 shows the pKa determination for the BA compounds following the graphical titration method.

TABLE 4

| Compound[a] | R[1] | R[2] | p$K_a$ of BA[a] |
|---|---|---|---|
| 1 | Me | Bn | 4.2 |
| 2 | Me | 4-OMeBn | 4.3 |
| 3 | Me | 4-ClBn | 3.7 |
| 4 | H | Et | 4.1 |

[a]Determined by titration in 50% v/v aqueous ethanol.

The acidity of the benzyl barbituric acid, BA1, is comparable to benzoic acid. Like benzoic acid, the substituents on benzyl barbituric acid affect the acidity; that is, their acidities are increased by electron-withdrawing groups and decreased by electron-donating groups. This substituent effect has been demonstrated to obey Hammett's equation on a series of 5-substituted-benzyl-1,3-unsubstituted-barbituric acid derivatives (Tate, J. V.; Tinnerman II, W. N.; Jurevics, V.; Jeskey, H.; Biehl, E. R. *J. Heterocyclic Chem.* 1986, 23, 9-11.)

As such, the rate of decomposition of 1, 2 and 3 correlate with the pKa values of their respective BA byproducts. As the stability of the resultant carbanion increases, so too does the rate of HNO evolution. The pKa of the resultant byproducts, BA1-BA3, also affects the pKa of the corresponding HABA donors as well (FIG. 2a), where the sharp increases in observed rate reflect rapid BA formation as a result of HABA deprotonation.

5.5 Example 20

UV-Vis Method for $pK_a$ Determination of Compound 4

A 1 mM solution of compound 4 is prepared in acetonitrile. To a cuvette containing 3.0 mL of 0.10 M phosphate buffer of the desired pH at 25° C. is added 50 μL of the compound 4 solution. The solution is mixed quickly by rapidly drawing up and dispensing the solution with a pipette. Absorbance spectra are collected immediately after the solution has mixed and settled.

As shown in FIG. 2b, the ring nitrogen proton of 4 is mildly acidic. With a measured pKa of ca. 7.4, the pKa of 4 as a whole is more acidic than compounds 1-3. The relatively slower decomposition of 4 is presumably due to slow tautomerization of the HORN-BA-4 proton to the ring nitrogen anion, since the difference in acidity of these two positions are expected to be ca. 3-4 pKa units, based on the pKa values of compounds 1-3. FIG. 2c shows the initial spectra of 4 in a variety of phosphate buffers from pH 5.0 to pH 9.5. As the pH of the buffer increases, a new starting absorbance at 242 nm is observed, which is consistent with other mono-anion 5,5-disubstituted barbituric acids. For example, the λmax of the mono-anion of 5,5-diethylbarbituric acid, barbital, is 238 nm (Meusel, M.; Ambrożak, A.; Hecker, T.; Gütschow, M. *J. Org. Chem.* 2002, 68, 4684-4692). Also, the expected byproduct of HNO release, BA4 anion, is not observed in the initial spectra of 4 in any of the buffers, and therefore, does not contribute to the absorbance of 4 anion in this UV-vis spectral analysis.

It will be apparent to those in the art that specific embodiments of the disclosed subject matter may be directed to one or more of the above- and below-indicated embodiments While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:

1. A compound of formula (1):

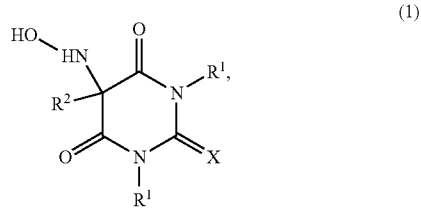

(1)

or a pharmaceutically acceptable salt thereof, wherein:
each $R^1$ is independently H or $(C_1)$alkyl;

$R^2$ is $(C_1-C_6)$alkyl substituted with a substituent selected from the group consisting of $(C_6-C_{14})$aryl, $(C_3-C_6)$cycloalkyl, $(C_5-C_7)$heterocycloalkyl, (5- or 6-membered)heteroaryl and (9- or 10-membered) heteroaryl, wherein said aryl, cycloalkyl, heterocycloalkyl and heteroaryl are unsubstituted or substituted with 1, 2, 3, 4 or 5 substituents selected from $R^4$ and said alkyl is unsubstituted or substituted with 1, 2 or 3 substituents selected from $R^6$;

X is O, $NR^7$ or S;

each $R^4$ is independently selected from the group consisting of halo, —OH, —$NH_2$, —C≡N, —$NO_2$, —SH, =O, =S, =N—$(C_1-C_4)$alkyl, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_6-C_{14})$aryl, $(C_3-C_6)$cycloalkyl, (5- or 6-membered)heteroaryl, $(C_5-C_7)$heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NR'R", —SR', —S(O)R', —S(O)OR', and —OR', wherein R' and R" are independently selected from $(C_1-C_6)$alkyl, $(C_2-C_6)$alkenyl, $(C_2-C_6)$alkynyl, $(C_6-C_{14})$aryl, $(C_3-C_6)$cycloalkyl, (5- or 6-membered)heteroaryl and $(C_5-C_7)$heterocycloalkyl;

each $R^6$ is independently selected from the group consisting of halo and $(C_1-C_6)$alkyl; and $R^7$ is H or $(C_1-C_6)$alkyl.

2. The compound of claim 1, wherein X is O or S.

3. The compound of claim 1, wherein at least one of $R^1$ is H.

4. The compound of claim 1, wherein at least one of $R^1$ is $(C_1)$alkyl.

5. The compound of claim 1, wherein each $R^1$ is $(C_1)$alkyl.

6. The compound of claim 1, wherein X is O.

7. The compound of claim 1, wherein X is S.

8. The compound of claim 1, wherein X is NH.

9. The compound of claim 1, wherein said compound has formula (1a):

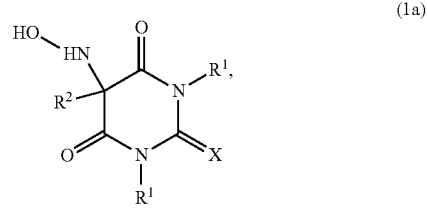

(1a)

or a pharmaceutically acceptable salt thereof, wherein:
$R^2$ is $(C_1-C_6)$alkyl substituted with $(C_6-C_{14})$aryl, wherein said aryl is unsubstituted or substituted with 1, 2, 3, 4 or 5 substituents selected from $R^4$ and said alkyl is unsubstituted or substituted with 1, 2 or 3 substituents selected from $R^6$.

10. The compound of claim 9, wherein $R^2$ is $(C_1)$alkyl substituted with $(C_6-C_{14})$aryl, wherein said aryl is unsubstituted or substituted with 1, 2, 3, 4 or 5 substituents selected from $R^4$.

11. The compound of claim 9, wherein said aryl is phenyl.

12. The compound of claim 9, wherein $R^4$ is $(C_1-C_6)$alkyl, —OH, $(C_1-C_3)$alkoxy, —S(O)O$(C_1-C_6)$alkyl or halo.

13. The compound of claim 1, wherein said compound has formula (1a-1):

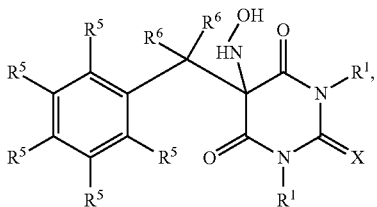

(1a-1)

or a pharmaceutically acceptable salt thereof, wherein:
each $R^1$ is $(C_1)$alkyl;
each $R^5$ is independently selected from the group consisting of H, halo, —OH, —NH$_2$, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_5$-C$_7$)heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from (C$_1$-C$_6$) alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_5$-C$_7$)heterocycloalkyl; and
each $R^6$ is independently selected from the group consisting of H, halo and (C$_1$-C$_6$)alkyl.

14. The compound of claim 13, wherein one or more of $R^5$ is selected from the group consisting of H, —OH, (C$_1$-C$_3$)alkoxy, S(O)O(C$_1$-C$_6$)alkyl and halo.

15. The compound of claim 13, wherein one or more of $R^5$ is methoxy.

16. The compound of claim 13, wherein one or more of $R^5$ is Cl.

17. The compound of claim 13, wherein at least one of $R^6$ is H.

18. The compound of claim 13, wherein at least one of $R^6$ is halo.

19. The compound of claim 13, wherein at least one of $R^6$ is methyl.

20. The compound of claim 13 wherein X is O.
21. The compound of claim 13, wherein X is S.
22. The compound of claim 13, wherein X is NH.
23. The compound of claim 1, wherein said compound has formula (1a-2):

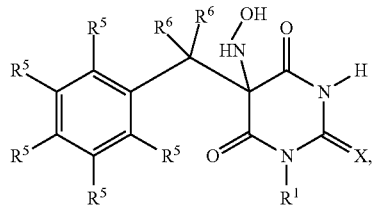

(1a-2)

or a pharmaceutically acceptable salt thereof, wherein:
$R^1$ is $(C_1)$alkyl;
each $R^5$ is independently selected from the group consisting of H, halo, —OH, —NH$_2$, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_5$-C$_7$)heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from (C$_1$-C$_6$) alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_5$-C$_7$)heterocycloalkyl; and
each $R^6$ is independently selected from the group consisting of H, halo and (C$_1$-C$_6$)alkyl.

24. The compound of claim 23, wherein one or more of $R^5$ is selected from the group consisting of H, —OH, (C$_1$-C$_3$)alkoxy, S(O)O(C$_1$-C$_6$)alkyl and halo.

25. The compound of claim 23, wherein one or more of $R^5$ is methoxy.

26. The compound of claim 23, wherein one or more of $R^5$ is Cl.

27. The compound of claim 23, wherein at least one of $R^6$ is H.

28. The compound of claim 23, wherein at least one of $R^6$ is halo.

29. The compound of claim 23, wherein at least one of $R^6$ is methyl.

30. The compound of claim 23, wherein X is O.
31. The compound of claim 23, wherein X is S.
32. The compound of claim 23, wherein X is NH.
33. The compound of claim 1, wherein said compound has formula (1b):

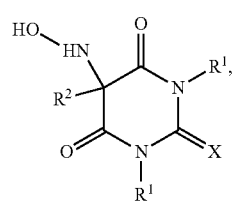

(1b)

or a pharmaceutically acceptable salt thereof, wherein:
each $R^1$ is independently H or $(C_1)$alkyl;
$R^2$ is (C$_1$-C$_6$)alkyl substituted with (C$_3$-C$_6$)cycloalkyl, wherein said heterocycloalkyl is unsubstituted or substituted with 1, 2 or 3 substituents selected from $R^4$ and said alkyl is unsubstituted or substituted with 1, 2 or 3 substituents selected from $R^6$;
each $R^4$ is independently selected from the group consisting of halo, —OH, —NH$_2$, —C≡N, —NO$_2$, —SH, =O, =S, =N—(C$_1$-C$_4$)alkyl, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, (C$_6$-C$_{14}$)aryl, (C$_3$-C$_6$)cycloalkyl, (5- or 6-membered)heteroaryl, (C$_5$-C$_7$)heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NR'R", —SR', —S(O)R', —S(O)OR', and —OR', wherein R' and R" are independently selected from (C$_1$-C$_6$)alkyl, (C$_2$-C$_6$)alkenyl, (C$_2$-C$_6$)alkynyl, (C$_6$-C$_{14}$)aryl, (C$_3$-C$_6$)cycloalkyl, (5- or 6-membered)heteroaryl and (C$_5$-C$_7$) heterocycloalkyl; and each R⁶ is independently selected from the group consisting of halo and $(C_1\text{-}C_6)$alkyl.

34. The compound of claim 33, wherein $R^2$ is $(C_1)$alkyl substituted with $(C_3\text{-}C_6)$cycloalkyl.

35. The compound of claim 33, wherein said $(C_3\text{-}C_6)$cycloalkyl is cyclohexyl.

36. The compound of claim 1, wherein said compound has formula (1c):

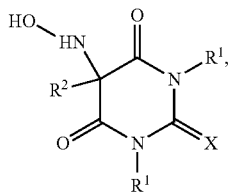

(1c)

or a pharmaceutically acceptable salt thereof, wherein:
$R^2$ is $(C_1\text{-}C_6)$alkyl substituted with $(C_5\text{-}C_7)$heterocycloalkyl, wherein said heterocycloalkyl is unsubstituted or substituted with 1, 2, 3, 4 or 5 substituents selected from $R^4$ and said alkyl is unsubstituted or substituted with 1, 2 or 3 substituents selected from $R^6$;

each $R^4$ is independently selected from the group consisting of halo, —OH, —NH₂, —C≡N, —NO₂, —SH, =O, =S, =N—$(C_1\text{-}C_4)$alkyl, $(C_1\text{-}C_6)$alkyl, $(C_2\text{-}C_6)$alkenyl, $(C_2\text{-}C_6)$alkynyl, $(C_1\text{-}C_6)$alkoxy, $(C_2\text{-}C_6)$alkenyloxy, $(C_2\text{-}C_6)$alkynyloxy, $(C_6\text{-}C_{14})$aryl, $(C_3\text{-}C_6)$cycloalkyl, (5- or 6-membered)heteroaryl, $(C_5\text{-}C_7)$heterocycloalkyl, —C(O)H, —C(O)NH₂, —C(O)OH, —NH—C(O)—NH₂, —NH—C(S)—NH₂, —SC≡N, —SO₂NH₂, —COR', —C(O)OR', C(O)NHR', —C(O)NR'R", —NR'R", —SR', —S(O)R', —S(O)OR', and —OR', wherein R' and R" are independently selected from $(C_1\text{-}C_6)$alkyl, $(C_2\text{-}C_6)$alkenyl, $(C_2\text{-}C_6)$alkynyl, $(C_6\text{-}C_{14})$aryl, $(C_3\text{-}C_6)$cycloalkyl, (5- or 6-membered)heteroaryl and $(C_5\text{-}C_7)$ heterocycloalkyl; and each R⁶ is independently selected from the group consisting of halo and $(C_1\text{-}C_6)$alkyl.

37. The compound of claim 36, wherein $R^2$ is $(C_1)$alkyl substituted with $(C_5\text{-}C_7)$heterocycloalkyl.

38. The compound of claim 1, wherein said compound has formula (1d):

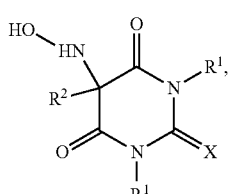

(1d)

or a pharmaceutically acceptable salt thereof, wherein:
$R^2$ is $(C_1\text{-}C_6)$alkyl substituted with (5- or 6-membered) heteroaryl or (9- or 10-membered)heteroaryl, wherein said heteroaryl is unsubstituted or substituted with 1, 2, 3, 4 or 5 substituents selected from $R^4$ and said alkyl is unsubstituted or substituted with 1, 2 or 3 substituents selected from $R^6$;

each $R^4$ is independently selected from the group consisting of halo, —OH, —NH₂, —C≡N, —NO₂, —SH, =O, =S, =N—$(C_1\text{-}C_4)$alkyl, $(C_1\text{-}C_6)$alkyl, $(C_2\text{-}C_6)$alkenyl, $(C_2\text{-}C_6)$alkynyl, $(C_1\text{-}C_6)$alkoxy, $(C_2\text{-}C_6)$alkenyloxy, $(C_2\text{-}C_6)$alkynyloxy, $(C_6\text{-}C_{14})$aryl, $(C_3\text{-}C_6)$cycloalkyl, (5- or 6-membered)heteroaryl, $(C_5\text{-}C_7)$heterocycloalkyl, —C(O)H, —C(O)NH₂, —C(O)OH, —NH—C(O)—NH₂, —NH—C(S)—NH₂, —SC≡N, —SO₂NH₂, —COR', —C(O)OR', C(O)NHR', —C(O)NR'R", —NHR', —NR'R", —SR', —S(O)R', —S(O)OR', and —OR', wherein R' and R" are independently selected from $(C_1\text{-}C_6)$alkyl, $(C_2\text{-}C_6)$alkenyl, $(C_2\text{-}C_6)$alkynyl, $(C_6\text{-}C_{14})$aryl, $(C_3\text{-}C_6)$cycloalkyl, (5- or 6-membered)heteroaryl and $(C_5\text{-}C_7)$heterocycloalkyl; and each R⁶ is independently selected from the group consisting of halo and $(C_1\text{-}C_6)$alkyl.

39. The compound of claim 38, wherein $R^2$ is $(C_1)$alkyl substituted with (5- or 6-membered)heteroaryl.

40. The compound of claim 38, wherein said heteroaryl is selected from the group consisting of furyl, thienyl, pyridyl, pyridazinyl, pyrimidyl, pyrazinyl, 1,3,5-triazinyl, thiophenyl, and benzo[d][1,3]dioxolyl.

41. The compound of claim 1 having the formula:

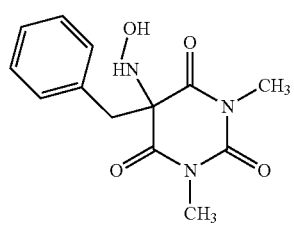

1 or a pharmaceutically acceptable salt thereof.

42. The compound of claim 1 having the formula:

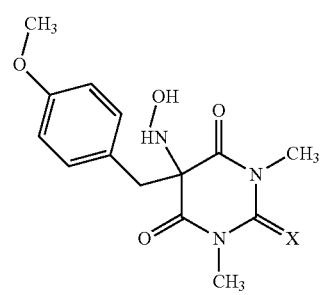

2 or a pharmaceutically acceptable salt thereof.

43. The compound of claim 1 having the formula:

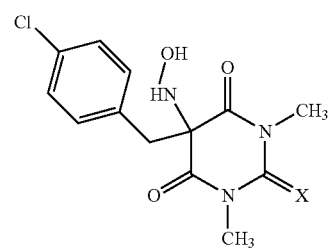

3 or a pharmaceutically acceptable salt thereof.

44. A compound of formula (2):

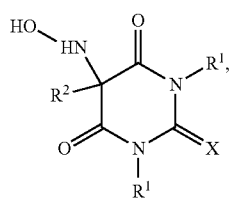

or a pharmaceutically acceptable salt thereof, wherein:
each $R^1$ is independently H or $(C_1)$alkyl;
$R^2$ is selected from the group consisting of a branched $C_3$-$C_6$ alkyl, a branched $C_3$-$C_6$ alkenyl, and a branched $C_3$-$C_6$ alkoxy, wherein said alkyl, alkenyl, and alkoxy are unsubstituted or substituted with 1, 2 or 3 substituents selected from $R^4$;
X is O, $NR^7$ or S;
each $R^4$ is independently selected from the group consisting of halo, —OH, —NH$_2$, —C≡N, —NO$_2$, —SH, =O, =S, =N—$(C_1$-$C_4)$alkyl, $(C_1$-$C_6)$alkyl, $(C_2$-$C_6)$alkenyl, $(C_2$-$C_6)$alkynyl, $(C_1$-$C_6)$alkoxy, $(C_2$-$C_6)$alkenyloxy, $(C_2$-$C_6)$alkynyloxy, $(C_6$-$C_{14})$aryl, $(C_3$-$C_6)$cycloalkyl, (5- or 6-membered)heteroaryl, $(C_5$-$C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from $(C_1$-$C_6)$alkyl, $(C_2$-$C_6)$alkenyl, $(C_2$-$C_6)$alkynyl, $(C_6$-$C_{14})$aryl, $(C_3$-$C_6)$cycloalkyl, (5- or 6-membered)heteroaryl and $(C_5$-$C_7)$heterocycloalkyl; and
$R^7$ is H or $(C_1$-$C_6)$alkyl.

45. The compound of claim 44, wherein X is O or S.
46. The compound of claim 44, wherein at least one of $R^1$ is H.
47. The compound of claim 44, wherein at least one of $R^1$ is $(C_1)$alkyl.
48. The compound of claim 44, wherein each $R^1$ is methyl.
49. The compound of claim 44, wherein $R^2$ is selected from the group consisting of iso-propyl, methylpropyl, sec-butyl, iso-butyl, tert-butyl, methylbutyl, iso-pentyl, methylpentyl, ethylbutyl, dimethylbutyl, and iso-propylpropyl.
50. The compound of claim 44, wherein X is O.
51. The compound of claim 44, wherein X is S.
52. The compound of claim 44, wherein X is NH.
53. A compound of formula (3):

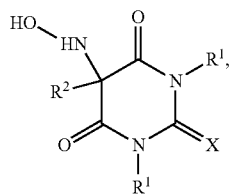

or a pharmaceutically acceptable salt thereof, wherein:
each $R^1$ is H;
$R^2$ is selected from the group consisting of $(C_1$-$C_6)$alkyl, $(C_2$-$C_6)$alkenyl, $(C_2$-$C_6)$alkynyl and $(C_1$-$C_6)$alkoxy,
wherein said alkyl, alkenyl, alkynyl and alkoxy are unsubstituted or substituted with 1, 2 or 3 substituents selected from $R^4$;
X is O, $NR^7$ or S;
each $R^4$ is independently selected from the group consisting of halo, —OH, —CH$_2$OH, —NH$_2$, —C≡N, —NO$_2$, —SH, =O, =S, =N—$(C_1$-$C_4)$alkyl, $(C_1$-$C_6)$alkyl, $(C_2$-$C_6)$alkenyl, $(C_2$-$C_6)$alkynyl, $(C_1$-$C_6)$alkoxy, $(C_2$-$C_6)$alkenyloxy, $(C_2$-$C_6)$alkynyloxy, $(C_6$-$C_{14})$aryl, $(C_3$-$C_6)$cycloalkyl, (5- or 6-membered)heteroaryl, $(C_5$-$C_7)$heterocycloalkyl, —C(O)H, —C(O)NH$_2$, —C(O)OH, —NH—C(O)—NH$_2$, —NH—C(NH)—NH$_2$, —NH—C(S)—NH$_2$, —SC≡N, —SO$_2$NH$_2$, —COR', —C(O)OR', C(O)NHR', —C(O)NR'R", —NR'R", —SR', —S(O)R', —S(O)OR', and —OR', wherein R' and R" are independently selected from $(C_1$-$C_6)$alkyl, $(C_2$-$C_6)$alkenyl, $(C_2$-$C_6)$alkynyl, $(C_6$-$C_{14})$aryl, $(C_3$-$C_6)$cycloalkyl, (5- or 6-membered)heteroaryl and $(C_5$-$C_7)$heterocycloalkyl; and
$R^7$ is H or $(C_1$-$C_6)$alkyl.

54. The compound of claim 53, wherein X is O or S.
55. The compound of claim 53, wherein $R^2$ is $(C_1$-$C_6)$ alkyl, wherein said alkyl is unsubstituted or substituted with 1, 2 or 3 substituents selected from $R^4$.
56. The compound of claim 53, wherein $R^2$ is methyl, ethyl, propylene, iso-propyl, methylbutyl, methylpropyl, iso-pentyl or trifluoroethyl.
57. The compound of claim 53, wherein $R^2$ is selected from the group consisting of a branched $(C_3$-$C_6)$alkyl, branched $(C_3$-$C_6)$alkenyl, and branched $(C_3$-$C_6)$alkoxy, wherein said alkyl, alkenyl, and alkoxy are unsubstituted or substituted with 1, 2 or 3 substituents selected from $R^4$.
58. The compound of claim 53, wherein X is O.
59. The compound of claim 53, wherein X is S.
60. The compound of claim 53, wherein X is NH.
61. The compound of claim 53, wherein said compound has formula (3a):

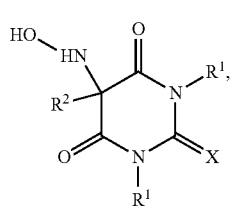

or a pharmaceutically acceptable salt thereof, wherein:
$R^2$ is $(C_1$-$C_4)$alkyl substituted with phenyl, wherein said phenyl is unsubstituted or substituted with 1, 2, 3, 4 or 5 substituents selected from $R^4$ and said alkyl is unsubstituted or substituted with 1, 2 or 3 substituents selected from $R^6$;
each $R^4$ is independently selected from the group consisting of halo, —OH, —NH$_2$, —C≡N, —NO$_2$, —SH, =O, =S, =N—$(C_1$-$C_4)$alkyl, $(C_1$-$C_6)$alkyl, $(C_2$-$C_6)$alkenyl, $(C_2$-$C_6)$alkynyl, $(C_1$-$C_6)$alkoxy, $(C_2$-$C_6)$alkenyloxy, $(C_2$-$C_6)$alkynyloxy, $(C_6$-$C_{14})$aryl, $(C_3$-$C_6)$cycloalkyl, (5- or 6-membered)heteroaryl, $(C_5$-$C_7)$heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl; and each $R^6$ is independently selected from the group consisting of halo, —S(O)O($C_1$-$C_6$)alkyl and ($C_1$-$C_6$)alkyl.

62. The compound of claim 61, wherein $R^2$ is ($C_1$)alkyl substituted with phenyl.

63. The compound of claim 61, wherein $R^4$ is ($C_1$-$C_3$) alkoxy or halo.

64. The compound of claim 61, wherein X is O.

65. The compound of claim 61, wherein X is S.

66. The compound of claim 61, wherein X is NH.

67. The compound of claim 53, wherein said compound has formula (3a-1):

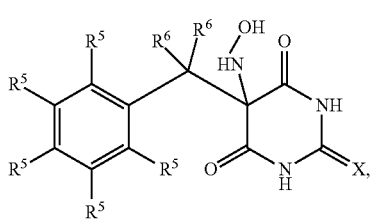

(3a-1)

or a pharmaceutically acceptable salt thereof, wherein:
each $R^5$ is selected from the group consisting of H, halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl; and each $R^6$ is independently selected from the group consisting of H, halo and ($C_1$-$C_6$)alkyl.

68. The compound of claim 67, wherein one or more of $R^5$ is selected from the group consisting of H, —OH, ($C_1$-$C_3$)alkoxy, —S(O)O($C_1$-$C_6$)alkyl and halo.

69. The compound of claim 67, wherein one or more of $R^5$ is methoxy.

70. The compound of claim 67, wherein one or more of $R^5$ is Cl.

71. The compound of claim 67, wherein at least one of $R^6$ is H.

72. The compound of claim 67, wherein at least one of $R^6$ is halo.

73. The compound of claim 67, wherein at least one of $R^6$ is methyl.

74. The compound of claim 67, wherein X is O.

75. The compound of claim 67, wherein X is S.

76. The compound of claim 67, wherein X is NH.

77. The compound of claim 53, wherein said compound has formula (3b):

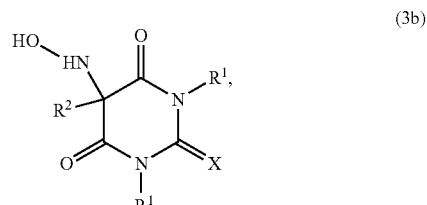

(3b)

or a pharmaceutically acceptable salt thereof, wherein:
$R^2$ is ($C_1$-$C_4$)alkyl substituted with ($C_3$-$C_6$)cycloalkyl, wherein said cycloalkyl is unsubstituted or substituted with 1, 2 or 3 substituents selected from $R^4$ and said alkyl is unsubstituted or substituted with 1, 2 or 3 substituents selected from $R^6$;

each $R^4$ is independently selected from the group consisting of halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$) heterocycloalkyl; and each $R^6$ is independently selected from the group consisting of halo and ($C_1$-$C_6$)alkyl.

78. The compound of claim 77, wherein $R^2$ is ($C_1$)alkyl substituted with ($C_3$-$C_6$)cycloalkyl.

79. The compound of claim 77, wherein said ($C_3$-$C_6$) cycloalkyl is cyclohexyl.

80. The compound of claim 77, wherein X is O.

81. The compound of claim 77, wherein X is S.

82. The compound of claim 77, wherein X is NH.

83. The compound of claim 53, wherein said compound has formula (3c):

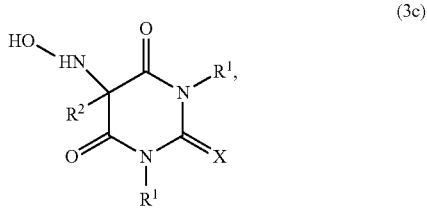

(3c)

or a pharmaceutically acceptable salt thereof, wherein:
$R^2$ is ($C_1$-$C_4$)alkyl substituted with ($C_5$-$C_7$)heterocycloalkyl, wherein said heterocycloalkyl is unsubstituted or substituted with 1, 2, 3, 4 or 5 substituents selected from $R^4$ and said alkyl is unsubstituted or substituted with 1, 2 or 3 substituents selected from $R^6$;

each $R^4$ is independently selected from the group consisting of halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NHR', —NR' R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl; and
each R$^6$ is independently selected from the group consisting of halo and ($C_1$-$C_6$)alkyl.

84. The compound of claim 83, wherein R$^2$ is ($C_1$)alkyl substituted with ($C_5$-$C_7$)heterocycloalkyl.

85. The compound of claim 83, wherein said hetercycloalkyl is a ($C_6$)heterocycloalkyl selected from the group consisting of piperidinyl, piperazinyl, tetrahydro-oxazinyl, tetrahydropyran, dioxane, morpholine and thiomorpholine.

86. The compound of claim 83, wherein X is O.

87. The compound of claim 83, wherein X is S.

88. The compound of claim 83, wherein X is NH.

89. The compound of claim 53, wherein said compound has formula (3d):

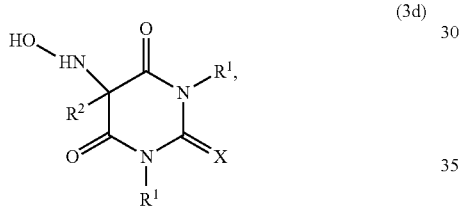

(3d)

or a pharmaceutically acceptable salt thereof, wherein:
R$^2$ is ($C_1$-$C_4$)alkyl substituted with (5- or 6-membered) heteroaryl or (9- or 10-membered)heteroaryl, wherein said heteroaryl is unsubstituted or substituted with 1, 2, 3, 4 or 5 substituents selected from R$^4$ and said alkyl is unsubstituted or substituted with 1, 2 or 3 substituents selected from R$^6$;
each R$^4$ is independently selected from the group consisting of halo, —OH, —CH$_2$OH, —NH$_2$, —C≡N, —NO$_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered) heteroaryl, ($C_5$-$C_7$)heterocycloalkyl, —C(O)H, —C(O)NH$_2$, —C(O)OH, —NH—C(O)—NH$_2$, —NH—C(S)—NH$_2$, —SC≡N, —SO$_2$NH$_2$, —COR', —C(O)OR', C(O)NHR', —C(O)NR'R", —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl; and
each R$^6$ is independently selected from the group consisting of halo and ($C_1$-$C_6$)alkyl.

90. The compound of claim 89, wherein R$^2$ is ($C_1$)alkyl substituted with (5- or 6-membered)heteroaryl.

91. The compound of claim 89, wherein said heteroaryl is selected from the group consisting of furyl, thienyl, imidazolyl, pyridyl, pyridazinyl, pyrimidyl, pyrazinyl, 1,3,5-triazinyl, thiophenyl, 1H-indolyl, 3H-indolyl and benzo[d][1,3]dioxolyl.

92. The compound of claim 89, wherein X is O.

93. The compound of claim 89, wherein X is S.

94. The compound of claim 89, wherein X is NH.

95. The compound of claim 53 having the formula:

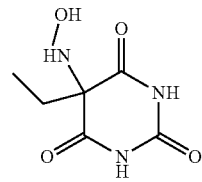

4 or a pharmaceutically acceptable salt thereof.

96. The compound of claim 53 having the formula:

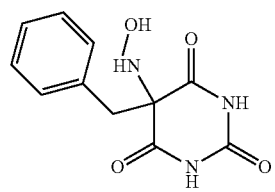

5 or a pharmaceutically acceptable salt thereof.

97. The compound of claim 53 having the formula:

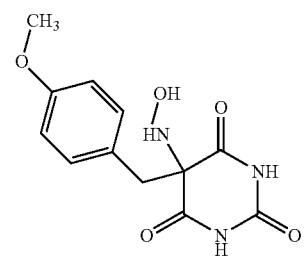

6 or a pharmaceutically acceptable salt thereof.

98. The compound of claim 53 having the formula:
s or a pharmaceutically acceptable salt thereof.

99. A compound of formula (4):

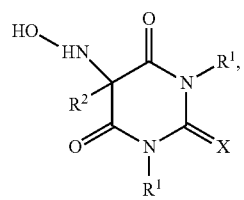

(4)

or a pharmaceutically acceptable salt thereof, wherein:
each R$^1$ is independently H or ($C_1$)alkyl;
R$^2$ is ($C_6$-$C_{10}$)aryl, ($C_3$-$C_6$)cycloalkyl, ($C_5$-$C_7$)heterocycloalkyl and (5- or 6-membered)heteroaryl, wherein said aryl, cycloalkyl, heterocycloalkyl and heteroaryl are unsubstituted or substituted with 1, 2, 3, 4 or 5 substituents selected from $R^4$;

X is O, $NR^7$ or S;

each $R^4$ is independently selected from the group consisting of halo, —OH, —$NH_2$, —C≡N, —$NO_2$, —SH, =O, =S, =N—($C_1$-$C_4$)alkyl, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, ($C_6$-$C_{14}$)aryl, ($C_3$-$C_6$)cycloalkyl, (5- or 6-membered)heteroaryl, ($C_5$-$C_7$)heterocycloalkyl, —C(O)H, —C(O)$NH_2$, —C(O)OH, —NH—C(O)—$NH_2$, —NH—C(S)—$NH_2$, —SC≡N, —$SO_2NH_2$, —COR', —C(O)OR', C(O)NHR', —C(O)NR'R", —NHR', —NR'R", —SR', —S(O)R', —S(O)OR', and —OR', wherein R' and R" are independently selected from ($C_1$-$C_6$)alkyl, ($C_2$-$C_6$)alkenyl, ($C_2$-$C_6$)alkynyl, ($C_6$-$C_{14}$)aryl, ($C_3$-$C_6$)cycloalkyl, (5- or 6-membered)heteroaryl and ($C_5$-$C_7$)heterocycloalkyl; and $R^7$ is H or ($C_1$-$C_6$)alkyl.

100. The compound of claim 99, wherein at least one of $R^1$ is H.

101. The compound of claim 99, wherein at least one of $R^1$ is ($C_1$)alkyl.

102. The compound of claim 99, wherein each $R^1$ is ($C_1$)alkyl.

103. The compound of claim 99, wherein X is O.

104. The compound of claim 99, wherein X is S.

105. The compound of claim 99, wherein X is NH.

106. The compound of claim 99, wherein said compound has formula (4a):

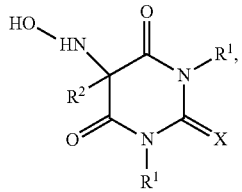

(4a)

or a pharmaceutically acceptable salt thereof, wherein:
$R^2$ is ($C_6$-$C_{10}$)aryl, wherein said aryl is unsubstituted or substituted with 1, 2, 3, 4 or 5 substituents selected from $R^4$.

107. The compound of claim 106, wherein:
$R^2$ is phenyl unsubstituted or substituted with 1, 2, 3, 4 or 5 substituents selected from $R^4$.

108. The compound of claim 107, wherein:
$R^2$ is unsubstituted phenyl.

109. The compound of claim 99, wherein said compound has formula (4b):

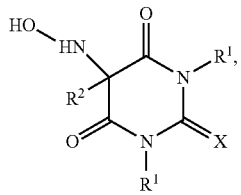

(4b)

or a pharmaceutically acceptable salt thereof, wherein:
$R^2$ is ($C_3$-$C_6$)cycloalkyl, wherein said cycloalkyl is unsubstituted or substituted with 1, 2, 3, 4 or 5 substituents selected from $R^4$.

110. The compound of claim 109, wherein $R^2$ is cyclohexyl.

111. The compound of claim 99, wherein said compound has formula (4c):

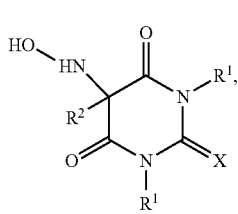

(4c)

or a pharmaceutically acceptable salt thereof, wherein:
$R^2$ is ($C_5$-$C_7$)heterocycloalkyl, wherein said heterocycloalkyl is unsubstituted or substituted with 1, 2, 3, 4 or 5 substituents selected from $R^4$.

112. The compound of claim 111, wherein $R^2$ is ($C_6$) heterocycloalkyl.

113. The compound of claim 99, wherein said compound has formula (4d):

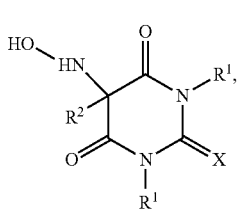

(4d)

or a pharmaceutically acceptable salt thereof, wherein:
$R^2$ is (5- or 6-membered)heteroaryl, wherein said heteroaryl is unsubstituted or substituted with 1, 2, 3, 4 or 5 substituents selected from $R^4$.

114. A compound of formula (5):

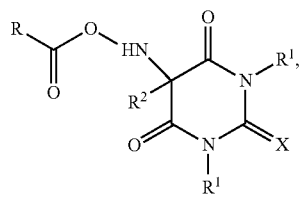

(5)

or a pharmaceutically acceptable salt thereof, wherein:
$R^1$, $R^2$ and X are as defined in claim 1; and
R is hydrogen, —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —$NH_2$, —NH—($C_1$-$C_4$)alkyl, or —N(($C_1$-$C_4$)alkyl)$_2$, wherein said —($C_1$-$C_6$)alkyl, —($C_2$-$C_4$)alkenyl, phenyl, benzyl, cyclopentyl, cyclohexyl, —($C_5$-$C_7$)heterocycloalkyl, benzyloxy, —O—($C_1$-$C_6$)alkyl, —NH—($C_1$-$C_4$)alkyl, or —N(($C_1$-$C_4$)alkyl)$_2$ can be unsubstituted or substituted with 1, 2 or 3 substituents selected from halo, —($C_1$-$C_6$)alkyl, —($C_2$-$C_4$)alkenyl, —($C_2$-$C_3$)alkynyl, -(5- or 6-membered)heteroaryl, —O—($C_1$-$C_6$)alkyl, —S—($C_1$-$C_6$)alkyl, —C(halo)$_3$, —CH(halo)$_2$, —$CH_2$(halo), —CN, —$NO_2$, —$NH_2$, —NH—($C_1$-$C_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, or —S(O)$_2$(C$_1$-C$_4$)alkyl.

115. A compound of formula (5):

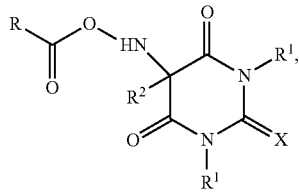

(5)

or a pharmaceutically acceptable salt thereof, wherein:
R$^1$, R$^2$ and X are as defined in claim 44; and
R is hydrogen, —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH$_2$, —NH—(C$_1$-C$_4$)alkyl, or —N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, or —S(O)$_2$(C$_1$-C$_4$)alkyl.

116. A compound of formula (5):

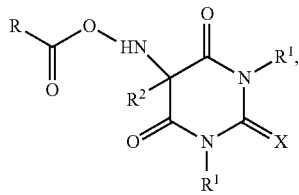

(5)

or a pharmaceutically acceptable salt thereof, wherein:
R$^1$, R$^2$ and X are as defined in claim 53; and
R is hydrogen, —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH$_2$, —NH—(C$_1$-C$_4$)alkyl, or —N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, or —S(O)$_2$(C$_1$-C$_4$)alkyl.

117. A compound of formula (5):

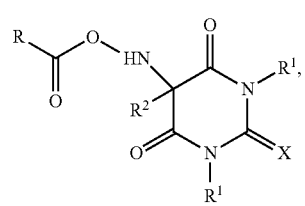

(5)

or a pharmaceutically acceptable salt thereof, wherein:
R$^1$, R$^2$ and X are as defined in claim 99; and
R is hydrogen, —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH$_2$, —NH—(C$_1$-C$_4$)alkyl, or —N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, —(C$_5$-C$_7$)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, or —S(O)$_2$(C$_1$-C$_4$)alkyl.

118. A compound selected from:
5-(N-hydroxylamino)-5-benzyl-N,N-dimethylbarbituric acid;
5-(N-hydroxylamino)-5-(4-methoxybenzyl)-N,N-dimethylbarbituric acid;
5-(N-hydroxylamino)-5-(4-chlorobenzyl)-N,N-dimethylbarbituric acid;
5-(N-hydroxylamino)-5-ethyl-barbituric acid;
5-(N-hydroxylamino)-5-benzyl-barbituric acid;
5-(N-hydroxylamino)-5-(4-methoxybenzyl)-barbituric acid;
5-(N-hydroxylamino)-5-(4-chlorobenzyl)-barbituric acid;
5-(N-hydroxylamino)-5-phenyl-barbituric acid;
5-(N-hydroxylamino)-5-(2-propen-1-yl)-barbituric acid;
5-(N-hydroxylamino)-5-(2-methylpropyl)-barbituric acid;
5-(N-hydroxylamino)-5-(1-methylethyl)-barbituric acid;
5-(N-hydroxylamino)-5-(1-methylbutyl)-barbituric acid;
5-(N-hydroxylamino)-5-phenyl-thiobarbituric acid;
5-(N-hydroxylamino)-5-(2-chlorobenzyl)-barbituric acid;
5-(N-hydroxylamino)-5-(2-furylmethyl)-barbituric acid;
5-(N-hydroxylamino)-5-(2-thienylmethyl)-barbituric acid;
5-(N-hydroxylamino)-5-methyl-barbituric acid;
5-(N-hydroxylamino)-5-(1-methylpropyl)-barbituric acid;
5-(hydroxylamino)-5-(3-methylbutyl) barbituric acid;
5-(hydroxyamino)-2-imino-5-phenyldihydropyrimidine-4,6(1H,5H)-dione;
5-(hydroxylamino)-5-(2,2,2-trifluoroethyl)barbituric acid;
5-(hydroxylamino)-5-(4-(methylsulfonyl)benzyl)barbituric acid
5-(hydroxylamino)-5-(benzo[d][1,3]dioxol-5-ylmethyl) barbituric acid;

5-(hydroxylamino)-5-(pyridin-4-ylmethyl)barbituric acid;

5-(hydroxylamino)-5-(3-ethyl-5-hydroxy-6-methylpyridin-4-ylmethyl)barbituric acid;

5-(hydroxylamino)-5-(3-hydroxy-5-(hydroxylmethyl)-2-methylpyridin-4-ylmethyl)barbituric acid;

5-(hydroxylamino)5-(2-(methylthio)ethyl)barbituric acid;

5-(hydroxyamino)-5-(4-hydroxybenzyl)barbituric acid;

5-((1H-indol-2-yl)methyl)-5-(hydroxyamino)barbituric acid;

2-(5-(hydroxyamino)-2,4,6-trioxohexahydropyrimidin-5-yl)acetic acid;

3-(5-(hydroxyamino)-2,4,6-trioxohexahydropyrimidin-5-yl)propanoic acid 2-(5-(hydroxyamino)-2,4,6-trioxohexahydropyrimidin-5-yl)acetamide;

3-(5-(hydroxyamino)-2,4,6-trioxohexahydropyrimidin-5-yl)propanamide;

5-((1H-imidazol-5-yl)methyl)-5-(hydroxyamino)barbituric acid;

5-(4-aminobutyl)-5-(hydroxyamino)barbituric acid;

1-(3-(5-(hydroxyamino)-2,4,6-trioxohexahydropyrimidin-5-yl)propyl)guanidine;

5-(hydroxylamino)5-(2-(methylthio)ethyl)barbituric acid;

5-(hydroxyamino)-5-(4-hydroxybenzyl)barbituric acid;

5-((1H-indol-2-yl)methyl)-5-(hydroxyamino)barbituric acid;

2-(5-(hydroxyamino)-2,4,6-trioxohexahydropyrimidin-5-yl)acetic acid;

3-(5-(hydroxyamino)-2,4,6-trioxohexahydropyrimidin-5-yl)propanoic acid 2-(5-(hydroxyamino)-2,4,6-trioxohexahydropyrimidin-5-yl)acetamide;

3-(5-(hydroxyamino)-2,4,6-trioxohexahydropyrimidin-5-yl)propanamide;

5-((1H-imidazol-5-yl)methyl)-5-(hydroxyamino)barbituric acid;

5-(4-aminobutyl)-5-(hydroxyamino)barbituric acid; and 1-(3-(5-(hydroxyamino)-2,4,6-trioxohexahydropyrimidin-5-yl)propyl)guanidine.

119. A pharmaceutical composition comprising the compound of and of claims 1, 44, 53, 99, 114, 115, 116 or 117 or 118 and at least one pharmaceutically acceptable excipient.

120. The pharmaceutical composition of claim 119, wherein said pharmaceutical composition is suitable for intravenous administration.

121. A method of treating a cardiovascular disease selected from the group consisting of coronary obstructions, coronary artery disease, angina, heart attack, myocardial infarction, high blood pressure, ischemic cardiomyopathy and infarction, pulmonary congestion, pulmonary edema, valvular heart disease, pericardial disease, circulatory congestive states, peripheral edema, ascites, ventricular hypertrophy, heart valve disease, heart failure, and cardiac hypertrophy comprising administering an effective amount of the compound of and of claims 1, 44, 53, 99, 114, 115, 116, 117 or 118 or the pharmaceutical composition of claim 119 to a patient in need thereof.

122. The method of claim 121, wherein said heart failure is selected from the group consisting of diastolic heart failure, systolic heart failure, congestive heart failure, acute congestive heart failure, and acute decompensated heart failure.

123. The method of claim 122, wherein said heart failure is acute decompensated heart failure.

124. The method of claim 121, wherein said compound or composition is administered intravenously.

* * * * *

UNITED STATES PATENT AND TRADEMARK OFFICE
CERTIFICATE OF CORRECTION

PATENT NO.         : 9,464,061 B2
APPLICATION NO.    : 14/926607
DATED              : October 11, 2016
INVENTOR(S)        : John P. Toscano et al.

Page 1 of 1

It is certified that error appears in the above-identified patent and that said Letters Patent is hereby corrected as shown below:

In the Claims

Column 108 Line 21, "-C(O)NR′R″, -NR′R′″" should be --C(O)NR′R″, -NHR′, -NR′R″--
Column 110 Line 62, "-C(O)NR′R″, -NR′R′″" should be --C(O)NR′R″, -NHR′, -NR′R″--
Column 111 Line 36, "-C(O)NR′R″, -NR′R′″" should be --C(O)NR′R″, -NHR′, -NR′R″--
Column 114 Line 15, "-C(O)NR′R″, -NR′R′″" should be --C(O)NR′R″, -NHR′, -NR′R″--
Column 116 Line 30, "-C(O)NR′R″, -NR′R′″" should be --C(O)NR′R″, -NHR′, -NR′R″--
Column 118 Line 50, "s or a pharmaceutically acceptable salt thereof" should be

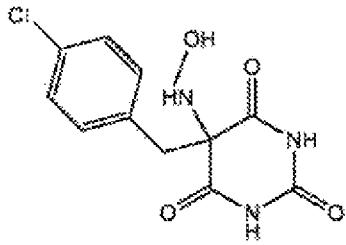

--                          or a pharmaceutically acceptable salt thereof.--

Signed and Sealed this
Seventh Day of November, 2017

Joseph Matal
*Performing the Functions and Duties of the*
*Under Secretary of Commerce for Intellectual Property and*
*Director of the United States Patent and Trademark Office*